United States Patent
Payne et al.

(10) Patent No.: US 12,098,168 B2
(45) Date of Patent: Sep. 24, 2024

(54) XYLR MUTANT FOR IMPROVED XYLOSE UTILIZATION OR IMPROVED CO-UTILIZATION OF GLUCOSE AND XYLOSE PRELIMINARY

(71) Applicant: Genomatica, Inc., San Diego, CA (US)

(72) Inventors: Stephen Thomas Payne, South San Francisco, CA (US); Scott Allen Frykman, South San Francisco, CA (US); Bernardo Moura Torres Da Costa, South San Francisco, CA (US); Isolde Callihan, South San Francisco, CA (US); Sankaranarayanan Venkiteswaran, South San Francisco, CA (US); Leland Ken Wong, South San Francisco, CA (US)

(73) Assignee: Genomatica, Inc., San Diego, CA (US)

( * ) Notice: Subject to any disclaimer, the term of this patent is extended or adjusted under 35 U.S.C. 154(b) by 30 days.

(21) Appl. No.: 17/271,442

(22) PCT Filed: Aug. 29, 2019

(86) PCT No.: PCT/US2019/048888
§ 371 (c)(1),
(2) Date: Feb. 25, 2021

(87) PCT Pub. No.: WO2020/047304
PCT Pub. Date: Mar. 5, 2020

(65) Prior Publication Data
US 2022/0002356 A1 Jan. 6, 2022

Related U.S. Application Data

(60) Provisional application No. 62/731,711, filed on Sep. 14, 2018, provisional application No. 62/726,114, filed on Aug. 31, 2018.

(51) Int. Cl.
| | |
|---|---|
| C07K 14/245 | (2006.01) |
| C12N 1/22 | (2006.01) |
| C12N 9/02 | (2006.01) |
| C12N 9/06 | (2006.01) |
| C12N 9/10 | (2006.01) |
| C12N 9/18 | (2006.01) |
| C12P 7/6436 | (2022.01) |

(52) U.S. Cl.
CPC .............. *C07K 14/245* (2013.01); *C12N 1/22* (2013.01); *C12N 9/0008* (2013.01); *C12N 9/0014* (2013.01); *C12N 9/0077* (2013.01); *C12N 9/1029* (2013.01); *C12N 9/1096* (2013.01); *C12N 9/18* (2013.01); *C12P 7/6436* (2013.01); *C12Y 102/99006* (2013.01); *C12Y 104/99003* (2013.01); *C12Y 114/15003* (2013.01); *C12Y 203/01075* (2013.01); *C12Y 206/01001* (2013.01); *C12Y 301/01067* (2013.01)

(58) Field of Classification Search
None
See application file for complete search history.

(56) References Cited

U.S. PATENT DOCUMENTS

| | | | | |
|---|---|---|---|---|
| 2010/0274033 | A1* | 10/2010 | Sanchez-Riera | ........ C12P 7/649 435/252.33 |
| 2016/0362456 | A1* | 12/2016 | Wang | ............. C12Y 101/01307 |

FOREIGN PATENT DOCUMENTS

WO     1997000962 A1    1/1997

OTHER PUBLICATIONS

Uniprot, Accession No. A0A176XA69, 2017, www.uniprot.org. (Year: 2017).*
Genbank, Accession No. WP_097451202.1, 2017, www.ncbi.nlm.gov. (Year: 2017).*
Uniprot, Accession No. A0A2N7QNM0, Apr. 2018, www.uniprot.org. (Year: 2018).*
Genbank, Accession No. NZ_SQMQ01000042.1, 2022, www.ncbi.nlm.gov. (Year: 2022).*
Desai et al., Regulation of Arabinose and Xylose Metabolism in *Escherichia coli*, Appl. Environ. Microbiol. 76, 2010, 1524-32. (Year: 2010).*
Rodionov et al., Transcriptional regulation of pentose utilisation systems in the Bacillus/Clostridium group of bacteria, FEMS Microbiol. Lett. 205, 2001, 305-14. (Year: 2001).*
Noguchi et al., Genes regulated by AoXlnR, the xylanolytic and cellulolytic transcriptional regulator, in Aspergillus oryzae, Appl. Microbiol. Biotechnol. 85, 2009, 141-54. (Year: 2009).*
Kremling et al., Understanding carbon catabolite repression in *Escherichia coli* using quantitative models, Trends Microbiol. 23, 2015, 99-109. (Year: 2015).*
Ni et al., Structures of the *Escherichia coli* transcription activator and regulator of diauxie, XylR: an AraC DNA-binding family member with a LacI/GalR ligand-binding domain, Nucleic Acid Res. 41, 2013, 1998-2008. (Year: 2013).*
Genbank, Accession No. WP_235635618, 2022, www.ncbi.nlm.gov, teach a protein identical to SEQ ID No. 1 with mutation A336T. (Year: 2022).*
Genbank, Accession No. EIL5439830, 2021, www.ncbi.nlm.gov, teach a protein identical to SEQ ID No. 1 with mutation V831. (Year: 2021).*

(Continued)

*Primary Examiner* — Todd M Epstein
(74) *Attorney, Agent, or Firm* — Harness Dickey & Pierce P.L.C.

(57) ABSTRACT

The disclosure relates to mutant gene(s) that confer upon microorganisms that express them an improved capacity to utilize xylose and improved capacity to co-utilize glucose and xylose thereby resulting in improved growth of the microorganism. Further encompassed are methods of producing fatty acids and fatty acid derivatives from cellulosic biomass, xylose, and/or a glucose/xylose mix by employing the host cells expressing the engineered XylR variants and compositions of biologically produced fatty acids and fatty acid derivatives.

20 Claims, 17 Drawing Sheets
Specification includes a Sequence Listing.

(56) References Cited

OTHER PUBLICATIONS

International Search Report from corresponding PCT Application No. PCT/US2019/048888 dated Feb. 10, 2020.
Written Opinion from corresponding PCT Application No. PCT/US2019/048888 dated Feb. 10, 2020.
Salto, R., et al., "Modulation of the Function of the Signal Receptor Domain of XylR, a Member of a Family of Prokaryotic Enhancer-Like Positive Regulators," Journal of Bacteriology, 180(3): 600-604 (1998).
Sievert, C., et al., "Experimental evolution reveals an effective avenue to release catabolite repression via mutations in XylR," PNAS, 114(28): 7349-7354 (2017).
Stephan, R., et al., "Complete Genome Sequence of Cronobacter turicensis LMG 23827, a Food-Borne Pathogen Causing Death in Neonates," Journal of Bacteriology, 193(1): 309-310 (2011).
Shin, J.H., et al., "Purification and Characterization of a Regulatory Protein XylR in the D-Xylose Operon from *Escherichia coli*," J. Microbiol. Biotechnol., 11(6): 1102-1010 (2001).
Database UniProt (Online) XP002806194, Database accession No. C9Y336 (2009).
Partial Search Report from corresponding EP Application No. 19854591.5 dated May 2, 2022.
International Preliminary Report on Patentability from corresponding PCT Application No. PCT/US2019/048888 dated Mar. 2, 2021.

\* cited by examiner

XYLR MUTANT FOR IMPROVED XYLOSE UTILIZATION OR IMPROVED CO-UTILIZATION OF GLUCOSE AND XYLOSE PRELIMINARY

REFERENCE TO RELATED APPLICATIONS

This application claims the benefit of and priority to U.S. Provisional Patent Application No. 62/726,114, filed Aug. 31, 2018, and U.S. Provisional Patent Application No. 62/731,711, filed Sep. 14, 2018, which are incorporated herein by reference in their entireties.

REFERENCE TO A SEQUENCE LISTING

This application contains references to amino acid sequences and/or nucleic acid sequences as an ASC II text file. The name of the ASC II text file is "62799632_1.TXT". It was created on 23 Feb. 2021 and is 10 KB. The aforementioned sequence listing is hereby incorporated by reference in its entirety pursuant to 37 C.F.R. § 1.52(e).

BACKGROUND

To meet the worldwide demands of a growing human population for energy and resources, and to reduce reliance on limited fossil energy, the use of renewable technologies for the production of energy and consumer products must be increased.

Exemplary renewable technologies include the use of microbial systems for the production of chemicals and fuels. Microbial systems for the production of biofuels and various chemicals are well known in the art (see e.g., U.S. Pat. Nos. 9,133,406; 9,340,801; 9,200,299; 9,068,201; 8,999,686; 8,658,404; 8,597,922; 8,535,916; 8,530,221; 8,372,610; 8,323,924; 8,313,934; 8,283,143; 8,268,599; 8,183,028; 8,110,670; 8,110,093; and 8,097,439; etc). Unfortunately however, the full benefits that derive from microbial systems can be limited by the nature of the feedstocks available for production.

Hydrolysates are commonly used as feedstocks for the biological production of chemicals. These feedstocks are cheaper than pure glucose, potentially lowering the cost of biological production processes. The most abundant sugars in hydrolysates are glucose and xylose. Unfortunately however, xylose has a lower utilization rate than glucose and as a practical matter often cannot be efficiently utilized in the presence of glucose due to the diauxic effect.

Thus, to allow for higher production of any renewable carbon-based product derived from biological processing of hydrolysate feedstock, what is needed in the art are microbial systems that permit both an increase in xylose utilization rate, and an increase in the co-utilization of glucose and xylose. Fortunately, as will be clear from the disclosure that follows, the present invention provides for these and other needs.

SUMMARY

One aspect of the disclosure provides an engineered XylR variant having improved capacity to utilize xylose and improved capacity to co-utilize glucose and xylose.

In one aspect, the disclosure provides a XylR protein variant in which the XylR protein variant has at least one mutation at a position corresponding to a position of SEQ ID NO:1 selected from positions 83, 88, 89, 112, 120, 141, 145, 146, 147, 150, 154, 155, 247, 270, 280, 286, 289, 295, 305, 306, 313, 333, 336, 337, 351, 364, 365, 372, and 382 of SEQ ID NO: 1.

In one aspect, the disclosure provides a recombinant host cell comprising a XylR protein variant in which the XylR protein variant has at least one mutation at a position corresponding to a position of SEQ ID NO:1 selected from positions 83, 89, 112, 120, 141, 145, 146, 147, 150, 154, 155, 247, 270, 280, 286, 289, 295, 305, 306, 313, 333, 336, 337, 351, 364, 365, 372, and 382 of SEQ ID NO: 1.

In one aspect, the disclosure provides a method for increasing xylose utilization in a recombinant host cell. The method comprising culturing in a culture medium comprising xylose, a recombinant host cell which comprises a XylR protein variant in which the XylR protein variant has at least one mutation at a position corresponding to a position of SEQ ID NO:1 selected from positions 83, 89, 112, 120, 141, 145, 146, 147, 150, 154, 155, 247, 270, 280, 286, 289, 295, 305, 306, 313, 333, 336, 337, 351, 364, 365, 372, and 382 of SEQ ID NO: 1. The expression of XylR protein variant in the recombinant host cell confers improved growth on the recombinant host cell in comparison to the growth of a host cell expressing SEQ ID NO: 1, when the cells are cultured in the in the presence of xylose.

In one aspect, the disclosure provides a method for preparing fatty acid derivatives, the method comprising culturing in a culture medium comprising xylose, a recombinant host cell which comprises at least one heterologous fatty acid derivative biosynthetic enzyme and a XylR protein variant, wherein the XylR protein variant has at least one mutation at a position corresponding to a position of SEQ ID NO:1 selected from positions 83, 89, 112, 120, 141, 145, 146, 147, 150, 154, 155, 247, 270, 280, 286, 289, 295, 305, 306, 313, 333, 336, 337, 351, 364, 365, 372, and 382 of SEQ ID NO: 1.

In one aspect, the disclosure provides a method for preparing $C_5$-$C_{24}$ fatty acid methyl esters (FAME) or $C_5$-$C_{24}$ fatty acid ethyl esters (FAEE) or a combination of $C_5$-$C_{24}$ fatty acid methyl esters (FAME) and $C_5$-$C_{24}$ fatty acid ethyl esters (FAEE), the method comprising culturing in a culture medium comprising xylose: a recombinant host cell which comprises at least one heterologous fatty acid derivative biosynthetic enzyme having ester synthase activity (E.C. 3.1.1.67) and XylR protein variant having, wherein the XylR protein variant has at least one mutation at a position corresponding to a position of SEQ ID NO:1 selected from positions 83, 89, 112, 120, 141, 145, 146, 147, 150, 154, 155, 247, 270, 280, 286, 289, 295, 305, 306, 313, 333, 336, 337, 351, 364, 365, 372, and 382 of SEQ ID NO: 1.

In some embodiments of the above aspects, at least one mutation in the XylR protein is selected from the group consisting of V83C, L89V, L89K, L112R, N120C, Y141R, Q145R, L146R, V147M, E150W, E150G, G154C, V155E, A247V, A247T, R270E, R280V, A286M, A286F, Q289V, R295C, E305M, Q306K, I313L, M333R, A336M, A336G, E337N, E337H, L351T, S364W, L365T, L365V, F372W, and E382K.

In some embodiments, the XylR protein variant further comprises at least one additional mutation at a position selected from positions 121 and 363 corresponding to the position of SEQ ID NO:1. In some embodiments, at least one additional mutation at position 121 and 363 is selected from the group consisting of at least one additional mutation is selected from the group consisting of R121C, R121S, R121T, R121G, R121H, R121V, R121M, T121Y, R121I, R121A, R121L, R121P, R121P, R121F, R121W, and P363S.

In some embodiments of the above aspects, the XylR protein variant can have a combination of two or more amino acid substitutions as compared to the wild type XylR protein selected from the group consisting of V83C, L89V, L89K, L112R, N120C, Y141R, Q145R, L146R, V147M, E150W, E150G, G154C, V155E, A247V, A247T, R270E, R280V, A286M, A286F, Q289V, R295C, E305M, Q306K, I313L, M333R, A336M, A336G, E337N, E337H, L351T, S364W, L365T, L365V, F372W, and E382K. In some embodiments, two or more amino acid substitutions can be selected from the group consisting of L89K and L112R; E150G, H88G, and A246A; R280V and D305G; A286F and Q306K; Q289V and E305M; S364W and R295C.

In some embodiments of the above aspects, the XylR protein variant can have a combination of two or more amino acid substitutions in which at least one substitution is selected from the group consisting of V83C, H88G, L89V, L89K, L112R, N120C, Y141R, Q145R, L146R, V147M, E150W, E150G, G154C, V155E, A247V, A247T, R270E, R280V, A286M, A286F, Q289V, R295C, E305M, Q306K, I313L, M333R, A336M, A336G, E337N, E337H, L351T, S364W, L365T, L365V, F372W, and E382K and at least another substitution is selected from the group consisting of R121C, R121S, R121T, R121G, R121H, R121V, R121M, T121Y, R121I, R121A, R121L, R121P, R121P, R121F, R121W, and P363S.

In some embodiments of the above aspects, the XylR protein variant has at least about 60%, 65%, 70%, 75%, 80%, 85%, 90%, 95%, 97.5%, 99% sequence identity to at least 50, 75, 100, 125, 150, 175, 200, 250, 275, 300, or more contiguous amino acids of SEQ ID NO: 1 and have XylR activity. In some embodiments of the above aspects, the XylR protein variant has at least about 60%, 65%, 70%, 75%, 80%, 85%, 90%, 95%, 97.5%, 99% sequence identity to the entire length of SEQ ID NO: 1 and have XylR activity.

In one aspect, the disclosure provides a XylR protein variant having at least 90% sequence identity to SEQ ID NO: 1 wherein the XylR protein variant has at least one mutation at a position corresponding to position 382 of SEQ ID NO:1 and, wherein the XylR protein variant does not have a mutation at a position corresponding to position 121 of SEQ ID NO:1 nor a mutation at position corresponding to 363 of SEQ ID NO:1. In an embodiment, the XylR protein variant has 95% sequence identity to SEQ ID NO: 1. In an embodiment, the XylR protein variant has 98% sequence identity to SEQ ID NO: 1. In some embodiments, at least one mutation at position 382 of SEQ ID NO: 1 is an E382K substitution mutation.

Another aspect of the disclosure provides a recombinant host cell comprising a XylR protein variant having at least 90% sequence identity to SEQ ID NO: 1 and at least one mutation at position 382 of SEQ ID NO: 1 wherein the XylR protein variant does not have a mutation at a position corresponding to position 121 of SEQ ID NO:1 nor a mutation at a position corresponding to 363 of SEQ ID NO:1 wherein expression of the XylR protein variant in the recombinant host cell confers improved growth on the recombinant host cell in comparison to the growth of a host cell expressing SEQ ID NO: 1, when the cells are grown in the in the presence of xylose. In an embodiment, the improved growth results from increased xylose utilization. In an embodiment, the improved growth occurs in the presence of glucose. In an embodiment, the XylR protein variant has 95% sequence identity to SEQ ID NO: 1. In an embodiment, the XylR protein variant has 98% sequence identity to SEQ ID NO: 1. In an embodiment, at least one mutation at position 382 of SEQ ID NO: 1 is an E382K substitution mutation.

Another aspect of the disclosure provides a method for preparing fatty acid derivatives, the method comprising: culturing in a culture medium comprising xylose, a recombinant host cell which comprises at least one heterologous fatty acid derivative biosynthetic enzyme and a XylR protein variant having at least 90% sequence identity to SEQ ID NO: 1 and at least one mutation at position 382 of SEQ ID NO: 1 wherein the XylR protein variant does not have a mutation at a position corresponding to position 121 of SEQ ID NO:1 nor a mutation at a position corresponding to 363 of SEQ ID NO:1. In an embodiment, the XylR protein variant has 95% sequence identity to SEQ ID NO: 1. In an embodiment, the XylR protein variant has 98% sequence identity to SEQ ID NO: 1. In an embodiment, the XylR protein variant having at least one mutation at position 382 of SEQ ID NO: 1 has an E382K substitution mutation. In an embodiment, the culture medium comprising xylose further comprises glucose. In an embodiment, the culture medium is derived from cellulosic biomass. In an embodiment, the fatty acid derivatives are C5-C24 fatty acid derivatives. In an embodiment, at least one heterologous fatty acid derivative biosynthetic enzyme has ester synthase activity (E.C. 3.1.1.67) and the fatty acid derivatives are selected from fatty acid methyl esters (FAME) and fatty acid ethyl esters (FAEE) or a combination thereof.

Another aspect of the disclosure provides a XylR protein variant having at least 90% sequence identity to SEQ ID NO: 1 wherein the XylR protein variant has at least one mutation at a position corresponding to position 382 of SEQ ID NO:1 and at least one mutation at position 382 of SEQ ID NO: 1 is an E382K substitution mutation and, wherein the XylR protein variant does not have a mutation at a position corresponding to position 121 of SEQ ID NO:1 nor a mutation at a position corresponding to 363 of SEQ ID NO:1.

Another aspect of the disclosure provides a method for preparing C5-C24 fatty acid derivatives selected from fatty acid methyl esters (FAME) and fatty acid ethyl esters (FAEE) or a combination thereof, the method comprising: culturing in a culture medium comprising xylose: a recombinant host cell which comprises at least one heterologous fatty acid derivative biosynthetic enzyme having ester synthase activity (E.C. 3.1.1.67) and a XylR protein variant having at least 90% sequence identity to SEQ ID NO: 1 wherein the XylR protein variant has at least one mutation at position 382 of SEQ ID NO: 1 and at least one mutation at position 382 of SEQ ID NO: 1 is an E382K substitution mutation, and the XylR protein variant does not have a mutation at a position corresponding to position 121 of SEQ ID NO:1 nor a mutation at a position corresponding to 363 of SEQ ID NO:1. In an embodiment, the XylR protein variant has 95% sequence identity to SEQ ID NO: 1. In an embodiment, the XylR protein variant has 98% sequence identity to SEQ ID NO: 1. In an embodiment, the culture medium comprising xylose further comprises glucose.

In one aspect, the present disclosure provides a XylR protein variant, wherein the XylR protein variant has at least one mutation at a position corresponding to a position of SEQ ID NO:1 selected from positions 83, 88, 89, 112, 120, 141, 145, 146, 147, 150, 154, 155, 247, 270, 280, 286, 289, 295, 305, 306, 313, 333, 336, 337, 351, 364, 365, 372, and 382 of SEQ ID NO: 1.

In one aspect, the present disclosure provides a recombinant host cell comprising a XylR protein variant, wherein the XylR protein variant has at least one mutation at a position corresponding to a position of SEQ ID NO:1 selected from positions 83, 88, 89, 112, 120, 141, 145, 146, 147, 150, 154, 155, 247, 270, 280, 286, 289, 295, 305, 306, 313, 333, 336, 337, 351, 364, 365, 372, and 382 of SEQ ID NO: 1.

In one aspect, the present disclosure provides a method for increasing xylose utilization in a recombinant host cell, the method comprising culturing in a culture medium comprising xylose, a recombinant host cell which comprises a XylR protein variant, wherein the XylR protein variant has at least one mutation at a position corresponding to a position of SEQ ID NO:1 selected from positions 83, 88, 89, 112, 120, 141, 145, 146, 147, 150, 154, 155, 247, 270, 280, 286, 289, 295, 305, 306, 313, 333, 336, 337, 351, 364, 365, 372, and 382 of SEQ ID NO: 1, wherein expression of XylR protein variant confers improved xylose utilization of the recombinant host cell in comparison to the xylose utilization of a host cell expressing SEQ ID NO: 1 when the cells are cultured in the in the presence of xylose.

In some embodiments, the method is used for preparing fatty acid derivative, the method comprising culturing in a culture medium comprising xylose, a recombinant host cell which further comprises at least one heterologous fatty acid derivative biosynthetic enzyme.

In some embodiments, the fatty acid derivative is: a fatty acid ester and wherein at least one heterologous fatty acid derivative biosynthetic enzyme has ester synthase activity, and optionally wherein at least one heterologous fatty acid derivative biosynthetic enzyme is a thioesterase; a ω-hydroxy fatty acid and wherein at least one heterologous fatty acid derivative biosynthetic enzyme has ω-hydroxylase activity (EC 1.14.15.3); a fatty aldehyde and wherein at least one heterologous fatty acid derivative biosynthetic enzyme has carboxylic acid reductase (CAR) activity; a fatty amine and wherein at least one heterologous fatty acid derivative biosynthetic enzyme has carboxylic acid reductase (CAR) activity and another heterologous fatty acid derivative biosynthetic enzyme has carboxylic acid reductase (CAR) activity aminotransferase or amine dehydrogenase activity; or a fatty alcohol acetate esters and wherein the at least one heterologous fatty acid derivative biosynthetic enzyme has carboxylic acid reductase (CAR) activity and another heterologous fatty acid derivative biosynthetic enzyme has a fatty alcohol O-acetyl transferase activity which converts the fatty alcohols to fatty alcohol acetate esters.

In some embodiments, the method is used for preparing $C_5$-$C_{24}$ fatty acid methyl esters (FAME) or $C_5$-$C_{24}$ fatty acid ethyl esters (FAEE) or a combination of $C_5$-$C_{24}$ fatty acid methyl esters (FAME) and $C_5$-$C_{24}$ fatty acid ethyl esters (FAEE), the method comprising culturing in a culture medium comprising xylose: a recombinant host cell which comprises at least one heterologous fatty acid derivative biosynthetic enzyme having ester synthase activity (E.C. 3.1.1.67) and a XylR protein variant having at least 90% sequence identity to SEQ ID NO: 1 wherein the XylR protein variant has at least one mutation at a position corresponding to a position of SEQ ID NO:1 selected from positions 83, 88, 89, 112, 120, 141, 145, 146, 147, 150, 154, 155, 247, 270, 280, 286, 289, 295, 305, 306, 313, 333, 336, 337, 351, 364, 365, 372, and 382 of SEQ ID NO: 1.

In some embodiments, the XylR protein variant, recombinant host cell, or method of any embodiment comprises a XylR protein variant that has 90% sequence identity to SEQ ID NO: 1.

In some embodiments, the XylR protein variant, recombinant host cell, or method of any embodiment comprises a XylR protein variant has 95% sequence identity to SEQ ID NO: 1.

In some embodiments, the XylR protein variant, recombinant host cell, or method of any embodiment comprises at least one mutation selected from the group consisting of V83C, H88G, L89V, L89K, L112R, N120C, Y141R, Q145R, L146R, V147M, E150W, E150G, G154C, V155E, A247V, A247T, R270E, R280V, A286M, A286F, Q289V, R295C, D305M, Q306K, I313L, M333R, A336M, A336G, E337N, E337H, L351T, S364W, L365T, L365V, F372W, and E382K. In some embodiments, the XylR protein variant, recombinant host cell, or method comprises a XylR protein variant that has more than one substitution mutation and is a member selected from the group consisting of: a XylR protein variant having substitution mutation L89K and further comprising L112R; a XylR protein variant having substitution mutation E150G and further comprising H88G; a XylR protein variant having substitution mutation R280V and further comprising D305G; a XylR protein variant having substitution mutation A286F and further comprising Q306K; a XylR protein variant having substitution mutation Q289V and further comprising D305M; and a XylR protein variant having substitution mutation S364W and further comprising R295C.

In some embodiments, the XylR protein variant, recombinant host cell, or method of any embodiment further comprises at least one additional mutation at a position corresponding to a position of SEQ ID NO:1 selected from positions 121 and 363. In some embodiments, the at least one additional mutation is selected from the group consisting of R121C, R121S, R121T, R121G, R121H, R121V, R121M, T121Y, R121I, R121A, R121L, R121P, R121P, R121F, R121W, and P363S.

In some embodiments, the XylR protein variant, recombinant host cell, or method of any embodiment, expression of the XylR protein variant in a recombinant host cell confers improved growth on the recombinant host cell in comparison to the growth of a host cell expressing SEQ ID NO: 1, when the cells are cultured in the in the presence of xylose. In some embodiments, the XylR protein variant has at least one mutation at a position of SEQ ID NO:1 selected from positions 112, 141, 145, 146, 247, 286, 289, 336, 337, 364 and 365 of SEQ ID NO:1, wherein at least one mutation is selected from the group consisting of L112R, Y141R, Q145R, L146R, A247V, A286F, A286M, Q289V, A336G, E337H, S364W and L365V.

In some embodiments, the recombinant host cell of any embodiment expresses at least one heterologous fatty acid derivative biosynthetic enzyme, wherein the XylR protein variant has at least one mutation at a position selected from positions 112, 145, 146, 247, 286, 336, 337, and 365 of SEQ ID NO: 1 and, wherein the recombinant host cell produces an increased amount of fatty acid species (FAS) as compared to an otherwise isogenic host cell that expresses SEQ ID NO:1 when cultured in the presence of xylose. In some embodiments, the XylR protein variant has at least one mutation at a position selected from positions 112, 145, 146, 247, 286, 336, 337, and 365 of SEQ ID NO: 1, wherein at least one mutation is selected from the group consisting of L112R, Q145R, L146R, A247V, A286M, A336G, E337H, and L365V.

In some embodiments, the method of any embodiment comprises a XylR protein variant having at least one mutation at a position selected from positions 112, 145, 146, 247, 286, 336, 337, and 365 SEQ ID NO: 1, wherein at least one mutation is selected from the group consisting of L112R, Q145R, L146R, A247V, A286M, A336G, E337H, and L365V.

In some embodiments, the method of any embodiment comprises culture medium comprising xylose further comprises glucose. In some embodiments, the culture medium is derived from cellulosic biomass.

In one aspect, the present disclosure provides a XylR protein variant, wherein the XylR protein variant has at least one mutation at a position corresponding to position 382 of SEQ ID NO:1.

In one aspect, the present disclosure provides a recombinant host cell comprising a XylR protein variant having at least one mutation at position 382 of SEQ ID NO: 1, wherein expression of the XylR protein variant in the recombinant host cell confers improved growth on the recombinant host cell in comparison to the growth of a host cell expressing SEQ ID NO: 1, when the cells are grown in the in the presence of xylose.

In some embodiments, the XylR protein variant, recombinant host cell, or the method of any embodiment comprises a XylR protein variant further comprising at least one additional mutation at position 121 or 363. In some embodiments, the at least one additional mutation is selected from the group consisting of R121C, R121S, R121T, R121G, R121H, R121V, R121M, T121Y, R121I, R121A, R121L, R121P, R121P, R121F, R121W, and P363S.

In one aspect, the present disclosure provides a method for increasing xylose utilization in a recombinant host cell, the method comprising culturing in a culture medium comprising xylose, a recombinant host cell which comprises a XylR protein variant, wherein the XylR protein variant has at least one mutation at position 382 corresponding to a position of SEQ ID NO:1, wherein expression of XylR protein variant confers improved xylose utilization of the recombinant host cell in comparison to the xylose utilization of a host cell expressing SEQ ID NO: 1 when the cells are cultured in the in the presence of xylose.

In some embodiments, the method is used for preparing fatty acid derivative, the method comprises culturing in a culture medium comprising xylose a recombinant host cell which further comprises at least one heterologous fatty acid derivative biosynthetic enzyme.

In some embodiments, the fatty acid derivative is: a fatty acid ester and wherein at least one heterologous fatty acid derivative biosynthetic enzyme has ester synthase activity, and optionally wherein at least one heterologous fatty acid derivative biosynthetic enzyme is a thioesterase; a ω-hydroxy fatty acid and wherein at least one heterologous fatty acid derivative biosynthetic enzyme has ω-hydroxylase activity (EC 1.14.15.3); a fatty aldehyde and wherein at least one heterologous fatty acid derivative biosynthetic enzyme has carboxylic acid reductase (CAR) activity; a fatty amine and wherein at least one heterologous fatty acid derivative biosynthetic enzyme has carboxylic acid reductase (CAR) activity and another heterologous fatty acid derivative biosynthetic enzyme has carboxylic acid reductase (CAR) activity aminotransferase or amine dehydrogenase activity; or a fatty alcohol acetate esters and wherein the at least one heterologous fatty acid derivative biosynthetic enzyme has carboxylic acid reductase (CAR) activity and another heterologous fatty acid derivative biosynthetic enzyme has a fatty alcohol O-acetyl transferase activity which converts the fatty alcohols to fatty alcohol acetate esters.

In some embodiments, the method is used for preparing $C_5$-$C_{24}$ fatty acid methyl esters (FAME) or $C_5$-$C_{24}$ fatty acid ethyl esters (FAEE) or a combination of $C_5$-$C_{24}$ fatty acid methyl esters (FAME) and $C_5$-$C_{24}$ fatty acid ethyl esters (FAEE), the method comprising culturing in a culture medium comprising xylose: a recombinant host cell which comprises at least one heterologous fatty acid derivative biosynthetic enzyme having ester synthase activity (E.C. 3.1.1.67) and a XylR protein variant having at least one mutation at position 382 of SEQ ID NO: 1.

In some embodiments, the XylR protein variant, recombinant host cell, or method of any embodiment comprises at least one mutation at position 382 of SEQ ID NO: 1 is an E382K substitution mutation.

In some embodiments, the recombinant host cell of any embodiment comprises improved growth results from increased xylose utilization. In some embodiments, the improved growth occurs in the presence of glucose.

In some embodiments, the method of any embodiment comprises culture medium comprising xylose and further comprising glucose. In some embodiments, the culture medium is derived from cellulosic biomass.

Other features, objects and advantages of the invention will be apparent from the detailed description which follows.

DETAILED DESCRIPTION

Definitions

Figure 1:
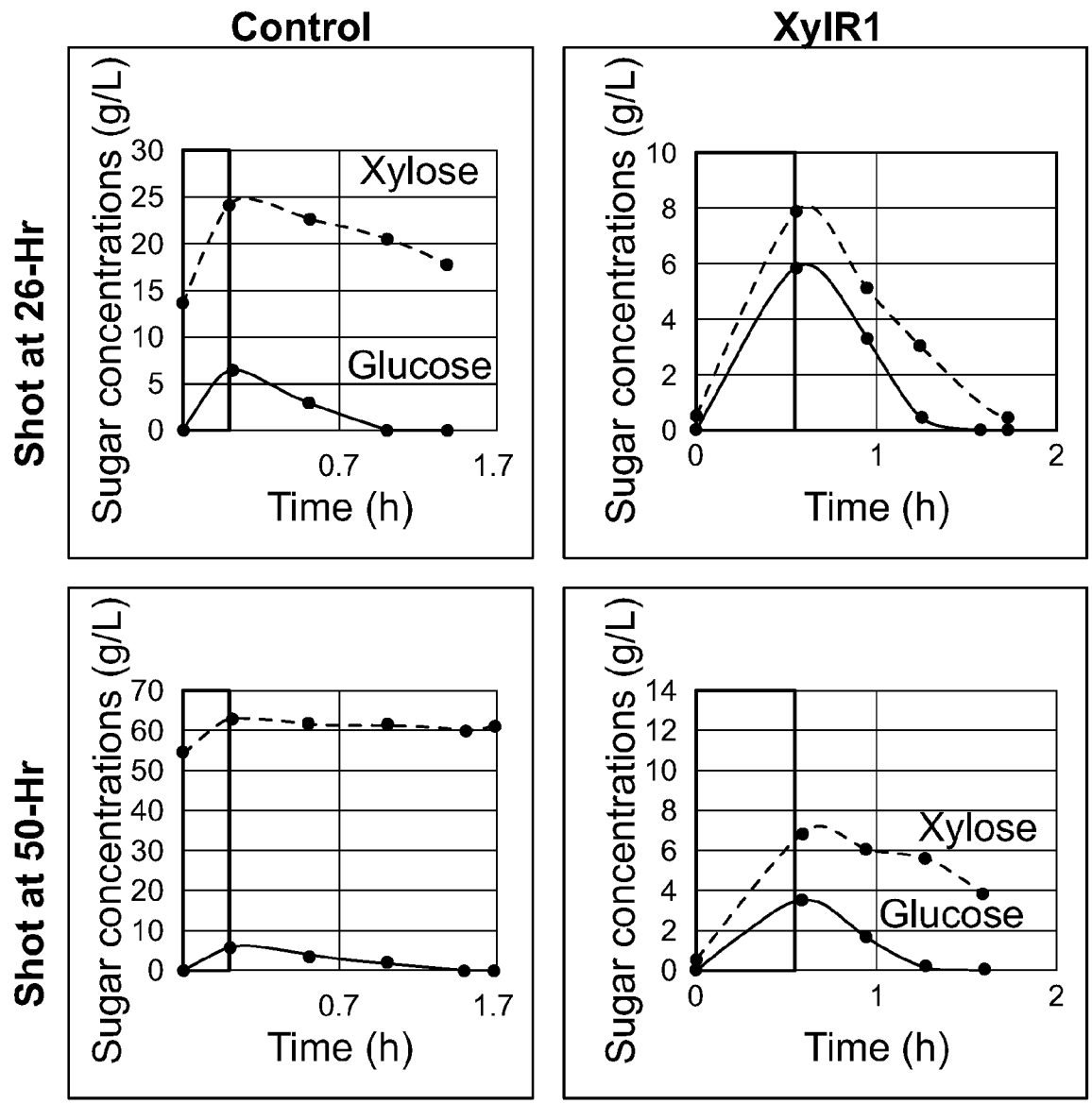
FIG. 1 is a chart illustrating improved co-utilization of glucose and xylose by the E382K XylR mutant (xylR1) as compared to the wild type control.

As used herein and in the appended claims, singular articles such as "a" and "an" and "the" and similar referents in the context of describing the elements are to be construed to cover both the singular and the plural, unless otherwise indicated herein or clearly contradicted by context. Thus, for example, reference to "a host cell" includes two or more such host cells, reference to "a nucleic acid sequence" includes one or more nucleic acid sequences, reference to "an enzyme" includes one or more enzymes, and the like.

As used herein, "about" is understood by persons of ordinary skill in the art and may vary to some extent depending upon the context in which it is used. If there are uses of the term which are not clear to persons of ordinary skill in the art given the context in which the term "about" is used, "about" will mean up to plus or minus 10% of the particular term, including the particular term. Thus about 100 will mean 90 to 110 and will include 100.

As will be understood by one skilled in the art, for any and all purposes, all ranges disclosed herein also encompass any and all possible subranges and combinations of subranges thereof. Furthermore, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Unless defined otherwise, technical and scientific terms used herein have the same meaning as commonly understood by a person of ordinary skill in the art. In particular, this disclosure utilizes routine techniques in the field of recombinant genetics, organic chemistry, fermentation and biochemistry. Basic texts disclosing the general terms in molecular biology and genetics include e.g., Lackie, *Dictionary of Cell and Molecular Biology*, Elsevier (5th ed. 2013). Basic texts disclosing the general methods and terms in biochemistry include e.g., Lehninger *Principles of Biochemistry* Sixth edition, David L. Nelson and Michael M. Cox eds. W. H. Freeman (2012). Basic texts disclosing the general methods and terminology of fermentation include e.g., *Principles of Fermentation Technology*, 3rd Edition by Peter F Stanbury, Allan Whitaker and Stephen J Hall. Butterworth-Heinemann (2016). Basic texts disclosing the general methods and terms organic chemistry include e.g., Favre, Henri A. and Powell, Warren H. *Nomenclature of Organic Chemistry. IUPAC Recommendations and Preferred Name* 2013. Cambridge, UK: The Royal Society of Chemistry, 2013; *Practical Synthetic Organic Chemistry: Reactions, Principles, and Techniques*, Stephane Caron ed., John Wiley and Sons Inc. (2011); *Organic Chemistry*, 9th Edition—Francis Carey and Robert Giuliano, McGraw Hill (2013).

Sequence Accession numbers throughout this description were obtained from databases provided by the NCBI (National Center for Biotechnology Information) maintained by the National Institutes of Health, U.S.A. (which are identified herein as "NCBI Accession Numbers" or alternatively as "GenBank Accession Numbers" or alternatively a simply "Accession Numbers"), and from the UniProt Knowledgebase (UniProtKB) and Swiss-Prot databases provided by the Swiss Institute of Bioinformatics (which are identified herein as "UniProtKB Accession Numbers").

Enzyme Classification (EC) numbers are established by the Nomenclature Committee of the International Union of Biochemistry and Molecular Biology (IUBMB), description of which is available on the IUBMB Enzyme Nomenclature website on the World Wide Web. EC numbers classify enzymes according to the reaction they catalyze. For example, thioesterase enzymatic activity is classified under E.C. 3.1.2.1-3.1.2.27 and 3.1.2.-. A particular classification is based on the activities of different thioesterases on different substrates.

For example, in some exemplary embodiments, thioestrases which catalyze the hydrolysis of the thioester bond of C6-C18 alkyl thioesters, such as acyl-acyl carrier protein thioesters (Acyl-ACP) and acyl-CoenzymeA thioesters (Acyl-CoA) are classified under E.C. 3.1.2.—e.g., 3.1.2.14. Thioesterases are present in most prokaryotes and in the chloroplasts of most plants and algae. The functionality of thioesterases is conserved in most prokaryotes from one species to the next. Thus, different microbial species can carry out the same thioesterase enzymatic activity that is classified under E.C. 3.1.2.-.

The term "fatty acid" as used herein, refers to an aliphatic carboxylic acid having the formula RCOOH wherein R is an aliphatic group having at least 4 carbons, typically between about 4 and about 28 carbon atoms. The aliphatic R group can be saturated or unsaturated, branched or unbranched. Unsaturated "fatty acids" may be monounsaturated or polyunsaturated.

A "fatty acid" or "fatty acids", as used herein, are produced within a cell through the process of fatty acid biosynthesis, through the reverse of fatty acid beta-oxidation, or they can be fed to a cell. As is well known in the art, fatty acid biosynthesis is generally a malonyl-CoA dependent synthesis of acyl-ACPs, while the reverse of beta-oxidation results in acyl-CoAs. Fatty acids fed to cell are converted to acyl-CoAs and acyl-ACPs.

Fatty acid biosynthesis and degradation occur in all life forms, including prokaryotes, single cell eukaryotes, higher eukaryotes, and Archaea. The tools and methods disclosed herein are useful in the production of fatty acid derivatives that are derived through any one or more of fatty acid synthesis, degradation, or feeding in any organism that naturally produces alkyl thioesters.

The term "fatty acid derivative" as used herein, refers to a product made derived from a fatty acid. Thus, a "fatty acid derivative" includes "fatty acids" as defined above. In general, "fatty acid derivatives" include malonyl-CoA derived compounds including acyl-ACP or acyl-ACP derivatives. "Fatty acid derivatives" also include malonyl-CoA derived compounds such as acyl-CoA or acyl-CoA derivatives. Exemplary fatty acid derivatives include fatty acids, fatty acid esters (e.g., waxes, fatty acid esters, fatty acid methyl esters (FAME), fatty acid ethyl esters (FAEE)), fatty alcohol acetate esters (FACE), fatty amines, fatty aldehydes, fatty alcohols, hydrocarbons e.g., alkanes, alkenes, etc, ketones, terminal olefins, internal olefins, 3-hydroxy fatty acid derivatives, bifunctional fatty acid derivatives (e.g., ω-hydroxy fatty acids, 1,3 fatty-diols, α,ω-diols, α,ω-3-hydroxy triols, ω-hydroxy FAME, ω-OH FAEE, etc), and unsaturated fatty acid derivatives, including unsaturated compounds of each of the above mentioned fatty acid derivatives.

The expression "fatty acid derivative composition" as used herein, refers to a composition of fatty acid derivatives, for example a fatty acid composition produced by an organism. A "fatty acid derivative composition" may comprise a single fatty acid derivative species or may comprise a mixture of fatty acid derivative species. In some exemplary embodiments, the mixture of fatty acid derivatives includes more than one type of fatty acid derivative product (e.g., fatty acids, fatty acid esters, fatty alcohols, fatty alcohol acetates, fatty aldehydes, fatty amine, bifunctional fatty acid derivatives, etc.). In other exemplary embodiments, the mixture of fatty acid derivatives includes a mixture of fatty acid esters (or another fatty acid derivative) with different chain lengths, saturation and/or branching characteristics. In other exemplary embodiments, the mixture of fatty acid derivatives comprises predominantly one type of fatty acid derivative. In still other exemplary embodiments, the mixture of fatty acid derivatives comprises a mixture of more than one type of fatty acid derivative product e.g., fatty acid derivatives with different chain lengths, saturation and/or branching characteristics. In still other exemplary embodiments, the mixture of fatty acid derivatives comprises a mixture of fatty esters and beta-hydroxy esters. In still other exemplary embodiments, a fatty acid derivative composition comprises a mixture of fatty alcohols and fatty aldehydes. In still other exemplary embodiments, a fatty acid derivative composition comprises a mixture of FAME and/or FAEE. In still other exemplary embodiments, a fatty acid derivative composition comprises a mixture of fatty alcohol acetate esters (FACE).

As used herein, the term "nucleotide" takes its customary meaning as known in the art. In addition to referring to the naturally occurring ribonucleotide or deoxyribonucleotide monomers, the term "nucleotide" encompasses nucleotide analogs, and modified nucleotides such as amino modified nucleotides. In addition, "nucleotide" includes non-naturally occurring analog structures. Thus, for example, the individual units of a peptide nucleic acid, each containing a base, may be referred to herein as a nucleotide.

The term "polynucleotide" refers to a polymer of ribonucleotides (RNA) or deoxyribonucleotides (DNA) typically in phosphodiester linkage which can be single-stranded or double-stranded and which may contain natural and/or non-natural and/or altered nucleotides. The terms "polynucleotide," "nucleic acid sequence," and "nucleotide sequence" are used interchangeably herein to refer to a polymeric form of nucleotides of any length, either RNA or DNA. These terms refer to the primary structure of the molecule, and thus include polynucleotides that are single-stranded, double-stranded, triple-stranded, quadruplexed, partially double-stranded, branched, hairpinned, circular, in a padlocked conformation, etc. The terms include, as equivalents, analogs of either RNA or DNA made from nucleotide analogs and modified polynucleotides such as, though not limited to methylated and/or capped polynucleotides. A polynucleotide can be in any form, including but not limited to, plasmid, viral, chromosomal, EST, cDNA, mRNA, and rRNA and may be prepared by any known method, including synthetic, recombinant, ex vivo generation, or a combination thereof, as well as utilizing any purification methods known in the art As used herein, the terms "polypeptide" and "protein" are used interchangeably to refer to a polymer of amino acid residues that is typically 12 or more amino acids in length. Polypeptides less than 12 amino acids in length are referred to herein as "peptides". The terms apply to amino acid polymers in which one or more amino acid residue is an artificial chemical mimetic of a corresponding naturally occurring amino acid, as well as to amino acid polymers comprising naturally occurring amino acids. The term "recombinant polypeptide" refers to a polypeptide that is produced by recombinant techniques, e.g., wherein DNA or RNA encoding the expressed protein is inserted into a suitable expression vector that is in turn used to transform a host cell to produce the polypeptide. In some embodiments, DNA or RNA encoding an expressed peptide, polypeptide or protein is inserted into the host chromosome via homologous recombination or other means well known in the art, and is so used to transform a host cell to produce the peptide or polypeptide. Similarly, the terms "recombinant polynucleotide" or "recombinant nucleic acid" or "recombinant DNA" are produced by recombinant techniques that are well known to those of skill in the art (see e.g., methods described in Sambrook et al., Molecular Cloning—A Laboratory Manual, Cold Spring Harbor Press 4$^{th}$ Edition (Cold Spring Harbor, N.Y. 2012) or Current Protocols in Molecular Biology Volumes 1-3, John Wiley & Sons, Inc. (1994-1998) and Supplements 1-115 (1987-2016)).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. In some exemplary embodiments, the single letter code set forth in Table 1 below is used to refer to a particular member of the 20 common naturally occurring amino acids. The single letter amino acid code is well known in the art (see e.g., Lehninger, supra).

TABLE 1

| Amino Acid | Single Letter Code | Amino Acid | Single Letter Code |
|---|---|---|---|
| Glycine | G | Proline | P |
| Alanine | A | Valine | V |
| Leucine | L | Isoleucine | I |
| Methionine | M | Cysteine | C |
| Phenylalanine | F | Tyrosine | Y |
| Tryptophan | W | Histidine | H |
| Lysine | K | Arginine | R |
| Glutamine | Q | Asparagine | N |
| Glutamic acid | E | Aspartic Acid | D |
| Serine | S | Threonine | T |

When referring to two nucleotide or polypeptide sequences, the "percentage of sequence identity" between the two sequences is determined by comparing the two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The "percentage of sequence identity" is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Thus, the expression "percent identity," or equivalently "percent sequence identity" in the context of two or more nucleic acid sequences or peptides or polypeptides, refers to two or more sequences or subsequences that are the same or have a specified percentage of nucleotides or amino acids that are the same (e.g., about 50% identity, preferably 55%, 60%, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured e.g., using a BLAST or BLAST 2.0 sequence comparison algorithm with default parameters (see e.g., Altschul et al. (1990) *J. Mol. Biol.* 215(3):403-410) and/or the NCBI web site at ncbi.nlm.nih.gov/BLAST/) or by manual alignment and visual inspection. Percent sequence identity between two nucleic acid or amino acid sequences also can be determined using e.g., the Needleman and Wunsch algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6 (Needleman and Wunsch (1970) *J. Mol. Biol.* 48:444-453). The percent sequence identity between two nucleotide sequences also can be determined using the GAP program in the GCG software package, using a NWSgapdna.CMP matrix and a gap weight of 40, 50, 60, 70, or 80 and a length weight of 1, 2, 3, 4, 5, or 6. One of ordinary skill in the art can perform initial sequence identity calculations and adjust the algorithm parameters accordingly. A set of parameters that may be used if a practitioner is uncertain about which parameters should be applied to determine if a molecule is within a homology limitation of the claims, are a Blossum 62 scoring matrix with a gap penalty of 12, a gap extend penalty of 4, and a frameshift gap penalty of 5. Additional methods of sequence alignment are known in the biotechnology arts (see, e.g., Rosenberg (2005) *BMC Bioinformatics* 6:278; Altschul et al. (2005) *FEBS J.* 272(20): 5101-5109).

Two or more nucleic acid or amino acid sequences are said to be "substantially identical," when they are aligned and analyzed as discussed above and are found to share about 50% identity, preferably 55%, 60%, 65%, 70%, 75%, 80%, 85%, 90%, 91%, 92%, 93%, 94%, 95%, 96%, 97%, 98%, 99%, or higher identity over a specified region. Two nucleic acid sequences or polypeptide sequences are said to be "identical" if the sequence of nucleotides or amino acid residues, respectively, in the two sequences are the same when aligned for maximum correspondence as described above. This definition also refers to, or may be applied to, the compliment of a test sequence. Identity is typically calculated over a region that is at least about 25 amino acids or nucleotides in length, or more preferably over a region that is 50-100 amino acids or nucleotides in length, or over the entire length of a given sequence.

The expressions "hybridizes under low stringency, medium stringency, high stringency, or very high stringency conditions" describes conditions for hybridization and washing. Guidance for performing hybridization reactions can be found e.g., in Current Protocols in Molecular Biology, John Wiley & Sons, N.Y. (1989), 6.3.1-6.3.6. Aqueous and non-aqueous methods are described in the cited reference and either method can be used. Specific hybridization conditions referred to herein are as follows: (1) low stringency hybridization conditions—6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions—6×SSC at about 45° C., followed by one or more washes in 0.2×SSC, 0.1% SDS at 60° C.; (3) high stringency hybridization conditions—6×SSC at about 45° C., followed by one or more washes in 0.2×SSC, 0.1% SDS at 65° C.; and (4) very high stringency hybridization conditions—0.5M sodium phosphate, 7% SDS at 65° C., followed by one or more washes at 0.2×SSC, 1% SDS at 65° C. Very high stringency conditions (4) are the preferred conditions unless otherwise specified.

The term "endogenous" as used herein refers to a substance e.g., a nucleic acid, protein, etc. that is produced from within a cell. Thus, an "endogenous" polynucleotide or polypeptide refers to a polynucleotide or polypeptide produced by the cell. In some exemplary embodiments an "endogenous" polypeptide or polynucleotide is encoded by the genome of the parental cell (or host cell). In other exemplary embodiments, an "endogenous" polypeptide or polynucleotide is encoded by an autonomously replicating plasmid carried by the parental cell (or host cell). In some exemplary embodiments, an "endogenous" gene is a gene that was present in the cell when the cell was originally isolated from nature i.e., the gene is "native to the cell". In other exemplary embodiments, an "endogenous" gene has been altered through recombinant techniques e.g., by altering the relationship of control and coding sequences. Thus, a "heterologous" gene may, in some exemplary embodiments, be "endogenous" to a host cell.

In contrast, an "exogenous" polynucleotide or polypeptide, or other substance (e.g., fatty acid derivative, small molecule compound, etc.) refers to a polynucleotide or polypeptide or other substance that is not produced by the parental cell and which is therefore added to a cell, a cell culture or assay from outside of the cell.

As used herein the term "native" refers to the form of a nucleic acid, protein, polypeptide or a fragment thereof that is isolated from nature or a nucleic acid, protein, polypeptide or a fragment thereof that is without intentionally introduced mutations.

As used herein, the term "fragment" of a polypeptide refers to a shorter portion of a full-length polypeptide or protein ranging in size from two amino acid residues to the entire amino acid sequence minus one amino acid residue. In certain embodiments of the disclosure, a fragment refers to the entire amino acid sequence of a domain of a polypeptide or protein (e.g., a substrate binding domain or a catalytic domain).

The term "mutagenesis" refers to a process by which the genetic information of an organism is changed in a stable manner to produce a "mutant" or "variant". Mutagenesis of a protein coding nucleic acid sequence to produce a mutant nucleic acid sequence produces a mutant protein. Mutagenesis also refers to changes in non-coding nucleic acid sequences. In some exemplary embodiments, a mutation in a non-coding nucleic acid sequence results in modified protein activity.

Thus, a "mutation", as used herein, refers to a change in a nucleic acid position of a gene or in an amino acid position (residue) of a polypeptide or protein with reference to a control nucleic acid or amino acid sequence. The term "mutation" refers to, in the context of a polynucleotide, a modification to the polynucleotide sequence resulting in a change in the sequence of a polynucleotide with reference to a control or reference polynucleotide sequence. In some exemplary embodiments, a mutant polynucleotide sequence refers to an alteration that does not change the encoded amino acid sequence, for example, with regard to codon optimization for expression purposes. In other exemplary embodiments, a mutation in a polynucleotide sequence modifies a codon in such a way as to result in a modification of the encoded amino acid sequence.

In the context of a protein, the term "mutation" or "mutated" refers to a modification to the amino acid sequence resulting in a change in the sequence of a protein with reference to a control or reference protein sequence. A mutation can refer to a substitution of one amino acid with another amino acid, or an insertion or a deletion of one or more amino acid residues. In some exemplary embodiments, a "mutation" is the replacement of an amino acid with a non-natural amino acid, or with a chemically-modified amino acid residue. In other exemplary embodiments, a "mutation" is a truncation (e.g., a deletion or interruption) in a sequence or a subsequence relative to the precursor sequence or a shortening of a sequence by deletion from one or another end. In other exemplary embodiments, a mutation is an addition of an amino acid or of a subsequence (e.g., two or more amino acids in a stretch, which are inserted between two contiguous amino acids in a precursor protein sequence) within a protein, or at either terminal end of a protein, thereby increasing the length of (or elongating) the protein. Mutations can be introduced into a polynucleotide through any number of methods known to those of ordinary skill in the art, including e.g., random mutagenesis, site-specific mutagenesis, oligonucleotide directed mutagenesis, gene shuffling, directed evolution techniques, combinatorial mutagenesis, chemical synthesis, site saturation mutagenesis, etc.

The term "mutant" or equivalently, "variant" as used herein, refers to a polynucleotide sequence or polypeptide sequence which comprises at least one mutation. Thus, an engineered XylR variant or XylR having improved capacity to utilize xylose and improved capacity to co-utilize glucose and xylose for the production of e.g., fatty acids and fatty acid derivatives will have at least one mutation in its polypeptide sequence in comparison to a control XylR enzyme.

The expression "XylR mutant having improved xylose utilization or improved co-utilization of glucose and xylose" or "XylR mutant having improved xylose utilization and/or improved co-utilization of glucose and xylose" or equivalently, a "XylR protein variant having improved xylose utilization and/or improved co-utilization of glucose and xylose" as used herein refers to an engineered polypeptide/ protein variant of the E. coli xylose-repressor (XylR) which has improved capacity to utilize xylose and/or improved capacity to co-utilize glucose and xylose as measured e.g., by improved growth rates on xylose measured with optical density (OD600) readings as well as improved co-consumption of glucose and xylose in a bioreactor via measurement of total amount of sugar utilized as disclosed in Examples 1 and 2 herein below. Thus, "XylR mutants having improved xylose utilization and/or improved co-utilization of glucose and xylose" may show improved utilization of xylose, improved co-utilization of glucose and xylose or may have both properties.

A "XylR mutant having improved xylose utilization and/ or improved co-utilization of glucose and xylose" or equivalently, a "XylR protein variant having improved xylose utilization and/or improved co-utilization of glucose and xylose" is a protein having at least 90% sequence identity to SEQ ID NO:1 which has at least one mutation at a position corresponding to position 382 of SEQ ID NO:1 and which does not have a mutation at a position corresponding to position 121 of SEQ ID NO:1 nor a mutation at a position corresponding to position 363 of SEQ ID NO:1. In an embodiment, the mutation at position 382 of SEQ ID NO: 1 is an E382K substitution mutation. In an embodiment, a "XylR protein variant having improved xylose utilization and/or improved co-utilization of glucose and xylose" has an amino acid sequence according to SEQ ID NO:3. In an embodiment, a "XylR protein variant having improved xylose utilization and/or improved co-utilization of glucose and xylose" is a protein having at least 91% sequence identity to SEQ ID NO:1 which has at least one mutation at a position corresponding to position 382 of SEQ ID NO:1 and which does not have a mutation at a position corresponding to position 121 of SEQ ID NO:1 nor a mutation at a position corresponding to position 363 of SEQ ID NO:1. In other embodiments, a "XylR protein variant having improved xylose utilization and/or improved co-utilization of glucose and xylose" is a protein having at least 92% sequence identity, at least 93% sequence identity, at least 94% sequence identity, at least 95% sequence identity, at least 96% sequence identity, at least 97% sequence identity, at least 98% sequence identity, at least 99% sequence identity to SEQ ID NO:1 which has at least one mutation at a position corresponding to position 382 of SEQ ID NO:1 and which does not have a mutation at a position corresponding to position 121 of SEQ ID NO:1 nor a mutation at a position corresponding to position 363 of SEQ ID NO:1. In embodiments, XylR protein variants having improved xylose utilization and/or improved co-utilization of glucose and xylose" can be introduced into recombinant host cells to efficiently produce fatty acids and fatty acid derivatives using e.g., lignocellulosic biomass as a feedstock.

The term "gene" as used herein, refers to nucleic acid sequences e.g., DNA sequences, which encode either an RNA product or a protein product, as well as operably-linked nucleic acid sequences that affect expression of the RNA or protein product (e.g., expression control sequences such as e.g., promoters, enhancers, ribosome binding sites, translational control sequences, etc). The term "gene product" refers to either the RNA e.g., tRNA, mRNA and/or protein expressed from a particular gene.

The term "expression" or "expressed" as used herein in reference to a gene, refers to the production of one or more transcriptional and/or translational product(s) of a gene. In exemplary embodiments, the level of expression of a DNA molecule in a cell is determined on the basis of either the amount of corresponding mRNA that is present within the cell or the amount of protein encoded by that DNA produced by the cell. The term "expressed genes" refers to genes that are transcribed into messenger RNA (mRNA) and then translated into protein, as well as genes that are transcribed into other types of RNA, such as e.g., transfer RNA (tRNA), ribosomal RNA (rRNA), and regulatory RNA, which are not translated into protein.

The level of expression of a nucleic acid molecule in a cell or cell free system is influenced by "expression control sequences" or equivalently "regulatory sequences". "Expression control sequences" or "regulatory sequences" are known in the art and include, for example, promoters, enhancers, polyadenylation signals, transcription terminators, nucleotide sequences that affect RNA stability, internal ribosome entry sites (IRES), and the like, that provide for the expression of the polynucleotide sequence in a host cell. In exemplary embodiments, "expression control sequences" interact specifically with cellular proteins involved in transcription (see e.g., Maniatis et al., *Science,* 236: 1237-1245 (1987); Goeddel, Gene Expression Technology: Methods in Enzymology, Vol. 185, Academic Press, San Diego, Calif. (1990)). In exemplary methods, an expression control sequence is operably linked to a polynucleotide sequence. By "operably linked" is meant that a polynucleotide sequence and an expression control sequence(s) are functionally connected so as to permit expression of the polynucleotide sequence when the appropriate molecules (e.g., transcriptional activator proteins) contact the expression control sequence(s). In exemplary embodiments, operably linked promoters are located upstream of the selected polynucleotide sequence in terms of the direction of transcription and translation. In some exemplary embodiments, operably linked enhancers can be located upstream, within, or downstream of the selected polynucleotide.

As used herein, "modified activity" or an "altered level of activity" of a protein/polypeptide e.g., of a engineered XylR variant, refers to a difference in one or more characteristics in the activity the protein/polypeptide as compared to the characteristics of an appropriate control protein e.g., the corresponding parent protein or corresponding wild type protein. Thus, in exemplary embodiments, a difference in activity of a protein having "modified activity" as compared to a corresponding control protein is determined by measuring the activity of the modified protein in a recombinant host cell and comparing that to a measure of the same activity of a corresponding control protein in an otherwise isogenic host cell. Modified activities can be the result of, for example, changes in the binding affinity of a protein for a nucleic acid; changes in the structure of the protein (e.g., changes to the primary structure, such as e.g., changes to the protein's nucleotide coding sequence that result in changes in substrate specificity, DNA binding, changes in observed kinetic parameters, changes in solubility, etc.); changes in protein stability (e.g., increased or decreased degradation of the protein) etc. In some exemplary embodiments, a polypeptide having "modified activity" is a mutant or variant XylR enzyme as disclosed herein.

In exemplary embodiments, a polypeptide disclosed herein has "modified activity" that is e.g., an "improved level of activity". The expression "improved level of activity" as used herein, refers to a polypeptide that has a higher level of biochemical or biological function (e.g., DNA binding or enzymatic activity) as compared to a level of biochemical and/or biological function of a corresponding control polypeptide under the same conditions. The degree of improved activity can be about 10% or more, about 20% or more, about 50% or more, about 75% or more, about 100% or more, about 200% or more, about 500% or more, about 1000% or more, or any range therein.

Thus, "improved activity" may refer to improved catalytic activity or improved catalytic efficiency of a polypeptide, wherein catalytic efficiency refers to e.g. an increase in the reaction rate of the reaction catalyzed by such enzyme of polypeptide. Catalytic activity/catalytic efficiency can be improved e.g., by improving one or more kinetic parameters (measure or calculated) of the reaction such as Vmax (maximum rate the reaction can proceed at), Km (Michaelis constant), kcat (number of substrate molecules turned over per enzyme molecule per second), etc., or any ratio between such parameter, such as kcat/Km (a measure of enzyme efficiency. Thus, "improved catalytic activity" or "improved catalytic efficiency" of a polypeptide can be measured in any number of ways. For example, "improved activity" may be measured as an increase in titer (concentration: g/L, or mg/L, or g/Kg under particular conditions), an improved rate of growth; improved utilization of a particular substrate e.g., xylose; a change in composition (amount of a specific fatty acid species/total fatty acid derivatives (FAS) produced under certain condition e.g., in the presence of xylose, etc.

A "control" sample e.g., a "control" nucleotide sequence, a "control" polypeptide sequence, a "control" cell, etc., or value refers to a sample that serves as a reference, usually a known reference, for comparison to a test sample. For example, in an exemplary embodiment, a test sample comprises an "XylR mutant for improved xylose utilization or improved co-utilization of glucose and xylose", while the control sample comprises the corresponding or designated un-modified/non-variant XylR protein/enzyme (e.g., SEQ ID NO:1). One of skill will recognize that controls can be designed for assessment of any number of parameters. Furthermore, one of skill in the art will understand which controls are valuable in a given situation and will be able to analyze data based on comparisons to control values.

The term "recombinant" as used herein, refers to a genetically modified polynucleotide, polypeptide, cell, tissue, or organism. The term "recombinant applies equally to the first generation of genetically modified polynucleotides, polypeptides, cells, tissues, or organisms as well as to the descendants of genetically modified polynucleotides, polypeptides, cells, tissues, or organisms that carry the genetic modification.

When used with reference to a cell, the term "recombinant" indicates that the cell has been modified by the introduction of a heterologous nucleic acid or protein or has been modified by alteration of a native nucleic acid or protein, or that the cell is derived from a cell so modified and that the derived cell comprises the modification. Thus, for example, "recombinant cells" or equivalently "recombinant host cells" may be modified to express genes that are not found within the native (non-recombinant) form of the cell or may be modified to abnormally express native genes e.g., native genes may be overexpressed, underexpressed or not expressed at all. In exemplary embodiments, a "recombinant cell" or "recombinant host cell" is engineered to express an "XylR mutant for improved xylose utilization or improved co-utilization of glucose and xylose". A recombinant cell can be derived from a microorganism such as a bacterium, a virus or a fungus. In addition, a recombinant cell can be derived from a plant or an animal cell. In exemplary embodiments, a "recombinant host cell" or "recombinant cell" is used to produce one or more fatty acid derivatives including, but not limited to, fatty acids, fatty esters (e.g., waxes, fatty acid esters, fatty esters, fatty acid methyl esters (FAME), fatty acid ethyl esters (FAEE)), fatty alcohol acetate esters (FACE), fatty alcohols, fatty aldehydes, hydrocarbons, fatty amines, terminal olefins, internal olefins, ketones, bifunctional fatty acid derivatives (e.g., omega-hydroxy fatty acids, omega-hydroxy diols, omega-hydroxy FAME, omega-hydroxy FAEE) etc. Therefore, in some exemplary embodiments a "recombinant host cell" is a "production host" or equivalently, a "production host cell". In some exemplary embodiments, the recombinant cell includes one or more polynucleotides, each polynucleotide encoding a polypeptide having fatty acid biosynthetic enzyme activity, wherein the recombinant cell produces a fatty acid derivative composition when cultured in the presence of a carbon source under conditions effective to express the polynucleotides.

When used with reference to a polynucleotide, the term "recombinant" or equivalently "heterologous" indicates that the polynucleotide has been modified by comparison to the native or naturally occurring form of the polynucleotide or has been modified by comparison to a naturally occurring variant of the polynucleotide. In an exemplary embodiment, a recombinant polynucleotide (or a copy or complement of a recombinant polynucleotide) is one that has been manipulated by the hand of man to be different from its naturally occurring form. Thus, in an exemplary embodiment, a recombinant polynucleotide is a mutant form of a native gene or a mutant form of a naturally occurring variant of a native gene wherein the mutation is made by intentional human manipulation e.g., made by saturation mutagenesis using mutagenic oligonucleotides, through the use of UV radiation or mutagenic chemicals, etc. Such a recombinant polynucleotide might comprise one or more point mutations, substitutions, deletions and/or insertions relative to the native or naturally occurring variant form of the gene. Similarly, a polynucleotide comprising a promoter operably linked to a second polynucleotide (e.g., a coding sequence) is a "recombinant" polynucleotide. Thus, a recombinant polynucleotide comprises polynucleotide combinations that are not found in nature. A recombinant protein (discussed supra) is typically one that is expressed from a recombinant polynucleotide, and recombinant cells, tissues, and organisms are those that comprise recombinant sequences (polynucleotide and/or polypeptide).

As used herein, the term "microorganism" refers generally to a microscopic organism. Microorganisms can be prokaryotic or eukaryotic. Exemplary prokaryotic microorganisms include e.g., bacteria, archaea, cyanobacteria, etc. An exemplary bacterium is *Escherichia coli*. Exemplary eukaryotic microorganisms include e.g., yeast, protozoa, algae, etc. In exemplary embodiments, a "recombinant microorganism" is a microorganism that has been genetically altered and thereby expresses or encompasses a heterologous nucleic acid sequence and/or a heterologous protein.

A "production host" or equivalently a "production host cell" is a cell used to produce products. As disclosed herein, a "production host" is typically modified to express or overexpress selected genes, or to have attenuated expression of selected genes. Thus, a "production host" or a "production host cell" is a "recombinant host" or equivalently a "recombinant host cell". Non-limiting examples of production hosts include plant, animal, human, bacteria, yeast, cyanobacteria, algae, and/or filamentous fungi cells. An exemplary "production host" is a recombinant *Escherichia coli* cell.

As used herein "acyl-ACP" refers to an acyl thioester formed between the carbonyl carbon of an acyl chain and the sulfhydryl group of the phosphopantetheinyl moiety of an acyl carrier protein (ACP). In some embodiments an acyl-ACP is an intermediate in the synthesis of fully saturated acyl-ACPs. In other exemplary embodiments an acyl-ACP is an intermediate in the synthesis of unsaturated acyl-ACPs. In some exemplary embodiments, the carbon chain of the acyl group of acyl-ACP has 5, 6, 7, 8, 9, 10, 11, 12, 13, 14, 15, 16, 17, 18, 19, 20, 21, 22, 23, 24, 25, 26, 27 or 28 carbons. In other exemplary embodiments, the carbon chain of the acyl group of acyl-ACP has 12 carbons, 14 carbons, or 16 carbons. In other exemplary embodiments the carbon chain of the acyl group of acyl-ACP is 8 carbons in length. In still other exemplary embodiments, the carbon chain of the acyl group of acyl-ACP is 10 carbons in length. Each of these acyl-ACPs are substrates for enzymes such as e.g., ester synthases, thioesterases, etc that convert the acyl-ACP to fatty acid derivatives.

As used herein, the expression "fatty acid derivative biosynthetic pathway" refers to a biochemical pathway that produces fatty acid derivatives. The enzymes that comprise a "fatty acid derivative biosynthetic pathway" are thus referred to herein as "fatty acid derivative biosynthetic polypeptides" or equivalently "fatty acid derivative enzymes". Thus, for example, a thioesterase enzyme (e.g., an enzyme having thioesterase activity EC 3.1.2.14) is a "fatty acid derivative biosynthetic peptide" or equivalently a "fatty acid derivative enzyme." Thus the term "fatty acid derivative enzymes" or equivalently "fatty acid derivative biosynthetic polypeptides" refers to, collectively and individually, enzymes that may be expressed or overexpressed to produce fatty acid derivatives. Non-limiting examples of "fatty acid derivative enzymes" or equivalently "fatty acid derivative biosynthetic polypeptides" include e.g., fatty acid synthetases, thioesterases, acyl-CoA synthetases, acyl-CoA reductases, acyl ACP reductases, alcohol dehydrogenases, alcohol O-acyltransferases, fatty alcohol-forming acyl-CoA reductases, fatty acid decarboxylases, fatty aldehyde decarbonylases and/or oxidative deformylases, carboxylic acid reductases, fatty alcohol O-acetyl transferases, ester synthases, etc. "Fatty acid derivative enzymes" or equivalently "fatty acid derivative biosynthetic polypeptides" convert substrates into fatty acid derivatives. In exemplary embodiments, a suitable substrate for a fatty acid derivative enzyme may be a first fatty acid derivative, which is converted by the fatty acid derivative enzyme into a different, second fatty acid derivative.

As used herein, the term "culture" refers to a liquid media comprising viable cells. In one embodiment, a culture comprises cells growing in a predetermined culture media under controlled conditions, for example, a culture of recombinant host cells grown in liquid media comprising a selected carbon source and nitrogen. "Culturing" or "cultivation" refers to growing a population of host cells (e.g., recombinant host cells) under suitable conditions in a liquid or solid medium. In certain embodiments, culturing refers to the bioconversion of a substrate to an end-product. Culturing media are well known and individual components of such culture media are available from commercial sources, e.g., Difco™ media and BBL™ media. In one non-limiting example, the aqueous nutrient medium is a "rich medium" including complex sources of nitrogen, salts, and carbon, such as YP medium, comprising 10 g/L of peptone and 10 g/L yeast extract.

As used herein, the term "titer" refers to the quantity of a fatty acid derivative produced per unit volume of host cell culture. The titer may refer to the quantity a particular fatty acid derivative or a combination of a fatty acid derivatives of different chain length or different functionalities such as e.g., a mixture of saturated and unsaturated fatty acid derivatives produced by a given recombinant host cell culture or a fatty acid derivative composition.

The expression "commercial titers" or "commercial titer" as used herein refers to the quantity of a fatty acid derivative produced per unit volume of host cell culture that makes commercial production economically feasible. Typically, commercial titers are in a range that is between about 10 g/L (or equivalently 10 g/Kg) to about 200 g/L or more. Thus, commercial titers are 10 g/L or more, 20 g/L or more, 30 g/L or more, 40 g/L or more, 50 g/L or more, 60 g/L or more, 70 g/L or more, 80 g/L or more, 90 g/L or more, 100 g/L or more, 110 g/L or more, 120 g/L or more, 130 g/L or more, 140 g/L or more, 150 g/L or more, 160 g/L or more, 170 g/L or more, 180 g/L or more, 190 g/L or more, 200 g/L or more.

As used herein, the "yield of a fatty acid derivative" refers to the efficiency by which an input carbon source is converted to product in a host cell. Thus, the expression "yield of a fatty acid derivative" refers to the amount of product produced from a given amount of carbon substrate. Percent yield is the percent of the theoretical yield (product synthesized in ideal conditions, with no loss of carbon or energy). Therefore, percent yield=(mass of product/mass of theoretical yield)×100. The yield may refer to a particular fatty acid derivative or a combination of fatty acid derivatives.

As used herein, the term "productivity" refers to the quantity of fatty acid derivative produced per unit volume of host cell culture per unit time. The productivity may refer to a particular fatty acid derivative or a combination of fatty acid derivatives or other compound(s) produced by a given host cell culture. Thus, in exemplary embodiments, the expression of an XylR mutant having improved xylose utilization and/or improved co-utilization of glucose and xylose in a recombinant host cell such as e.g., $E.$ $coli$ results in increased productivity fatty acid derivatives and/or other compounds as compared to a recombinant host cell expressing the corresponding control XylR enzyme or other appropriate control. As used herein, the term "total fatty species" and "total fatty acid product" and "total fatty acid derivatives" may be used interchangeably herein with reference to the amount (titer) of fatty acid derivatives that are produced by a host cell e.g., a host cell that XylR mutant having improved xylose utilization and/or improved co-utilization of glucose and xylose. Total fatty species, etc. can be evaluated by Gas Chromatography with Flame Ionization Detector (GC-FID). The same terms may be used to mean, for example, total fatty esters, total fatty alcohols, total fatty aldehydes, total fatty amines, and total free fatty acids when referring to a total fatty acid derivative analysis. In particular, the same terms may be used to mean total fatty acid methyl esters, fatty acid ethyl esters, or fatty alcohol acetate esters.

As used herein, the term "carbon source" refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, and gases (e.g., CO and $CO_2$). Exemplary carbon sources include, but are not limited to, monosaccharides, such as glucose, fructose, mannose, galactose, xylose, and arabinose; oligosaccharides, such as fructo-oligosaccharide and galacto-oligosaccharide; polysaccharides such as starch, cellulose, pectin, and xylan; disaccharides, such as sucrose, maltose, cellobiose, and turanose; cellulosic material and variants such as hemicelluloses, methyl cellulose and sodium carboxymethyl cellulose; saturated or unsaturated fatty acids, succinate, lactate, and acetate; alcohols, such as ethanol, methanol, and glycerol, or mixtures thereof. The carbon source can also be a product of photosynthesis, such as glucose. In certain embodiments, the carbon source is biomass. In other embodiments, the carbon source is glucose. In other embodiments the carbon source is sucrose. In other embodiments the carbon source is glycerol. In other embodiments, the carbon source is a simple carbon source. In other embodiments, the carbon source is a renewable carbon source. In other embodiments the carbon source is cellulosic hydrolysates. In other examples, the carbon source is natural gas or a component of natural gas, such as methane, ethane, propane, etc.

As used herein, the term "biomass" refers to any biological material from which a carbon source is derived. In some embodiments, a biomass is processed into a carbon source, which is suitable for bioconversion. In some embodiments, a biomass is processed into cellulosic hydrolysates. In other embodiments, the biomass does not require further processing into a carbon source. The carbon source can be converted into a composition comprising fatty acid derivatives.

An exemplary source of biomass is plant matter or vegetation, such as that derived from corn, sugar cane, switchgrass, rice, wheat, hard wood, soft wood, palm, hemp, etc. Another exemplary source of biomass is metabolic waste products, such as animal matter (e.g., cow manure). Further exemplary sources of biomass include algae and other marine plants, such as macroalgae, and kelp. Biomass also includes waste products from industry, agriculture, forestry, and households, including, but not limited to, glycerol, fermentation waste, ensilage, straw, lumber, pulp, sewage, garbage, cellulosic urban waste, municipal solid waste, oleochemical waste, and food leftovers (e.g., soaps, oils and fatty acids). The term "biomass" also can refer to sources of carbon, such as carbohydrates (e.g., monosaccharides, disaccharides, or polysaccharides).

As used herein, the term "isolated," with respect to products (such as fatty acid derivatives) refers to products that are separated from cellular components, cell culture media, or chemical or synthetic precursors. The fatty acid derivatives produced by the methods disclosed herein can be relatively immiscible in the fermentation broth, as well as in the cytoplasm. Therefore, in exemplary embodiments, fatty acid derivatives collect in an organic phase extracellularly and are thereby "isolated".

As used herein, the terms "purify," "purified," or "purification" mean the removal or isolation of a molecule from its environment by, for example, isolation or separation. "Substantially purified" molecules are at least about 60% free (e.g., at least about 65% free, at least about 70% free, at least about 75% free, at least about 80% free, at least about 85% free, at least about 90% free, at least about 95% free, at least about 96% free, at least about 97% free, at least about 98% free, at least about 99% free) from other components with which they are associated. As used herein, these terms also refer to the removal of contaminants from a sample. For example, the removal of contaminants can result in an increase in the percentage of fatty acid derivatives or other compounds in a sample. For example, when a fatty acid derivative or other compound is produced in a recombinant host cell, the fatty acid derivative or other compound can be purified by the removal of the host cell biomass or its components, such as proteins, nucleic acids, and other cellular components. After purification, the percentage of malonyl-CoA derived compounds including fatty acid derivatives or other compounds in the sample is increased. The terms "purify," "purified," and "purification" are relative terms which do not require absolute purity. Thus, for example, when a fatty acid derivative is produced in recombinant host cells, the fatty acid derivative is "purified" when it is substantially separated from other cellular components (e.g., nucleic acids, polypeptides, lipids, carbohydrates, or other hydrocarbons).

As used herein, the term "attenuate" means to weaken, reduce, or diminish. For example, the activity of a polypeptide can be attenuated, for example by modifying the polypeptide structure to reduce its activity (e.g., by modifying a nucleotide sequence that encodes the polypeptide).

I. Introduction

The use of hydrolysate feedstocks can greatly reduce the costs of producing renewable chemicals by microbial fermentation. However, although hydrolysates of lignocellulosic biomass can be converted into biofuels and chemicals by microbial fermentation, hydrolysate feedstocks typically comprise mixed sugars e.g., glucose, xylose, mannose, etc, and mixed sugar fermentations present significant challenges for cost-effective production of biofuels and chemicals by microbial fermentation.

In particular, the presence of glucose in the growth medium inhibits the use of other sugars in *E. coli* and other species of industrial microorganisms. The consumption of other sugars such as xylose, a pentose sugar, by these microorganisms is initiated only after glucose in the growth medium has been fully consumed. The preferential utilization of glucose to non-glucose sugars often results in lower overall yield and productivity; a phenomenon known as catabolite repression or diauxic growth (see e.g., Kremling, A., et al. (2015) Vol 23(2):99-109; Bruckner R, Titgemeyer F. (2002) FEMS Microbiol. Lett. 209:141-14).

Thus, to allow for higher production of any renewable carbon-based product derived from biological processing of hydrolysate feedstock, what is needed in the art are microbial systems that permit both an increase in xylose utilization rate, and an increase in the co-utilization of glucose and xylose.

Fortunately, the disclosure provides for these and other needs.

II. XylR Mutants Having Improved Xylose Utilization or Improved Co-Utilization of Glucose and Xylose

A. General Methods

This disclosure utilizes routine techniques in the field of recombinant genetics. Basic texts disclosing the general methods and terms in molecular biology and genetics include e.g., Sambrook et al., *Molecular Cloning, a Laboratory Manual*, Cold Spring Harbor Press 4th edition (Cold Spring Harbor, N.Y. 2012); *Current Protocols in Molecular Biology* Volumes 1-3, John Wiley & Sons, Inc. (1994-1998) and Supplements 1-115 (1987-2016). This disclosure also utilizes routine techniques in the field of biochemistry. Basic texts disclosing the general methods and terms in biochemistry include e.g., *Lehninger Principles of Biochemistry* sixth edition, David L. Nelson and Michael M. Cox eds. W. H. Freeman (2012). This disclosure also utilizes routine techniques in industrial fermentation. Basic texts disclosing the general methods and terms in fermentation include e.g., *Principles of Fermentation Technology*, 3rd Edition by Peter F. Stanbury, Allan Whitaker and Stephen J. Hall. Butterworth-Heinemann (2016); *Fermentation Microbiology and Biotechnology*, 2nd Edition, E. M. T. El-Mansi, C. F. A. Bryce, Arnold L. Demain and A. R. Allman eds. CRC Press (2007). This disclosure also utilizes routine techniques in the field of organic chemistry. Basic texts disclosing the general methods and terms in organic chemistry include e.g., *Practical Synthetic Organic Chemistry: Reactions, Principles, and Techniques*, Stephane Caron ed., John Wiley and Sons Inc. (2011); *The Synthetic Organic Chemist's Companion*, Michael C. Pirrung, John Wiley and Sons Inc. (2007); *Organic Chemistry*, 9th Edition—Francis Carey and Robert Giuliano, McGraw Hill (2013).

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized e.g., according to the solid phase phosphoramidite triester method first described by Beaucage & Caruthers, Tetrahedron Letts. 22:1859-1862 (1981), using an automated synthesizer, as described in Van Devanter et al., Nucleic Acids Res. 12:6159-6168 (1984). Purification of oligonucleotides is e.g., by either native acrylamide gel electrophoresis or by anion-exchange HPLC as described in Pearson & Reanier, J. Chrom. 255:137-149 (1983).

The sequence of the cloned genes and synthetic oligonucleotides can be verified after cloning using, e.g., the chain termination method for sequencing double-stranded templates of Wallace et al., Gene 16:21-26 (1981).

B. XylR Mutant Having Improved Xylose Utilization and/or Improved Co-Utilization of Glucose and Xylose

1. General

The sequence of wild type *E. coli* is provided below as SEQ ID NO: 1. The *E. coli* XylR protein also has Uniprot Accession No.: UniProtKB-P0ACI3

```
(SEQ ID NO: 1:

MFTKRHRITLLFNANKAYDROVVEGVGEYLOASOSEWDIFIEEDFRARI

DKIKDWLGDGVIADFDDKQIEQALADVDVPIVGVGGSYHLAESYPPVHY

IATDNYALVESAFLHLKEKGVNRFAFYGLPESSGKRWATEREYAFRQLV

AEEKYRGVVYQGLETAPENWQHAQNRLADWLQTLPPQTGIIAVTDARAR

HILQVCEHLHIPVPEKLCVIGIDNEELTRYLSRVALSSVAQGARQMGYQ

AAKLLHRLLDKEEMPLQRILVPPVRVIERRSTDYRSLTDPAVIQAMHYI
```

-continued

RNHACKGIKVDQVLDAVGISRSNLEKRFKEEVGETIHAMIHAEKLEKAR

SLLISTTLSWEISQMCGYPSLQYFYSVFKKAYDTTPKEYRDVNSEVML

The wild type *E. coli* xylose repressor (XylR) SEQ ID NO:1 is known to activate D-xylose-responsive genes (see e.g., Song S, Park C. (1998) FEMS Microbiol. Lett. 163: 255-264). In particular, XylR-xylose activates transcription of XylAB and XylFGH by binding to a specific site near the start of each operon. The xylAB and xylFGH operons are in opposite orientations of the genome. XylR recruits RNA polymerase to both binding sites using a single dimer attached to two xylose molecules, which loops the DNA.

It is also believed that CRP-cAMP is needed to co-activate xylAB and xylFGH transcription, along with XylR-xylose. cAMP reaches high intracellular concentrations only when glucose has been depleted from the growth media. It is believed that the lack of availability of cAMP gives rise to the diauxic effect, whereby the presence of glucose effectively inhibits uptake of xylose (see e.g., Sievert et al. (2017) PNAS Jul. 11, 2017. 114 (28) 7349-7354).

The linear protein sequence has been analyzed and the 3-dimensional structure of *E. coli* xylose repressor protein (XylR) has been determined (see e.g., Ni et al. (2013) Nuc. Acid. Res. 41(3):1998-2008).

XylR is a 392 amino acid protein that forms a homodimer, which interacts with two xylose molecules and DNA. The protein comprises an N-terminal domain (residues 1-274) and a C-terminal domain (residues 285-392) connected by a linker formed by residues 275-284.

The C-terminal domain is the DNA-binding domain. The C-terminal domain spans amino acids 285-392 with amino acid residues 304-323 forming a helix-turn-helix binding motif. Since residues 304-323 are directly involved in DNA binding, mutations in this region are likely to destroy the function of the XylR protein. However, amino acid substitutions outside the helix-turn-helix region that are within the DNA-binding domain (e.g., residues 285 to 392) could have similar properties to XylR1 see e.g., Sievert et al. (2017) supra.

Without being bound by theory it is believed that the XylR E382K (XylR1) mutation which maps to the XylR DNA-binding domain, affects protein binding, increasing the affinity of the XylR1 protein for the promoter binding sites upstream of xylAB and xylFGH and thus increasing XylAB and XylFGH expression. This stronger interaction also makes the system less sensitive to the need for co-activator CRP-cAMP binding of the promoter sites as well as indicated by the capacity of XylR1 to co-utilize glucose and xylose simultaneously at high rates see e.g., Examples 1 and 2 herein below.

The xylose-binding domain of XylR protein encompasses residues 221-229. This region dimerizes in an antiparallel mode, and ultimately modulates the DNA-binding domain structure to allow DNA binding upon interactions with xylose. Accordingly, mutations in this region are expected to affect the response of the protein to the presence of xylose.

Other functional regions include regions having helical domains such as the region encompassing the E382K (XylR1) mutation. Mutations in helical regions may affect protein function. Regions of the protein having beta-strand structure are also functional domains and so mutations in these regions may result in functional changes.

Some regions of the XylR protein, which are outside the regions of helical and/or beta-strand structures, are likely to have little to no effect on the protein function. Some of these regions include e.g., the first five N-terminal amino acid residues, residues 40-57, residues 74-79, residues 126-133, residues 158-166 and/or residues 181-184.

Furthermore generally, as to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Such "conservatively modified variants" are likely to have minimal to no effect on protein function especially if they occur in regions outside the regions of helical and/or beta-strand structures.

Conservative substitution tables providing functionally similar amino acids are well known in the art. Such conservatively modified variants are in addition to and do not exclude polymorphic variants, interspecies homologs, and alleles of the invention. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Thomas E. (1992) Proteins: Structures and Molecular Properties).

Thus, in exemplary embodiments, the disclosure provides engineered XylR mutant polypeptides having improved xylose utilization and/or improved co-utilization of glucose and xylose. Such mutants are useful for the production of e.g., fatty esters such as e.g., fatty acid methyl esters (FAME) and fatty acid ethyl esters (FAEE), fatty alcohol acetate esters (FACE), fatty amines, fatty aldehydes, fatty alcohols, hydrocarbons, fatty ketones, alkanes, terminal olefins, internal olefins, hydroxy fatty acid derivatives, bifunctional fatty acid derivatives e.g., fatty diacids, fatty diols, unsaturated fatty acid derivatives as compared to the an enzyme having SEQ ID NO:1.

2. Assaying for XylR Mutants Having Improved Xylose Utilization and/or Improved Co-Utilization of Glucose and Xylose In exemplary embodiments, XylR mutants having improved xylose utilization and/or improved co-utilization of glucose and xylose are identified by measuring glucose and xylose utilization as disclosed in Examples 1 and 2 herein below.

In some embodiments, XylR mutants having improved xylose utilization or improved co-utilization of glucose and xylose are identified by measuring the titer of fatty acid derivatives (e.g., free fatty acids (FFA), fatty acid ethyl esters (FAEE), fatty acid methyl esters (FAME), etc.) produced by a bacterial strain comprising an XylR mutant having improved xylose utilization and/or improved co-utilization of glucose and xylose (i.e., a test strain) and comparing these fatty acid derivatives to the titer of fatty acid derivatives (e.g., FFA, FAEE, FAME, etc.) produced by an appropriate control strain that is isogenic to the test strain except for the XylR protein that it comprises. XylR mutants having improved xylose utilization or improved co-utilization of glucose and xylose will produce more fatty acid derivatives (FFA, FAEE, FAME) than the control strain when the strains are cultured in the presence of xylose.

In some embodiments, the total titer of fatty acid derivatives are measured and compared between the test and the control strain. In other embodiments, the percent of the total titer of fatty acid derivatives comprising a specific fatty acid derivative (e.g. C14 fatty acid derivatives) produced by a test strain is measured and compared to the percent of the total titer of fatty acid derivatives comprising a specific fatty acid derivative (e.g. C14 fatty acid derivatives) produced by an appropriate control strain that is isogenic to the test strain except for the control XylR (e.g., SEQ ID NO:1) that it comprises.

In exemplary embodiments, Gas-Chromatography with Flame-Ionization Detection (GC-FID) is used to assay the fatty acid derivative. GC-FID is known in the art (see e.g., Adlard, E. R.; Handley, Alan J. (2001). Gas chromatographic techniques and applications. London: Sheffield Academic). However, any appropriate method for quantitation and analysis may be used e.g., mass spectrometry (MS), Gas Chromatography-mass spectrometry (GC-MS), liquid chromatography-mass spectrometry (LC-MS), thin layer chromatography (TLC), etc.

C. Methods of Making XylR Mutants Having Improved Xylose Utilization and/or Improved Co-Utilization of Glucose and Xylose Engineered XylR mutants having improved xylose utilization or improved co-utilization of glucose and xylose can be prepared by any method known in the art (see e.g., Current Protocols in Molecular Biology, supra). Thus, in exemplary embodiments, mutagenesis is used to prepare polynucleotide sequences encoding XylR mutant/variant having improved xylose utilization or improved co-utilization of glucose and xylose that can then be screened for improved xylose utilization or improved co-utilization of glucose and xylose. In other exemplary embodiments, polynucleotide sequences encoding XylR mutant/variant having improved xylose utilization or improved co-utilization of glucose and xylose that can then be screened for improved xylose utilization or improved co-utilization of glucose and xylose are prepared by chemical synthesis of the polynucleotide sequence (see e.g., M. H. Caruthers et al. (1987) Methods in Enzymology Volume 154, Pages 287-313; Beaucage, S. L. and Iyer, R. P. (1992) Tetrahedron 48(12): 2223-2311).

Mutagenesis methods are well known in the art. An exemplary mutagenesis technique for preparation of engineered XylR mutants having improved xylose utilization or improved co-utilization of glucose and xylose includes e.g., site saturation mutagenesis (see e.g., Chronopoulou EG1, Labrou N E. Curr. Protoc. Protein Sci. 2011 February; Chapter 26: Unit 26.6, John Wiley and Sons, Inc; Steffens, D. L. and Williams., J. G. K (2007) J Biomol Tech. 18(3): 147-149; Siloto, R. M. P and Weselake, R. J. (2012) Biocatalysis and Agricultural Biotechnology 1(3):181-189).

Another exemplary mutagenesis technique for preparation of XylR mutants having improved xylose utilization or improved co-utilization of glucose and xylose includes transfer PCR (tPCR) see e.g., Erijman A., et al. (2011) J. Struct. Biol. 175(2):171-7.

Other exemplary mutagenesis techniques include e.g., error prone Polymerase Chain Reaction (PCR) (see e.g., Leung et al. (1989) Technique 1:11-15; and Caldwell et al. (1992) PCR Methods Applic. 2:28-33).

Another exemplary mutagenesis technique for preparation of engineered XylR variants having improved xylose utilization or improved co-utilization of glucose and xylose includes using oligonucleotide directed mutagenesis (see e.g., Reidhaar-Olson et al. (1988) Science 241:53-57) to generate site-specific mutations in any cloned DNA of interest.

The mutagenized polynucleotides resulting from any method of synthesis or mutagenesis, such as those described above, are then cloned into an appropriate vector or inserted into the host cell genome and the activities of the affected polypeptides encoded by the mutagenized polynucleotides are evaluated as disclosed above.

Those of ordinary skill in the art will recognize that the protocols and procedures disclosed herein can be modified and that such modifications are in accordance with the variations of the disclosure. For example, when method steps are described in a certain order, the ordering of steps can be modified and/or performed in parallel or sequentially.

III. Host Cells and Host Cell Cultures

In view of the present disclosure, the person having ordinary skill in the art will appreciate that any of the embodiments contemplated herein may be practiced with any host cell or microorganism that can be genetically modified via the introduction of one or more nucleic acid sequences that code for the disclosed XylR mutants having improved xylose utilization or improved co-utilization of glucose and xylose. Accordingly, the recombinant microorganisms disclosed herein function as host cells and comprise one or more polynucleotide sequences that include an open reading frame that encodes an XylR mutant having improved xylose utilization and/or improved co-utilization of glucose and xylose together with operably-linked regulatory sequences that facilitate expression of the engineered XylR mutant polypeptide in the host cell.

Exemplary microorganisms that provide suitable host cells, include but are not limited to cells from the genus *Escherichia, Bacillus, Lactobacillus, Pseudomonas, Aspergillus, Marinobacter*. In some exemplary embodiments, the host cell is a Gram-positive bacterial cell. In other exemplary embodiments, the host cell is a Gram-negative bacterial cell. In some embodiments, the host cell is an *E. coli* cell. In other exemplary embodiments, the host cell is a *Bacillus lentus* cell, a *Bacillus brevis* cell, a *Bacillus stearothermophilus* cell, a *Bacillus licheniformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell.

In still other exemplary embodiments, the host cell is a cell from cyanobacterium, green-sulfur bacterium, green non-sulfur bacterium, purple sulfur bacterium, purple non-sulfur bacterium, extremophile, engineered organisms thereof, or a synthetic organism. In some exemplary embodiments, the host cell is an *E. coli* cell. In some exemplary embodiments, the *E. coli* cell is a strain B, a strain C, a strain K, or a strain W *E. coli* cell.

In some exemplary embodiments, host cells comprise optional genetic manipulations and alterations that can be used interchangeably from one host cell to another, depending on what other heterologous enzymes and what native enzymatic pathways are present in the host cell. In one exemplary embodiment, the host cell optionally comprises a fadE and/or an fhuA deletion. In other exemplary embodiments, the host cell is optionally manipulated to have the capacity to produce over 200 mg/L of fatty acid derivatives, over 1000 mg/L of fatty acid derivatives, over 1200 mg/L of fatty acid derivatives, over 1700 mg/L of fatty acid derivatives, over 2000 mg/L of fatty acid derivatives, or over 3000 mg/L of fatty acid derivatives.

As will be discussed in detail herein below, in some exemplary embodiments, the host cells or host microorganisms that are used to express the XylR mutant/variant having improved xylose utilization or improved co-utilization of glucose and xylose further express genes that have enzymatic activities that can increase the production of one or more particular fatty acid derivative(s) such as e.g., fatty esters, fatty alcohols, fatty alcohol acetate esters, fatty acid methyl esters, fatty acid ethyl esters, fatty amines, fatty aldehydes, bifunctional fatty acid derivatives, diacids, alkanes, alkenes or olefins, ketones, etc.

In exemplary embodiments, the host cells or host microorganisms that are used to express XylR mutants having improved xylose utilization or improved co-utilization of glucose and xylose further express ester synthase activity (E.C. 2.3.1.75) for the production of fatty esters. In another exemplary embodiment, the host cell has acyl-ACP reductase (AAR) (E.C. 1.2.1.80) activity and/or alcohol dehydrogenase activity (E.C. 1.1.1.1.) and/or fatty alcohol acyl-CoA reductase (FAR) (E.C. 1.1.1.*) activity and/or carboxylic acid reductase (CAR) (EC 1.2.99.6) activity for the production of fatty alcohols. In another exemplary embodiment, the host cell has acyl-ACP reductase (AAR) (E.C. 1.2.1.80) activity for the production of fatty aldehydes. In another exemplary embodiment, the host cell has acyl-ACP reductase (AAR) (E.C. 1.2.1.80) activity and decarbonylase or fatty aldehyde oxidative deformylating activity EC 4.1.99.5) for the production of alkanes and alkenes. In another exemplary embodiment, the host cell has acyl-CoA reductase (E.C. 1.2.1.50) activity, and acyl-CoA synthetase (FadD) (E.C. 2.3.1.86) activity, for the production of fatty alcohols. In another exemplary embodiment, the host cell has ester synthase activity (E.C. 2.3.1.75) and acyl-CoA synthetase (FadD) (E.C. 2.3.1.86) activity for the production of fatty esters. In another exemplary embodiment, the host cell has OleA activity for the production of ketones. In another exemplary embodiment, the host cell has OleABCD activity for the production of internal olefins. In another exemplary embodiment, the host cell has acyl-ACP reductase (AAR) (E.C. 1.2.1.80) activity and alcohol dehydrogenase activity (E.C. 1.1.1.1.) for the production of fatty alcohols. In another exemplary embodiment, the host cell has decarboxylase activity for making terminal olefins. The expression of enzymatic activities in microorganisms and microbial cells is taught e.g., by the following U.S. Pat. Nos. 9,133,406; 9,340,801; 9,200,299; 9,068,201; 8,999,686; 8,658,404; 8,597,922; 8,535,916; 8,530,221; 8,372,610; 8,323,924; 8,313,934; 8,283,143; 8,268,599; 8,183,028; 8,110,670; 8,110,093; and 8,097,439.

In some exemplary embodiments, host cells or microorganisms that are used to express XylR mutants having improved xylose utilization or improved co-utilization of glucose and xylose comprise certain native enzyme activities that are upregulated or overexpressed in order to produce one or more particular fatty acid derivative(s) such as e.g., fatty esters, fatty acid methyl esters, fatty acid ethyl esters, fatty alcohols, fatty alcohol acetate esters, fatty amines, fatty amides, fatty aldehydes, bifunctional fatty acid derivatives, diacids, etc.

In some exemplary embodiments, a recombinant host cell produces a fatty ester, such as a fatty acid methyl ester (FAME) or a fatty acid ethyl ester (FAEE), fatty alcohol acetate ester (FACE), a fatty alcohol (FALC), a fatty amine, a fatty aldehyde, a bifunctional fatty acid derivative, a diacid, a alkane, a olefin, etc.

The fatty acid derivatives are typically recovered from the culture medium and/or are isolated from the host cells. In one exemplary embodiment, the fatty acid derivatives are recovered from the culture medium (extracellular). In another exemplary embodiment, the fatty acid derivatives are isolated from the host cells (intracellular). In another exemplary embodiment, the fatty acid derivatives or non-fatty acid compounds are recovered from the culture medium and isolated from the host cells.

A fatty acid derivative composition produced by a host cell can be analyzed using methods known in the art, for example, Gas-Chromatography with Flame Ionization Detection (GC-FID) in order to determine the distribution of particular fatty acid derivatives as well as chain lengths and degree of saturation of the components of the fatty acid derivative composition. Similarly, other compounds can be analyzed through methods well known in the art.

IV. Methods of Making Recombinant Host Cells and Cultures

Any method known in the art can be used to engineer host cells to express an XylR mutant having improved xylose utilization and/or improved co-utilization of glucose and xylose to produce e.g., fatty acid derivatives and/or fatty acid derivative compositions or other compounds. Exemplary methods include e.g., the use of vectors, e.g., expression vectors, which comprise a polynucleotide sequence encoding an XylR mutant having improved xylose utilization and/or improved co-utilization of glucose and xylose and/or polynucleotide sequences as disclosed herein. Persons skilled in the art will appreciate that a variety of viral and non-viral vectors can be used in the methods disclosed herein.

In some exemplary embodiments, a polynucleotide (or gene) sequence encoding an XylR mutant having improved xylose utilization and/or improved co-utilization of glucose and xylose is provided to the host cell by way of a recombinant vector that comprises a promoter operably linked to the polynucleotide sequence encoding the XylR mutant having improved xylose utilization and/or improved co-utilization of glucose and xylose. In some exemplary embodiments, the promoter is a developmentally-regulated, an organelle-specific, a tissue-specific, an inducible, a constitutive, or a cell-specific promoter. In some exemplary embodiments, the promoter is inducible by the addition of lactose or isopropylthiogalactoside (IPTG).

Once a polynucleotide sequence encoding an XylR mutant having improved xylose utilization and/or improved co-utilization of glucose and xylose has been prepared and isolated, various methods may be used to construct expression cassettes, vectors and other DNA constructs. Expression cassettes comprising a polynucleotide sequence encoding an XylR mutant/variant having improved xylose utilization or improved co-utilization of glucose and xylose can be constructed in a variety of ways. The skilled artisan is well aware of the genetic elements that must be present on an expression construct/vector in order to successfully transform, select and propagate the expression construct in host cells. Techniques for manipulation of polynucleotide sequences, such as those encoding an XylR mutant/variant having improved xylose utilization or improved co-utilization of glucose and xylose, such as subcloning nucleic acid sequences into expression vectors, labeling probes, DNA hybridization, and the like are described generally in e.g., Sambrook, et al., supra; Current Protocols in Molecular Biology, supra.

DNA constructs comprising a polynucleotide sequence encoding an XylR mutant/variant having improved xylose utilization or improved co-utilization of glucose and xylose (e.g., SEQ ID NO:4) linked to heterologous DNA sequences e.g., promoter sequences, can be inserted into a variety of vectors. In some exemplary embodiments, the vector chosen is an expression vector that is useful in the transformation of bacteria e.g., *Escherichia coli*. The expression vector may be a plasmid, virus, cosmid, artificial chromosome, nucleic acid fragment, or the like. Such vectors are readily constructed by the use of recombinant DNA techniques well known to those of skill in the art (see e.g., Sambrook et al., supra). The expression vector comprising a polynucleotide sequence encoding a mutant or engineered XylR variant may then be transfected/transformed into target host cells. Successfully transformed cells are then selected based on the presence of a suitable marker gene by methods well known in the art.

A number of recombinant vectors are available to those of skill in the art for use in the stable transformation/transfection of bacteria and other microorganisms (see e.g., Sambrook, et al., supra). Appropriate vectors are readily chosen by one of skill in the art. In an exemplary embodiment, known vectors are used to create expression constructs comprising a polynucleotide sequence encoding a mutant or engineered XylR variant.

Typically, transformation vectors include one or more polynucleotide sequences encoding an XylR mutant having improved xylose utilization and/or improved co-utilization of glucose and xylose operably linked to e.g., a promoter sequence, and a selectable marker. Such transformation vectors also typically include a transcription initiation start site, a ribosome binding site, an RNA processing signal, a transcription termination site, and/or a polyadenylation signal as appropriate.

Thus, in addition to a polynucleotide sequence encoding an XylR mutant having improved xylose utilization and/or improved co-utilization of glucose and xylose, expression constructs prepared as disclosed herein may comprise additional elements. In exemplary embodiments, expression constructs comprising a polynucleotide sequence encoding an XylR mutant having improved xylose utilization and/or improved co-utilization of glucose and xylose also comprise an enhancer sequence such that the expression of the heterologous protein may be enhanced. As is known in the art, enhancers are typically found 5' to the start of transcription, they can often be inserted in the forward or reverse orientation, either 5' or 3' to the coding sequence.

As noted above, transformation/expression vectors typically include a selectable and/or screenable marker gene to allow for the ready identification of transformants. Exemplary selectable marker genes include, but are not limited to those encoding antibiotic resistance (e.g. resistance to kanamycin, ampicillin, etc). Exemplary screenable markers include e.g., an introduced six amino acid histidine tag at the C-terminus of the recombinant protein.

In exemplary embodiments, a selectable or screenable marker gene is employed as, or in addition to, a particular gene of interest, to provide or enhance the capacity to identify transformants. Numerous selectable marker genes are known to the art (see e.g., Sambrook et al, supra).

In some exemplary embodiments, an expression vector further comprises sequences that are joined to the coding sequence of an expressed heterologous nucleic acid, which are removed post-translationally from the initial translation product. In one exemplary embodiment, post-translationally removed sequences facilitate the transport of the protein into or through intracellular or extracellular membranes, thereby facilitating the transport of the protein into compartments inside and/or outside the cell. In an exemplary embodiment, post-translationally removed sequences protect a nascent protein from intracellular proteolytic degradation. In one exemplary embodiment, a nucleic acid segment encoding a leader peptide sequence upstream and in reading frame with a selected coding sequence is used in recombinant expression of the coding sequence in a host cell.

In another exemplary embodiment, an expression construct comprises a bacterial origin of replication, e.g., a ColE1 origin. In still another exemplary embodiment, an expression construct/vector comprises a bacterial selectable marker e.g., an ampicillin, tetracyclin, hygromycin, neomycin or chloramphenicol resistance gene.

As is well known in the art, expression constructs typically comprise restriction endonuclease sites to facilitate vector construction. Exemplary restriction endonuclease recognition sites include, but are not limited to e.g., recognition site for the restriction endonucleases NotI, AatII, SacII, PmeI HindIII, PstI, EcoRI, and BamHI.

DNA constructs a polynucleotide sequence encoding a mutant or engineered XylR variant operably and/or polynucleotide sequences encoding other fatty acid derivative biosynthetic pathway polypeptides linked to a heterologous DNA sequence e.g., a promoter sequence, a marker sequence; a purification moiety; a secretion sequence operatively coupled to the polynucleotide sequence; a targeting sequence, etc. are used to transform cells and produce recombinant host cells having improved xylose utilization or improved co-utilization of glucose and xylose. Exemplary host cells for transformation with expression constructs comprising a polynucleotide sequence encoding an XylR mutant having improved xylose utilization and/or improved co-utilization of glucose and xylose are discussed in detail above.

The appropriate transformation technique is readily chosen by the skilled practitioner. Exemplary transformation/transfection methods available to those skilled in the art include e.g., electroporation, calcium chloride transformation and etc., such methods being well known to the skilled artisan (see e.g., Sambrook, supra). Accordingly, polynucleotide sequences, comprising open reading frames encoding proteins and operably-linked regulatory sequences can be integrated into a chromosome of the recombinant host cells, incorporated in one or more plasmid expression system resident in the recombinant host cells, or both.

The expression vectors disclosed herein typically include a polynucleotide sequence encoding an XylR mutant having improved xylose utilization and/or improved co-utilization of glucose and xylose in a form suitable for expression of the polynucleotide sequence in a host cell. As will be appreciated by those skilled in the art, the design of the expression vector can depend on such factors as e.g., the choice of the host cell to be transformed, the level of expression of polypeptide desired, etc.

V. Evaluating Recombinant Host Cells

In exemplary embodiments, the activity of an XylR mutant having improved xylose utilization and/or improved co-utilization of glucose and xylose is determined by culturing recombinant host cells in the presence of xylose and measuring the characteristics of, for example, improved utilization of xylose and glucose as disclosed herein below in Examples 1 and 2.

Another method for evaluating is measurement of the growth rate of the recombinant host cells in the presence of xylose by measuring optical density (OD600) (see e.g., Example 2). Yet another method for evaluating is concentration measurement of the desired biochemical product (e.g., a fatty acid derivative) synthesized from a carbon source of xylose or a mix of glucose and xylose via analytical instrumentation as disclosed herein.

IV. Products Derived From Recombinant Host Cells

Figure 17:
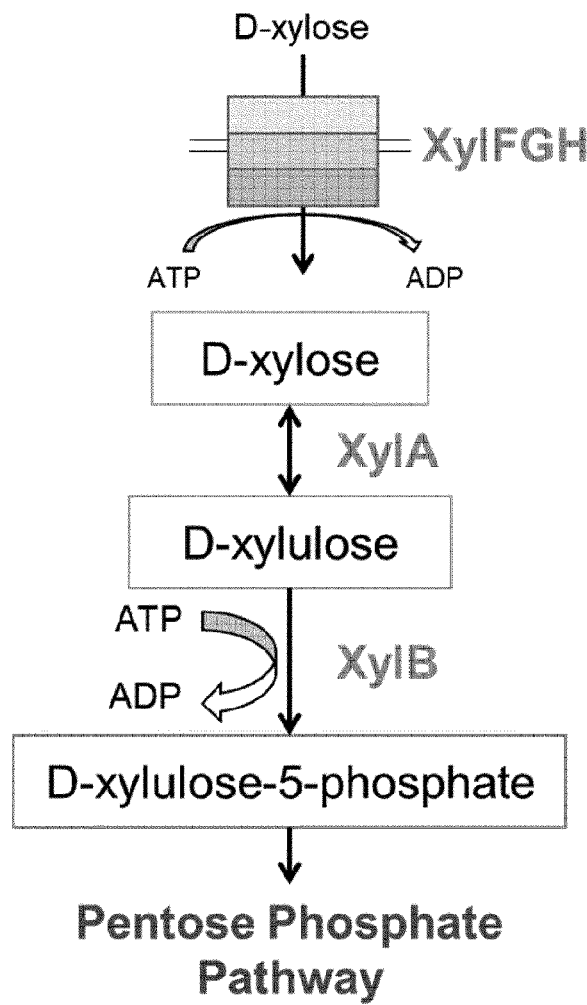
FIG. 17 shows a schematic pathway for xylose utilization in a metabolic pathway.

Strategies to increase xylose utilization or improved co-utilization of glucose and xylose can be used to exploit different carbon sources for the production of fatty acid derivatives by recombinant host cells. Xylose can be used as a carbon source. FIG. 17 shows a schematics of an exemplary metabolic pathway for utilizing xylose.

XylR is a regulator protein that induces expression of XylFGH and XylAB genes that control the transport of xylose and subsequent utilization pathway respectively. The gene product of xylB as shown in FIG. 17, xylulose-5-phosphate, enters central metabolism of E. coli through the well described pentose phosphate pathway. Eventually, acetyl CoA as produced from the pentose phosphate pathway enters fatty acid biosynthesis pathway to produce fatty acid derivatives.

Thus, in exemplary embodiments, recombinant host cells are engineered to comprise, in addition an XylR mutant having improved xylose utilization and/or improved co-utilization of glucose and xylose, one or more polynucleotide sequences encoding one or more "fatty acid derivative biosynthetic polypeptides" or equivalently "fatty acid derivative enzymes". Metabolic engineering of fatty acid derivative biosynthetic pathways to produce fatty acid-derivative compounds (e.g. fatty acid esters, alkanes, olefins, fatty ketones, fatty alcohols, fatty alcohol acetate esters, etc.) using microorganisms to convert biomass-derived sugars to desired products is known in the art see e.g., U.S. Pat. Nos. 9,133,406; 9,340,801; 9,200,299; 9,068,201; 8,999,686; 8,658,404; 8,597,922; 8,535,916; 8,530,221; 8,372,610; 8,323,924; 8,313,934; 8,283,143; 8,268,599; 8,183,028; 8,110,670; 8,110,093; and 8,097,439. Metabolically engineered strains can be cultivated in industrial-scale bioreactors and the resulting products purified using traditional chemical and biochemical engineering techniques.

Thus, in some embodiments, a fatty acid derivative composition comprising e.g., fatty acid esters e.g., FAME, is produced by culturing a recombinant host cell comprising an XylR mutant having improved xylose utilization and/or improved co-utilization of glucose and xylose in the presence of a carbon source comprising xylose under conditions effective to express the XylR mutant.

In some embodiments, substantially all of the fatty acid derivatives produced by culturing a recombinant host cell comprising an XylR mutant having improved xylose utilization and/or improved co-utilization of glucose and xylose under conditions comprising xylose are produced extracellularly. Thus, in some exemplary embodiments, the fatty acid derivatives produced are recovered from the culture medium. In some exemplary embodiments, the recovered fatty acid derivative composition is analyzed using any suitable method known in the art e.g., GC FID, in order to determine and quantify the distribution of particular fatty acid derivatives as well as chain lengths and degree of saturation of the components of the fatty acid derivative composition.

Production of Fatty Acid Derivatives

As discussed above, a recombinant host cell comprising an engineered XylR variant having improved xylose utilization or improved co-utilization of glucose and xylose produces increased amounts of fatty acids as compared to an appropriate control host cell which does not comprise the engineered XylR variant e.g., an isogenic control host cell having a control XylR enzyme (such as SEQ ID NO:1).

In other exemplary embodiments, which are discussed in detail below, in addition to an engineered XylR variant having improved xylose utilization or improved co-utilization of glucose and xylose, a recombinant host cell further comprises additional fatty acid derivative biosynthetic polypeptides which facilitate production of particular types of fatty acid derivatives.

Production of Fatty Aldehydes

In some exemplary embodiments in addition to an engineered XylR variant having improved xylose utilization or improved co-utilization of glucose and xylose, a recombinant host cell further comprises carboxylic acid reductase ("CAR") activity, and thus, the recombinant host cell synthesizes fatty aldehydes and fatty alcohols see e.g., U.S. Pat. No. 9,340,801.

Therefore, in some exemplary embodiments, a fatty aldehyde is produced by expressing or overexpressing in the recombinant host cell a polynucleotide encoding a polypeptide having fatty aldehyde biosynthetic activity such as e.g., carboxylic acid reductase (CAR) activity. Exemplary carboxylic acid reductase (CAR) polypeptides and polynucleotides encoding them include, e.g., FadD9 (EC 6.2.1.-, UniProtKB Q50631, GenBank NP_217106), CarA (GenBank ABK75684), CarB (GenBank YP889972) and related polypeptides disclosed e.g., in U.S. Pat. Nos. 8,097,439 and 9,340,801.

In some exemplary embodiments, the fatty aldehyde produced by the recombinant host cell is then converted into a fatty alcohol or a hydrocarbon. Thus, in some exemplary embodiments in addition to an XylR variant having improved xylose utilization or improved co-utilization of glucose and xylose, a recombinant host cell further comprises acyl-CoA reductase ("FAR" or "ACR") activity, and thus the recombinant host cell synthesizes fatty aldehydes and fatty alcohols (see e.g., U.S. Pat. Nos. 8,658,404, 8,268,599, U.S. Patent Application Publication 2015/0361454).

In some embodiments, the fatty aldehyde produced by the recombinant host cell is converted into a fatty alcohol through the activity of native or heterologous fatty alcohol biosynthetic polypeptides, such as e.g., aldehyde reductases or alcohol dehydrogenases (see e.g., U.S. Patent Application Publication 2011/0250663). Thus, in some exemplary embodiments in addition to an XylR variant having improved xylose utilization or improved co-utilization of glucose and xylose, a recombinant host cell further comprises aldehyde reductase activity or equivalently, alcohol dehydrogenase activity (EC 1.1.1.1), and thus the recombinant host cell synthesizes fatty alcohols. Exemplary fatty alcohol biosynthetic genes include, but are not limited to e.g., alcohol dehydrogenases e.g., AlrA of Acenitobacter sp. M-1 or AlrA homologs; and endogenous E. coli alcohol dehydrogenases such as e.g., DkgA (NP.sub.—417485), DkgB (NP.sub.—414743), YjgB, (AAC77226), YdjL (AAC74846), YdjJ (NP.sub.—416288), AdhP (NP.sub.—415995), YhdH (NP.sub.—417719), YahK (NP.sub.—414859), YphC (AAC75598), and YqhD (Q46856).

Production of Fatty Amines

In some exemplary embodiments, a recombinant host cell which comprises an engineered XylR variant having improved xylose utilization or improved co-utilization of glucose and xylose and which produces fatty aldehydes (e.g., as disclosed herein above) is further modified to comprise a heterologous biosynthetic enzyme that has aminotransferase or amine dehydrogenase activity that converts the fatty aldehydes to fatty amines (see e.g., PCT Publication Number WO 2015/085271).

Production of Fatty Alcohols

In some exemplary embodiments, in addition to an engineered XylR variant having improved xylose utilization or improved co-utilization of glucose and xylose a recombinant host cell further comprises a polynucleotide encoding a polypeptide having fatty alcohol biosynthetic activity, and thus, a fatty alcohol is produced by the recombinant host cell. Thus, in exemplary embodiments, a composition comprising medium-chain fatty alcohols e.g., comprising octanol, is produced by culturing a recombinant host cell in the presence of a carbon source under conditions effective to express an engineered XylR variant having improved xylose utilization or improved co-utilization of glucose and xylose and a fatty alcohol biosynthetic enzyme.

Therefore, in some exemplary embodiments, in addition to an engineered XylR variant having improved xylose utilization or improved co-utilization of glucose and xylose, a recombinant host cell further comprises carboxylic acid reductase (CAR) activity and alcohol dehydrogenase activity and thus, the recombinant host cell synthesizes fatty alcohols e.g., octanol (see e.g., U.S. Pat. No. 9,340,801).

In some exemplary embodiments, native fatty aldehyde biosynthetic polypeptides, such as aldehyde reductases/alcohol dehydrogenases present in the host cell, convert fatty aldehydes to fatty alcohols. In other exemplary embodiments, a native fatty aldehyde reductase/alcohol dehydrogenase is overexpressed to convert fatty aldehydes to fatty alcohols. In other exemplary embodiments, a heterologous aldehyde reductase/alcohol dehydrogenase is introduced into a recombinant host cell and expressed or overexpressed to convert fatty aldehydes to fatty alcohols. Exemplary aldehyde reductase/alcohol dehydrogenase polypeptides useful for converting fatty aldehydes to fatty alcohols are disclosed herein above and in International Patent Application Publication No. WO 2007/136762; WO 2010/062480; U.S. Pat. Nos. 8,110,670; 9,068,201.

In some exemplary embodiments, in addition to an engineered XylR variant having improved xylose utilization or improved co-utilization of glucose and xylose a recombinant host cell further comprises a heterologous polynucleotide encoding a polypeptide having carboxylic acid reductase (EC 6.2.1.3 or EC 1.2.1.42) activity such that the recombinant host cell produces a 1,3 fatty diol when grown in a fermentation broth with a simple carbon source. In other exemplary embodiments, in addition to an engineered XylR variant having improved xylose utilization or improved co-utilization of glucose and xylose, a recombinant host cell further comprises a heterologous polynucleotide encoding a polypeptide having carboxylic acid reductase (EC 6.2.1.3 or EC 1.2.1.42) activity and a heterologous polynucleotide encoding a polypeptide having alcohol dehydrogenase (EC 1.1.1.) activity, wherein the recombinant host cell produces a 1,3 fatty diol, when grown in a fermentation broth with a simple carbon source (see e.g., WO 2016/011430).

Production of Fatty Alcohol Acetate Esters

In some embodiments, fatty alcohols produced in the cell, or in some embodiments fed to a cell, are further processed by a recombinant cell to provide fatty alcohol acetates (FACE). In exemplary embodiments, an alcohol O-acetyltransferase (EC 2.8.1.14) enzyme processes fatty alcohols to fatty alcohol acetate esters (FACE) see e.g., Gabriel M Rodriguez, et al. (2014) Nature Chemical Biology 10, 259-265; Jyun-Liang Lin and Ian Wheeldon (2014) PLoS One. 2014; 9(8): PMCID: PMC4122449.

An exemplary alcohol 0-acetyl transferase is the yeast Aft1 e.g., GenBank accession number AY242062; GenBank accession number AY242063, see e.g., Kevin J. Verstrepen K. J., et al (2003) Appl Environ Microbiol. 2003 September; 69(9): 5228-5237.

In an exemplary embodiment a recombinant host cell comprising an engineered XylR variant having improved xylose utilization or improved co-utilization of glucose and xylose further comprises a carboxylic acid reductase activity (EC 1.2.99.6) sufficient to produce fatty aldehydes and fatty alcohols, and further comprises a fatty alcohol O-acetyl transferase activity which converts the fatty alcohols to fatty alcohol acetate esters.

In a further exemplary embodiment a recombinant host cell comprising an engineered XylR variant having improved xylose utilization or improved co-utilization of glucose and xylose further comprises a carboxylic acid reductase activity (EC 1.2.99.6) which results in the production of a first fatty acid derivative, and further comprises a fatty alcohol 0-acetyl transferase activity which converts the first fatty acid derivative to a second fatty acid derivative, where in the second fatty acid derivative has a higher MIC than the first fatty acid derivative.

In a further exemplary embodiment a recombinant host cell comprising an engineered XylR variant having improved xylose utilization or improved co-utilization of glucose and xylose further comprises a carboxylic acid reductase activity (EC 1.2.99.6) which results in the production of a first fatty acid derivative, and further comprises a fatty alcohol 0-acetyl transferase activity which converts the first fatty acid derivative to a second fatty acid derivative, where in the second fatty acid derivative has a higher LogP than the first fatty acid derivative.

In a further exemplary embodiment a recombinant host cell comprising an engineered XylR variant having improved xylose utilization or improved co-utilization of glucose and xylose further comprises a carboxylic acid reductase activity (EC 1.2.99.6) which results in the production of a first fatty acid derivative, and further comprises a fatty alcohol 0-acetyl transferase activity which converts the first fatty acid derivative to a second fatty acid derivative, where in the presence of the second fatty acid derivative results in an increase in the MIC of the first fatty acid derivative.

In a further exemplary embodiment a recombinant host cell comprising an engineered XylR variant improved xylose utilization or improved co-utilization of glucose and xylose further comprises a carboxylic acid reductase activity (EC 1.2.99.6) which results in the production of a first fatty acid derivative, and further comprises a fatty alcohol 0-acetyl transferase activity which converts the first fatty acid derivative to a second fatty acid derivative, where in the second fatty acid derivative is less toxic than the first fatty acid derivative.

Production of Fatty Esters

In some embodiments, in addition to an engineered XylR variant having improved xylose utilization or improved co-utilization of glucose and xylose a recombinant host cell further comprises a polynucleotide encoding a polypeptide having fatty ester biosynthetic activity, and thus, a fatty ester is produced by the recombinant host cell.

As used herein, the term "fatty ester" or equivalently a "fatty acid ester" refers to any ester made from a fatty acid. In exemplary embodiments, a fatty ester contains an "A side" and a "B side". As used herein, an "A side" of an ester refers to the carbon chain attached to the carboxylate oxygen of the ester. As used herein, a "B side" of an ester refers to the carbon chain comprising the parent carboxylate of the ester. In embodiments where the fatty ester is derived from the fatty acid derivative biosynthetic pathway, the A side is contributed by an alcohol, and the B side is contributed by a fatty acid or alkyl thioester.

Any alcohol can be used to form the A side of the fatty esters. In exemplary embodiments, the alcohol is derived from a fatty acid derivative biosynthetic pathway. In other exemplary embodiments, the alcohol is produced through non-fatty acid derivative biosynthetic pathways e.g., the alcohol is provided exogenously e.g., the alcohol is supplied in the fermentation broth.

The carbon chains comprising the A side or B side can be of any length. In one exemplary embodiment, the fatty ester is a fatty acid methyl ester, wherein the B side is provided by a fatty acid biosynthetic pathway and the A side of the ester is 1 carbon in length. In one exemplary embodiment, the A side is provided through the action of fatty acid O-methyltransferase (FAMT) (EC 2.1.1.15) enzyme (see e.g., Applied and Environmental Microbiology 77(22): 8052-8061).

In another exemplary embodiment, the fatty ester is a fatty acid ethyl ester, wherein the B side is provided by a fatty acid biosynthetic pathway and the A side of the ester is 2 carbons in length.

In one exemplary embodiment, the A side is straight chained. In another exemplary embodiment, the A side is branch chained. In one exemplary embodiment, the B side is straight chained. In another exemplary embodiment, the B side is branch chained. The branched chains can have one or more points of branching. In one exemplary embodiment, the A side is saturated. In another exemplary embodiment, the A side is unsaturated. In one exemplary embodiment, the B side is saturated. In another exemplary embodiment, the B side is unsaturated.

In exemplary embodiments, a recombinant host cell comprises a polynucleotide encoding a polypeptide having ester synthase activity (EC 3.1.1.67). Ester synthases are known in the art see e.g., International Patent Application Publication WO 2011/038134.

In some exemplary embodiments, a fatty acid ester is produced by a recombinant host cell comprising an engineered XylR variant having improved xylose utilization or improved co-utilization of glucose and xylose, and a thioesterase, an acyl-CoA synthetase (fadD) enzyme, and an ester synthase enzyme (see e.g., International Patent Application Publication WO/2011/038134; International Patent Application Publication WO 2007/136762; U.S. Pat. No. 8,110,670).

In an exemplary embodiment a recombinant host cell comprising an engineered XylR variant having improved xylose utilization or improved co-utilization of glucose and xylose further comprises ester synthase activity (EC 3.1.1.67) sufficient to produce fatty esters (such as FAME or FAEE see e.g., U.S. Pat. No. 9,879,239).

Production of Hydrocarbons

In some embodiments, in addition to an engineered XylR variant having improved xylose utilization or improved co-utilization of glucose and xylose, the recombinant host cell further comprises a polynucleotide encoding a polypeptide having fatty aldehyde biosynthetic activity e.g., an acyl-ACP reductase polypeptide (EC 6.4.1.2) and a polynucleotide encoding a polypeptide having hydrocarbon biosynthetic activity, e.g., a decarbonylase (EC 4.1.99.5), oxidative deformylase, or fatty acid decarboxylase, and thus, the recombinant host cell exhibits enhanced production of hydrocarbons (see e.g., U.S. Patent Application Publication 2011/0124071). Thus, in exemplary embodiments, a recombinant host cell comprising an engineered XylR variant having improved xylose utilization or improved co-utilization of glucose and xylose produces a hydrocarbon, e.g., an alkane or an alkene (e.g., a terminal olefin or an internal olefin) or a ketone.

In some exemplary embodiments a fatty aldehyde produced by a recombinant host cell comprising an engineered XylR variant having improved xylose utilization or improved co-utilization of glucose and xylose is converted by decarbonylation, removing a carbon atom, to form a hydrocarbon (see e.g., U.S. Pat. No. 8,110,670 and WO 2009/140695).

In other exemplary embodiments, a fatty acid produced by a recombinant host cell is converted by decarboxylation, removing a carbon atom to form a terminal olefin. Thus, in some exemplary embodiments, in addition to expressing an engineered XylR variant having improved xylose utilization or improved co-utilization of glucose and xylose a recombinant cell further expresses or overexpresses a polynucleotide encoding a hydrocarbon biosynthetic polypeptide, such as a polypeptide having decarboxylase activity as disclosed e.g., in U.S. Pat. No. 8,597,922.

In other exemplary embodiments, alky thioester intermediates are converted by an enzymatic decarboxylative condensation, to form an internal olefin or a ketone. Thus, in some exemplary embodiments, in addition to expressing an engineered XylR variant having improved xylose utilization or improved co-utilization of glucose and xylose, a recombinant cell further expresses or overexpresses a polynucleotide encoding a hydrocarbon biosynthetic polypeptide, such as e.g., a polypeptide having OleA activity thereby producing a ketone (see e.g., in U.S. Pat. No. 9,200,299). In other exemplary embodiments, in addition to expressing an engineered XylR variant having improved xylose utilization or improved co-utilization of glucose and xylose, a recombinant cell further expresses or overexpresses a polynucleotide encoding a hydrocarbon biosynthetic polypeptide, such as e.g., OleCD or OleBCD together with a polypeptide having OleA activity thereby producing an internal olefin is produced (see e.g., U.S. Pat. No. 9,200,299).

Some exemplary hydrocarbon biosynthetic polypeptides are shown in Table 2, below.

TABLE 2

Exemplary Hydrocarbon Biosynthetic Polynucleotides and Polypeptides.

| Protein name | Sequence |
| --- | --- |
| Decarbonylase (ADC) or oxidative deformylase | *Synechococcus elongatus* PCC7942 YP.sub.--400610 (Synpcc7942.sub.--1593) |
| Acyl-ACP Reductase (AAR) | *Synechococcus elongatus* PCC7942 YP_400611 (Synpcc7942_1594) |
| Decarbonylase (ADC) or oxidataive deformylase | *Prochlorococcus mariunus* CCMP1986 PMM0532 |
| Acyl-ACP Reductase (AAR) | *Prochlorococcus marinus* CCMP1986 PMM0533 (NP_892651) |

Production of Omega (ω)-Hydroxylated Fatty Acid Derivatives

In some embodiments, in addition to an engineered XylR variant having improved xylose utilization or improved co-utilization of glucose and xylose, a recombinant host cell further comprises a polynucleotide encoding a polypeptide having ω-hydroxylase activity (EC 1.14.15.3). In exemplary embodiments, the modified ω-hydroxylase has a modified cytochrome P450 monooxygenase (P450) enzymatic activity and efficiently catalyzes the hydroxylastion of the ω-position of hydrocarbon chains in vivo. Thus, the recombinant microorganism produces a medium-chain omega-hydroxylated (o-hydroxylated) fatty acid derivative in vivo when grown in a fermentation broth in the presence of a carbon source from a renewable feedstock (see e.g., PCT Application Publication WO 2014/201474).

In other exemplary embodiments, in addition to an engineered XylR variant having improved xylose utilization or improved co-utilization of glucose and xylose, a recombinant host cell further comprises a polynucleotide encoding a alkane hydroxylase, such as alkA, CYP153A-reductase or a CYP153A-reductase hybrid fusion polypeptide variant (see e.g., WO 2015/195697) such that the recombinant host cell produces omega-hydroxylated-(ω-hydroxylated) and bi-functional fatty acid derivatives and compositions thereof including ω-hydroxylated fatty acids, ω-hydroxylated fatty esters, α,ω-diacids, α,ω-diesters, α,ω-diols and chemicals derived therefrom such as macrolactones and macrocyclic ketones when cultured in medium containing a carbon source under conditions effective to express the alkane hydroxylase, such as AlkA, CYP153 or a CYP153A-reductase hybrid fusion polypeptide variant and engineered XylR variant having improved xylose utilization or improved co-utilization of glucose and xylose.

V. Culture and Fermentation of Recombinant Host Cells

As used herein, fermentation broadly refers to the conversion of organic materials into target substances by recombinant host cells. For example, this includes the conversion of a carbon source by recombinant host cells into fatty acid derivatives such as e.g., fatty acids, fatty acid esters, fatty alcohols, fatty alcohol acetates, etc. by propagating a culture of the recombinant host cells in a media comprising a carbon source. Conditions permissive for the production of target substances such as e.g., fatty acids, fatty esters, fatty alcohols, fatty alcohol acetates, etc., are any conditions that allow a host cell to produce a desired product, such as a fatty acid derivative composition. Suitable conditions include, for example, typical fermentation conditions see e.g., *Principles of Fermentation Technology*, 3rd Edition (2016) supra; *Fermentation Microbiology and Biotechnology*, 2nd Edition, (2007) supra.

Fermentation conditions can include many parameters, well known in the art, including but not limited to temperature ranges, pH levels, rates of aeration, feed rates and media composition. Each of these conditions, individually and in combination, allows the host cell to grow. Fermentation can be aerobic, anaerobic, or variations thereof (such as microaerobic). Exemplary culture media include broths (liquid) or gels (solid). Generally, the medium includes a carbon source (e.g., a simple carbon source derived from a renewable feedstock) that can be metabolized by a host cell directly. In addition, enzymes can be used in the medium to facilitate the mobilization (e.g., the depolymerization of starch or cellulose to fermentable sugars) and subsequent metabolism of the carbon source to produce fatty acid derivatives.

For small scale production, the host cells engineered to produce fatty acid derivative compositions can be grown in batches of, for example, about 100 μL, 200 μL, 300 μL, 400 μL, 500 μL, 1 mL, 5 mL, 10 mL, 15 mL, 25 mL, 50 mL, 75 mL, 100 mL, 500 mL, 1 L, 2 L, 5 L, or 10 L; fermented; and induced to express desired polynucleotide sequences, such as a polynucleotides encoding polypeptides having specific enzymatic activity (e.g., thioesterase (TE), ester synthase (ES), carboxylic acid reductase (CAR), alcohol dehydrogenase (ADH), fatty acyl CoA/ACP reductase (FAR), acyl-CoA reductase (ACR), acetyl CoA carboxylase(ACC) and/or acyl ACP/CoA reductase (AAR) enzymatic activity). For large scale production, the engineered host cells can be grown in cultures having volume of about 10 L, 100 L, 1000 L, 10,000 L, 100,000 L, 1,000,000 L or larger; fermented, and induced to express any desired polynucleotide sequence.

The fatty acid derivative compositions disclosed herein can often be found in the extracellular environment of the recombinant host cell culture and can be readily isolated from the culture medium. A fatty acid derivative such as a fatty acid, a fatty acid ester, fatty aldehyde, fatty ketone, fatty alcohol, a fatty alcohol acetate, etc. may be secreted by the recombinant host cell, transported into the extracellular environment or passively transferred into the extracellular environment of the recombinant host cell culture. The fatty acid derivative compositions may be isolated from a recombinant host cell culture using routine methods known in the art, including but not limited to centrifugation.

Exemplary microorganisms suitable for use as production host cells include e.g., bacteria, cyanobacteria, yeast, algae, filamentous fungi, etc. To produce fatty acid derivative compositions production host cells (or equivalently, host cells) are engineered to comprise fatty acid biosynthesis pathways that are modified relative to non-engineered or native host cells e.g., engineered as discussed above and as disclosed e.g., in U.S. Patent Application Publication 2015/0064782. Production hosts engineered to comprise modified fatty acid biosynthesis pathways are able to efficiently convert glucose or other renewable feedstocks into fatty acid derivatives. Protocols and procedures for high density fermentations for the production of various compounds have been established (see, e.g., U.S. Pat. Nos. 8,372,610; 8,323,924; 8,313,934; 8,283,143; 8,268,599; 8,183,028; 8,110,670; 8,110,093; and 8,097,439).

In some exemplary embodiments, a production host cell is cultured in a culture medium (e.g., fermentation medium) comprising an initial concentration of a carbon source (e.g., a simple carbon source) of about 20 g/L to about 900 g/L. In other embodiments, the culture medium comprises an initial concentration of a carbon source of about 2 g/L to about 10 g/L; of about 10 g/L to about 20 g/L; of about 20 g/L to about 30 g/L; of about 30 g/L to about 40 g/L; or of about 40 g/L to about 50 g/L. In some embodiments, the level of available carbon source in the culture medium can be monitored during the fermentation proceeding. In some embodiments, the method further includes adding a supplemental carbon source to the culture medium when the level of the initial carbon source in the medium is less than about 0.5 g/L.

In some exemplary embodiments, a supplemental carbon source is added to the culture medium when the level of the carbon source in the medium is less than about 0.4 g/L, less than about 0.3 g/L, less than about 0.2 g/L, or less than about 0.1 g/L. In some embodiments, the supplemental carbon source is added to maintain a carbon source level of about 1 g/L to about 25 g/L. In some embodiments, the supplemental carbon source is added to maintain a carbon source level of about 2 g/L or more (e.g., about 2 g/L or more, about 3 g/L or more, about 4 g/L or more). In certain embodiments, the supplemental carbon source is added to maintain a carbon source level of about 5 g/L or less (e.g., about 5 g/L or less, about 4 g/L or less, about 3 g/L or less). In some embodiments, the supplemental carbon source is added to maintain a carbon source level of about 2 g/L to about 5 g/L, of about 5 g/L to about 10 g/L, or of about 10 g/L to about 25 g/L.

In one exemplary embodiment the carbon source for the fermentation is derived from a renewable feedstock. In some embodiments, the carbon source is glucose. In other embodiments, the carbon source is glycerol. Other possible carbon sources include, but are not limited to, fructose, mannose, galactose, xylose, arabinose, starch, cellulose, hemicellulose, pectin, xylan, sucrose, maltose, cellobiose, turanose, acetic acid, ethane, ethanol, methane, methanol, formic acid, and carbon monoxide; cellulosic material and variants such as hemicelluloses, methyl cellulose and sodium carboxymethyl cellulose; saturated or unsaturated fatty acids, succinate, lactate, and acetate; alcohols, such as ethanol, methanol, and glycerol, or mixtures thereof. In one embodiment, the carbon source is derived from corn, sugar cane, sorghum, beet, switch grass, ensilage, straw, lumber, pulp, sewage, garbage, cellulosic urban waste, flu-gas, syn-gas, or carbon dioxide. The simple carbon source can also be a product of photosynthesis, such as glucose or sucrose. In one embodiment, the carbon source is derived from a waste product such as glycerol, flu-gas, or syn-gas; or from the reformation of organic materials such as biomass; or from natural gas or from methane, or from the reformation of these materials to syn-gas; or from carbon dioxide that is fixed photosynthetically, for example fatty acid derivatives may be produced by recombinant cyanobacteria or algae growing photosynthetically and using CO2 as carbon source.

In some embodiments, the carbon source is a cellulosic hydrolysate derived from biomass. Cellulosic hydrolysates are known in the art (see e.g., Yang, B., et al. (2011) Biofuels 2(4): 421). An exemplary source of biomass is plant matter or vegetation, such as corn, sugar cane, or switchgrass. Another exemplary source of biomass is metabolic waste products, such as animal matter (e.g., cow manure). Further exemplary sources of biomass include algae and other marine plants. Biomass also includes waste products from industry, agriculture, forestry, and households, including, but not limited to, fermentation waste, ensilage, straw, lumber, sewage, garbage, cellulosic urban waste, municipal solid waste, and food leftovers.

In some exemplary embodiments, a fatty acid derivative e.g., a fatty acid, fatty acid ester, fatty alcohol, etc., is produced at a concentration of about 0.5 g/L to about 40 g/L. In some embodiments, a fatty acid derivative is produced at a concentration of about 1 g/L or more (e.g., about 1 g/L or more, about 10 g/L or more, about 20 g/L or more, about 50 g/L or more, about 100 g/L or more). In some embodiments, a fatty acid derivative is produced at a concentration of about 1 g/L to about 170 g/L, of about 1 g/L to about 10 g/L, of about 40 g/L to about 170 g/L, of about 100 g/L to about 170 g/L, of about 10 g/L to about 100 g/L, of about 1 g/L to about 40 g/L, of about 40 g/L to about 100 g/L, or of about 1 g/L to about 100 g/L.

In other exemplary embodiments, a fatty acid derivative e.g., a fatty acid, fatty acid ester, fatty alcohol, etc., is produced at a titer of about 25 mg/L, about 50 mg/L, about 75 mg/L, about 100 mg/L, about 125 mg/L, about 150 mg/L, about 175 mg/L, about 200 mg/L, about 225 mg/L, about 250 mg/L, about 275 mg/L, about 300 mg/L, about 325 mg/L, about 350 mg/L, about 375 mg/L, about 400 mg/L, about 425 mg/L, about 450 mg/L, about 475 mg/L, about 500 mg/L, about 525 mg/L, about 550 mg/L, about 575 mg/L, about 600 mg/L, about 625 mg/L, about 650 mg/L, about 675 mg/L, about 700 mg/L, about 725 mg/L, about 750 mg/L, about 775 mg/L, about 800 mg/L, about 825 mg/L, about 850 mg/L, about 875 mg/L, about 900 mg/L, about 925 mg/L, about 950 mg/L, about 975 mg/L, about 1000 mg/L, about 1050 mg/L, about 1075 mg/L, about 1100 mg/L, about 1125 mg/L, about 1150 mg/L, about 1175 mg/L, about 1200 mg/L, about 1225 mg/L, about 1250 mg/L, about 1275 mg/L, about 1300 mg/L, about 1325 mg/L, about 1350 mg/L, about 1375 mg/L, about 1400 mg/L, about 1425 mg/L, about 1450 mg/L, about 1475 mg/L, about 1500 mg/L, about 1525 mg/L, about 1550 mg/L, about 1575 mg/L, about 1600 mg/L, about 1625 mg/L, about 1650 mg/L, about 1675 mg/L, about 1700 mg/L, about 1725 mg/L, about 1750 mg/L, about 1775 mg/L, about 1800 mg/L, about 1825 mg/L, about 1850 mg/L, about 1875 mg/L, about 1900 mg/L, about 1925 mg/L, about 1950 mg/L, about 1975 mg/L, about 2000 mg/L (2 g/L), 3 g/L, 5 g/L, 10 g/L, 20 g/L, 30 g/L, 40 g/L, 50 g/L, 60 g/L, 70 g/L, 80 g/L, 90 g/L, 100 g/L or a range bounded by any two of the foregoing values. In other embodiments, a fatty acid derivative or other compound is produced at a titer of more than 100 g/L, more than 200 g/L, or more than 300 g/L. In exemplary embodiments, the titer of fatty acid derivative or other compound produced by a recombinant host cell according to the methods disclosed herein is from 5 g/L to 200 g/L, 10 g/L to 150 g/L, 20 g/L to 120 g/L and 30 g/L to 100 g/L. The titer may refer to a particular fatty acid derivative or a combination of fatty acid derivatives or another compound or a combination of other compounds produced by a given recombinant host cell culture. In exemplary embodiments, the expression of an engineered XylR variant in a recombinant host cell such as E. coli results in the production of a higher titer as compared to a recombinant host cell expressing the corresponding wild type polypeptide. In one embodiment, the higher titer ranges from at least about 5 g/L to about 200 g/L.

In other exemplary embodiments, the host cells engineered to produce a fatty acid derivative e.g., a fatty acid, fatty acid ester, fatty alcohol, etc., according to the methods of the disclosure have a yield of at least 1%, at least 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, or at least about 30% or a range bounded by any two of the foregoing values. In other embodiments, a fatty acid derivative or derivatives or other compound(s) are produced at a yield of more than about 30%, more than about 35%, more than about 40%, more than about 45%, more than about 50%, more than about 55%, more than about 60%, more than about 65%, more than about 70%, more than about 75%, more than about 80%, more than about 85%, more than about 90%. Alternatively, or in addition, the yield is about 30% or less, about 27% or less, about 25% or less, or about 22% or less. In another embodiment, the yield is about 50% or less, about 45% or less, or about 35% or less. In another embodiment, the yield is about 95% or less, or 90% or less, or 85% or less, or 80% or less, or 75% or less, or 70% or less, or 65% or less, or 60% or less, or 55% or less, or 50% or less. Thus, the yield can be bounded by any two of the above endpoints. For example, the yield of a fatty acid derivative produced by the recombinant host cell according to the methods disclosed herein can be about 5% to about 15%, about 10% to about 25%, about 10% to about 22%, about 15% to about 27%. The yield may refer to a particular fatty acid derivative or a combination of fatty acid derivatives. In addition, the yield will also be dependent on the feedstock used.

In some exemplary embodiments, the productivity of the host cells engineered to produce a fatty acid derivative e.g., a fatty acid, fatty acid ester (e.g., FAME, FAEE), fatty alcohol, etc., according to the methods of the disclosure is at least 100 mg/L/hour, at least 200 mg/L/hour, at least 300 mg/L/hour, at least 400 mg/L/hour, at least 500 mg/L/hour, at least 600 mg/L/hour, at least 700 mg/L/hour, at least 800 mg/L/hour, at least 900 mg/L/hour, at least 1000 mg/L/hour, at least 1100 mg/L/hour, at least 1200 mg/L/hour, at least 1300 mg/L/hour, at least 1400 mg/L/hour, at least 1500 mg/L/hour, at least 1600 mg/L/hour, at least 1700 mg/L/hour, at least 1800 mg/L/hour, at least 1900 mg/L/hour, at least 2000 mg/L/hour, at least 2100 mg/L/hour, at least 2200 mg/L/hour, at least 2300 mg/L/hour, at least 2400 mg/L/hour, 2500 mg/L/hour, or as high as 10 g/L/hour (dependent upon cell mass). For example, the productivity of a malonyl-CoA derived compound including a fatty acid derivative or derivatives or other compound(s) produced by a recombinant host cell according to the methods of the disclosure may be from 500 mg/L/hour to 2500 mg/L/hour, or from 700 mg/L/hour to 2000 mg/L/hour. The productivity may refer to a particular 14 and/or 16 carbon fatty acid derivative or a combination of fatty acid derivatives or other compound(s) produced by a given host cell culture. For example, the expression of an engineered XylR variant in a recombinant host cell such as $E.$ $coli$ results in increased productivity of an 14 and/or 16 carbon fatty acid derivatives or other compounds as compared to a recombinant host cell expressing the corresponding wild type polypeptide. In exemplary embodiments, higher productivity ranges from about 0.3 g/L/h to about 3 g/L/h to about 10 g/L/h to about 100 g/L/h to about a 1000 g/L/h.

VI. Isolation

Bioproducts e.g., compositions comprising fatty acid derivatives as disclosed herein which are produced utilizing recombinant host cells as discussed above are typically isolated from the fermentation broth by methods known in the art. In an exemplary embodiment the compositions comprising fatty acid derivatives as disclosed herein which are produced utilizing recombinant host cells are discussed above are isolated from the fermentation broth by gravity settling, centrifugation, or decantation.

VII. Compositions and Formulations of Fatty Acid Derivatives

Bioproducts e.g., compositions comprising fatty acids and fatty acid derivatives produced utilizing recombinant host cells as discussed in detail above are produced from renewable sources (e.g., from a simple carbon source derived from renewable feedstocks) and, as such, are new compositions of matter. These new bioproducts can be distinguished from organic compounds derived from petrochemical carbon on the basis of dual carbon-isotopic fingerprinting or $^{14}C$ dating. Additionally, the specific source of biosourced carbon (e.g., glucose vs. glycerol) can be determined by dual carbon-isotopic fingerprinting by methods known in the art (see, e.g., U.S. Pat. No. 7,169,588, WO 2016/011430 A1, etc.).

The following examples are offered to illustrate, but not to limit the invention.

EXAMPLES

The following specific examples are intended to illustrate the disclosure and should not be construed as limiting the scope of the claims.

Example 1

This example illustrates that a single amino acid substitution mutation in $E.$ $coli$ XylR (XylR E382K) increased xylose utilization and increased co-utilization of xylose as compared to the wild type xylR control.

Strains IC.200 (IC.187 XylR wild type pSven.037; Control) and sven.938 (IC.187 XylR1 pSven.037; XylR1) were expanded initially in LB media, then overnight at 32° C. in shake flasks containing a minimal salts media (2 g/L $NH_4Cl$, 0.5 g/L NaCl, 0.3 g/L $KH_2PO_4$, 1 mM $MgSO_4$, 0.1 mM $CaCl_2$), 20 g/L glucose, 1 mL/L trace metals solution, 10 g/L ferric citrate, 100 mM Bis Tris phosphate buffer, 20 mL/L methanol, and 100 mg/L spectinomycin), and used at 5% v/v to inoculate 5 L bioreactors containing a defined minimal salts media (0.5 g/L $(NH_4)_2SO_4$, 2 g/L $KH_2PO_4$, 80 mg/L ferric citrate, 1 mL/L trace metals solution, 1 g/L NaCl, 140 mg/L $CaCl$—$H_2O$, 10 mg/L $ZnCl_2$ 2.2 g/L $MgSO_4$-$7H_2O$, 0.25 mL/L trace vitamins solution, 5 g/L each of glucose and xylose, 1 mL/L spectinomycin, and 25 mL/L methanol). The trace metals solution was composed of: 0.5 g/L $H_3BO_3$, 1.9 g/L $CuSO_4$-$5H_2O$, 1 g/L ZnCl, $Na_2MoO_4$-$2H_2O$, $CaCl_2$-$2H_2O$, and 2 mL/L of concentrated hydrochloric acid. The trace vitamins solution was composed of: 0.06 g/L riboflavin, 6 g/L niacin, 5.4 g/L pantothenic acid, 1.4 g/L pyroxidine, 0.06 g/L biotin, and 0.01 g/L folic acid.

Bioreactors were run with the following operational parameters: pH=7.2, temperature=30.5° C., airflow=0.5 v/v/m, and the dissolved oxygen at 30% of saturation.

Sugar feed shots (to 50 g/L total of the initial volume) of a 50:50 mixture of glucose and xylose (total sugar concentration in feed of 610 g/L) were added on-demand to the bioreactor via a dissolved oxygen triggered controller. The automated addition of each of these feed shots was performed in response to a slowdown in the metabolic activity of the culture, which was reflected in a corresponding rise in the residual dissolved oxygen concentration due to a reduced sugar concentration in the bioreactor. Once the residual dissolved oxygen concentration value has risen to some pre-defined offset above the dissolved oxygen setpoint, the feeding controller will trigger the next addition of sugar to the bioreactor.

Two of these feed shots were tracked with additional bioreactor samples taken (shown by black dots) at approximately 26 and 50 hours after bioreactor inoculations.

Cultures are typically induced around 10 hours into the fermentation, so the 26 hour timepoint was selected as this will be the point where the culture was fully induced and producing FAME at its maximal rate with young healthy cells. The cells are using sugar at close to their highest capacity. The 50 hour timepoint was selected as this would be a point where the culture had been induced and producing for around 40 hours, so the cells are older and presumably are in a different state of health than at 26 hours. The cells are a bit worn out, and utilization rates start to decrease normally (with WT XylR but not with XylR1).

The duration of the feed shot is shown in the rectangular box (FIG. 1), with the end of the addition of the feed shot being the zero point on the x-axis. Residual glucose (solid lines) and xylose (dashed lines) concentrations in the sample supernatants were measured at the beginning and end of each of these feed shots using high-performance liquid chromatography (HPLC) which was also used to measure residual glucose and xylose during the subsequent period until the initiation of the next feed shot to quantitatively determine the culture's glucose and xylose consumption levels.

Calculated glucose and xylose utilization rates for both strains at both time points tested (26 and 50 hours EFT) are in the table below. Residual glucose at the initiation of all feed shots is zero.

| Condition | Timepoint | Nominal Glucose Utilization Rate (g/initial L/h) | Nominal Xylose Utilization Rate (g/initial L/h | Residual Xylose at Shot Start |
|---|---|---|---|---|
| Control | 26 hours | 9.4 | 6.2 | 13.7 |
| Control | 50 hours | 12.2 | 2.8 | 54.6 |
| xylR1 | 26 hours | 10.0 | 8.7 | 0.5 |
| xylR1 | 50 hours | 10.8 | 6.5 | 0.4 |

As shown in FIG. 1 and the Table above, the control strain effectively utilizes glucose, but not xylose. At 26 hours at the start of the feed shot, residual xylose concentration in the control strain is high (13.7 g/L), but residual glucose is zero. This suggests that while glucose is being fully utilized from shot to shot, xylose is not such that xylose accumulates in the bioreactor over time. Further sampling out to about 1.5 hours post feed shot shows a reduction in xylose levels, but by the time residual glucose levels have returned to zero, xylose levels have remained elevated, increasing to about 17.5 g/L. At 50 hours, residual glucose levels are again at zero, but xylose levels have increased further (54.6 g/L) suggesting that xylose is not being utilized efficiently by the control strain. Further sampling out to about 1.5 hours post feed shot shows a no reduction in xylose levels while residual glucose concentration returns to zero.

In contrast, in the strain expressing the XylR1 mutant (E382K), at 26 hours at the start of the feed shot, residual xylose concentration in the control strain is low (0.5 g/L), and residual glucose is zero. Further sampling out to about 1.5 hours post feed shot shows xylose decreasing almost to zero, along with glucose. At 50 hours, residual glucose concentration is again at zero, and essentially so is residual xylose concentration. Further sampling out to about 1.5 hours post feed shot shows a reduction in xylose levels to about 4 g/L levels from a high of about 6.5 g/L. Thus, the XylR1 mutant exhibits increased xylose utilization, even in the presence of glucose.

Example 2

This example illustrates that cells expressing the XylR1 mutant show improved growth in the presence of xylose and that the improved growth is due to improved xylose utilization.
IC.187 and Sven.903 (IC.187 XylR1)

IC.187 is an *E. coli* cell with an unmodified xylR locus (XylR WT). sven.903 is isogenic to IC.187 but has the point mutation E382K in the xylR locus. Neither strain has a plasmid present so that there is no FAME production in this context.

IC.187 and sven.903 were grown in high-throughput. Cells were grown overnight as seed cultures in seed minimal medium with 10 g/L glycerol or 10 g/L glucose at 32° C. shaking at 250 (revolutions per minute) RPM. Twenty percent of inoculum was then added to minimal medium with 10 g/L xylose and grown at 32° C. shaking at 250 RPM. Growth was then measured at 8 hr via OD600 readings. Seed Minimal Medium=1× trace vitamins, 0.001 mg/mL thiamine, 0.1 mM $CaCl_2$), 0.01 g/L Ferric Citrate, 1 mM $MgSO_4$, 1× trace minerals, 0.5% MeOH, 100 mM Bis-Tris (pH=7), 0.424 g/L $KH_2PO_4$, 0.376 $Na_2HPO_4$, 10 g/L $(NH_4)_2SO_4$, 2 g/L NaCl. Minimal Medium=same as seed with the following differences: 0.0125% Triton, 2% MeOH, 200 mM Bis-Tris (pH=7), 0.318 g/L $KH_2PO_4$, 0.282 g/L $Na_2HPO_4$, 7.5 g/L $(NH_4)_2SO_4$, 1.5 g/L NaCl.

Figure 2:
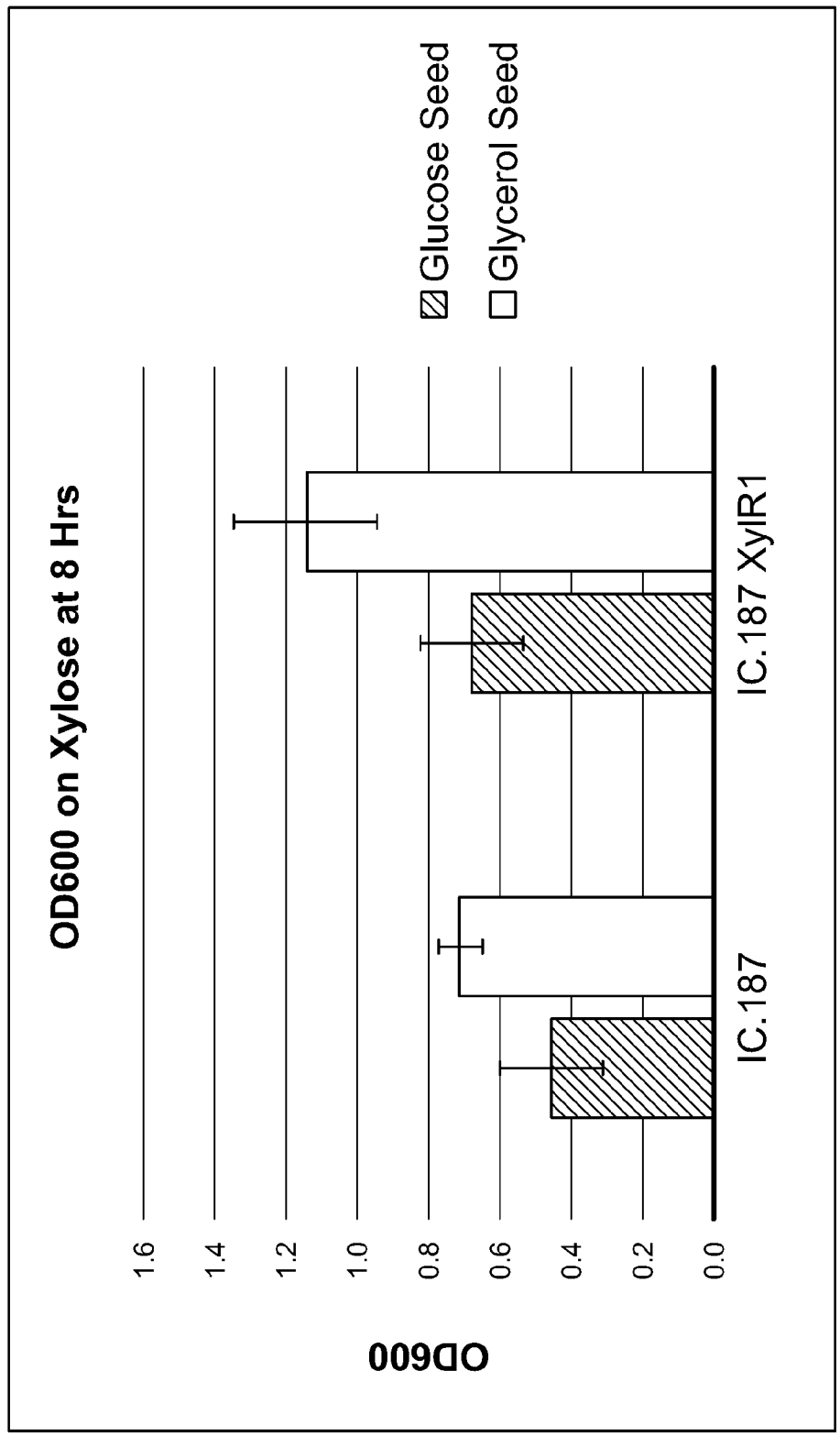
FIG. 2 is a chart illustrating improved growth in the presence of xylose and that the improved growth is due to improved xylose utilization.
Figure 3:
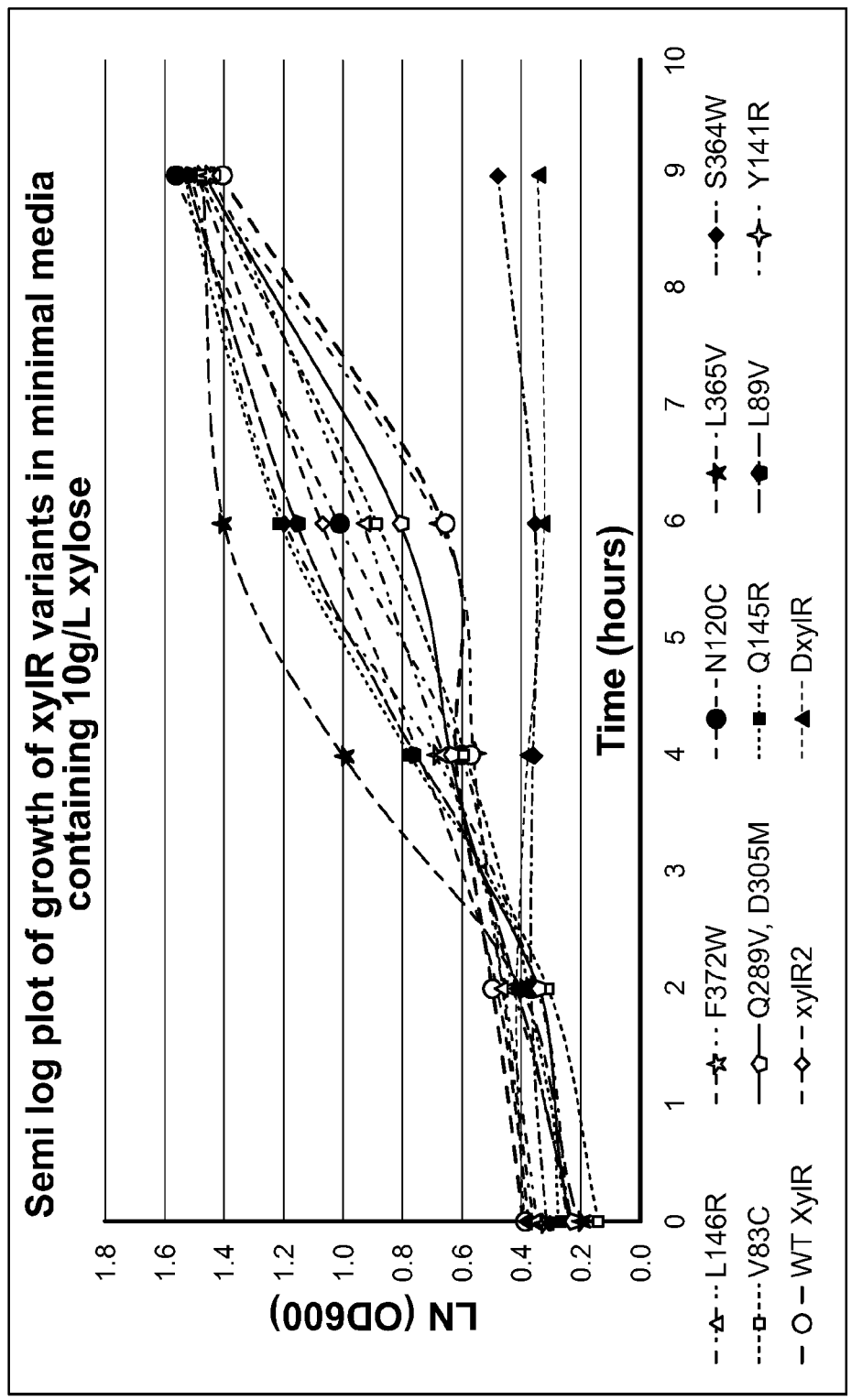
FIG. 3 is a chart illustrating the growth of xylR mutants L146R, F372W, N120C, L365V, S364W, V83C, (Q289V, D305M), Q145R, L89V, and Y141R compared to WT xylR growth in minimal media containing xylose.
Figure 4:
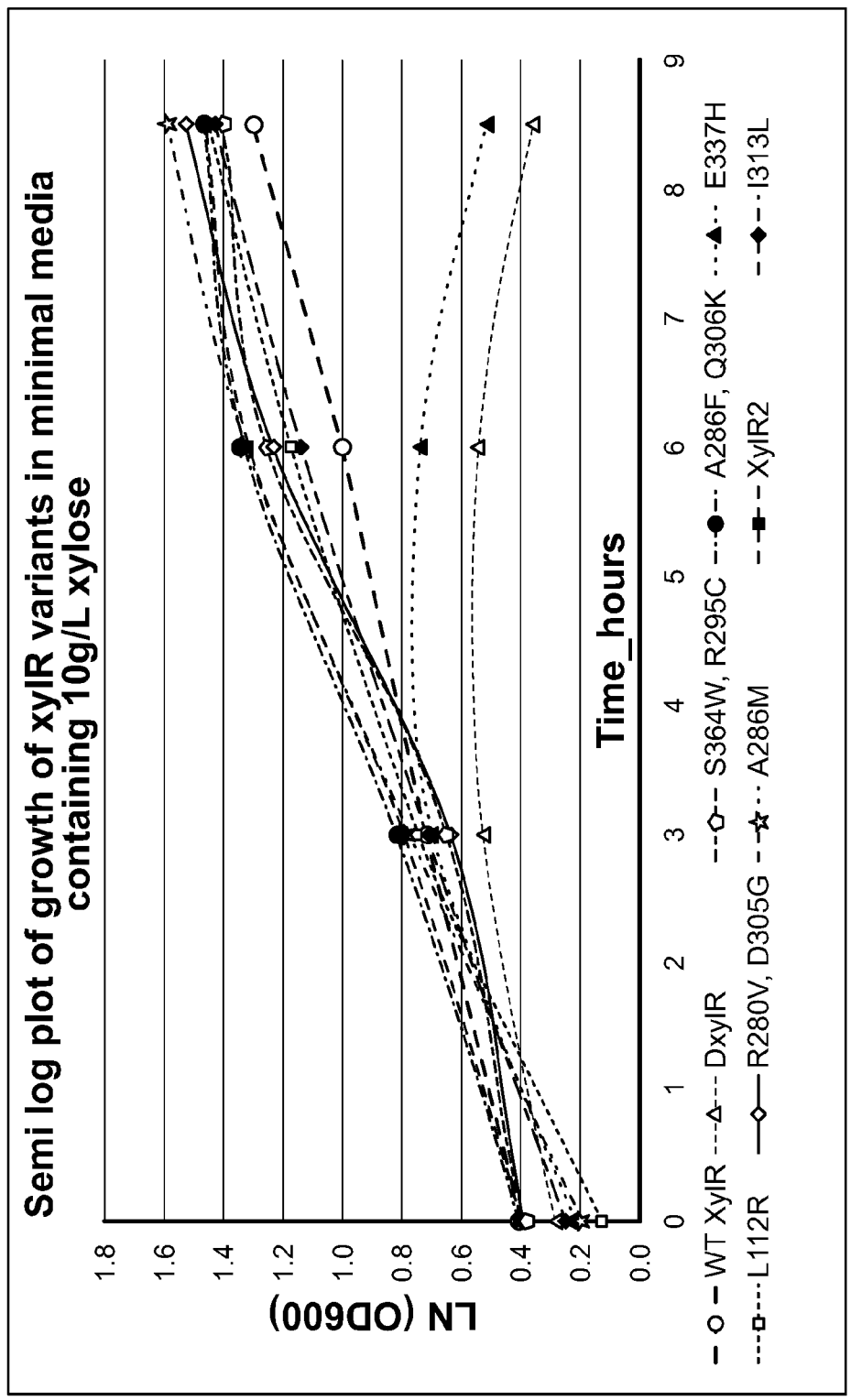
FIG. 4 is a chart illustrating the growth of xylR mutants (S364W, R295C), (A286F, Q306K), E337H, L112R, (R280V, D305G), A286M, and I313L compared to WT xylR in minimal media containing xylose.
Figure 5:
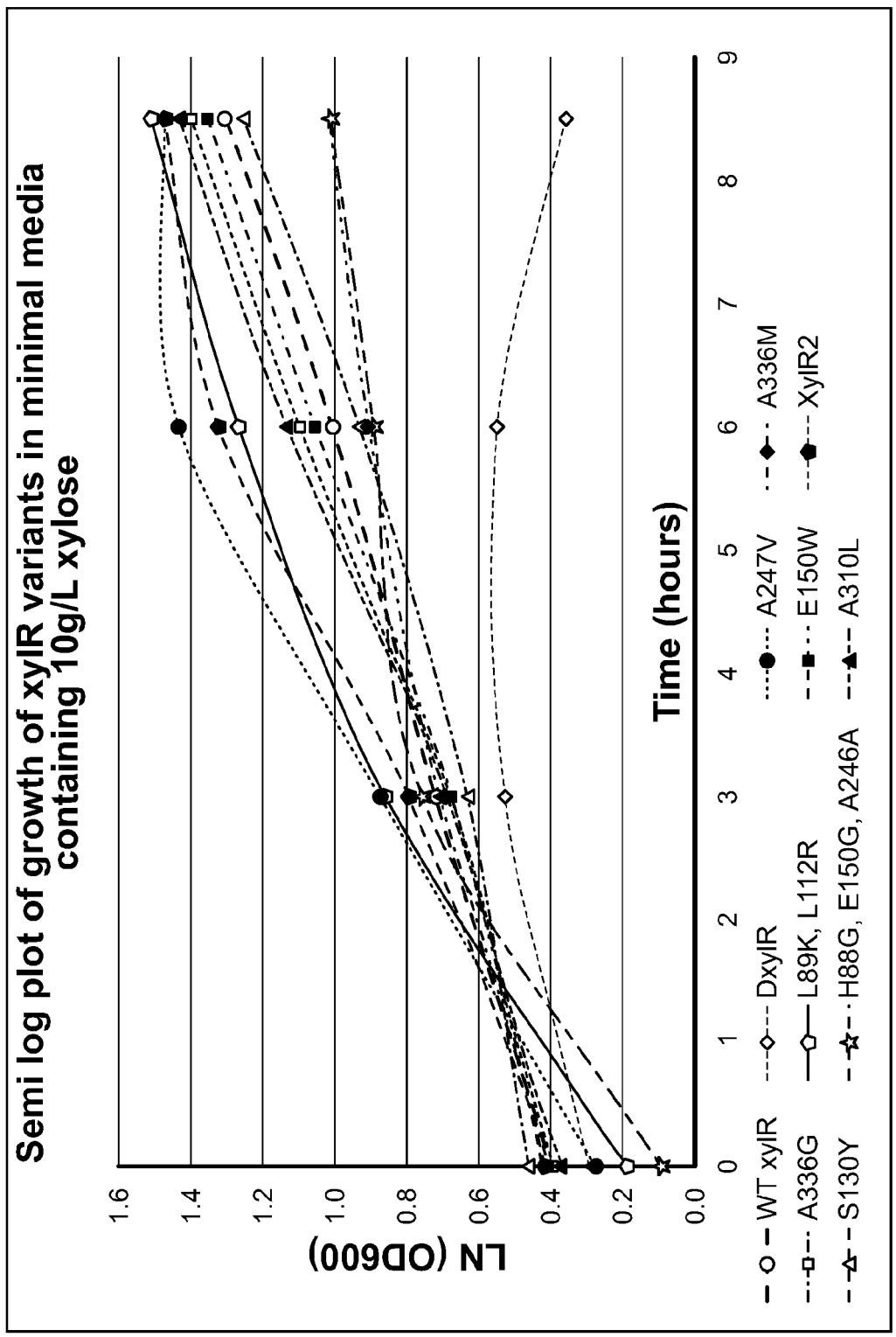
FIG. 5 is a chart illustrating the growth of xylR mutants A247V, A336M, A336G, (L89K, L112R), E150W, S130Y, (H88G, E150G, A246A*), and A310L compares with WT xylR in minimal media containing xylose. * indicates a silent mutation at the nucleic acid level (GCG→GCA).
Figure 6:
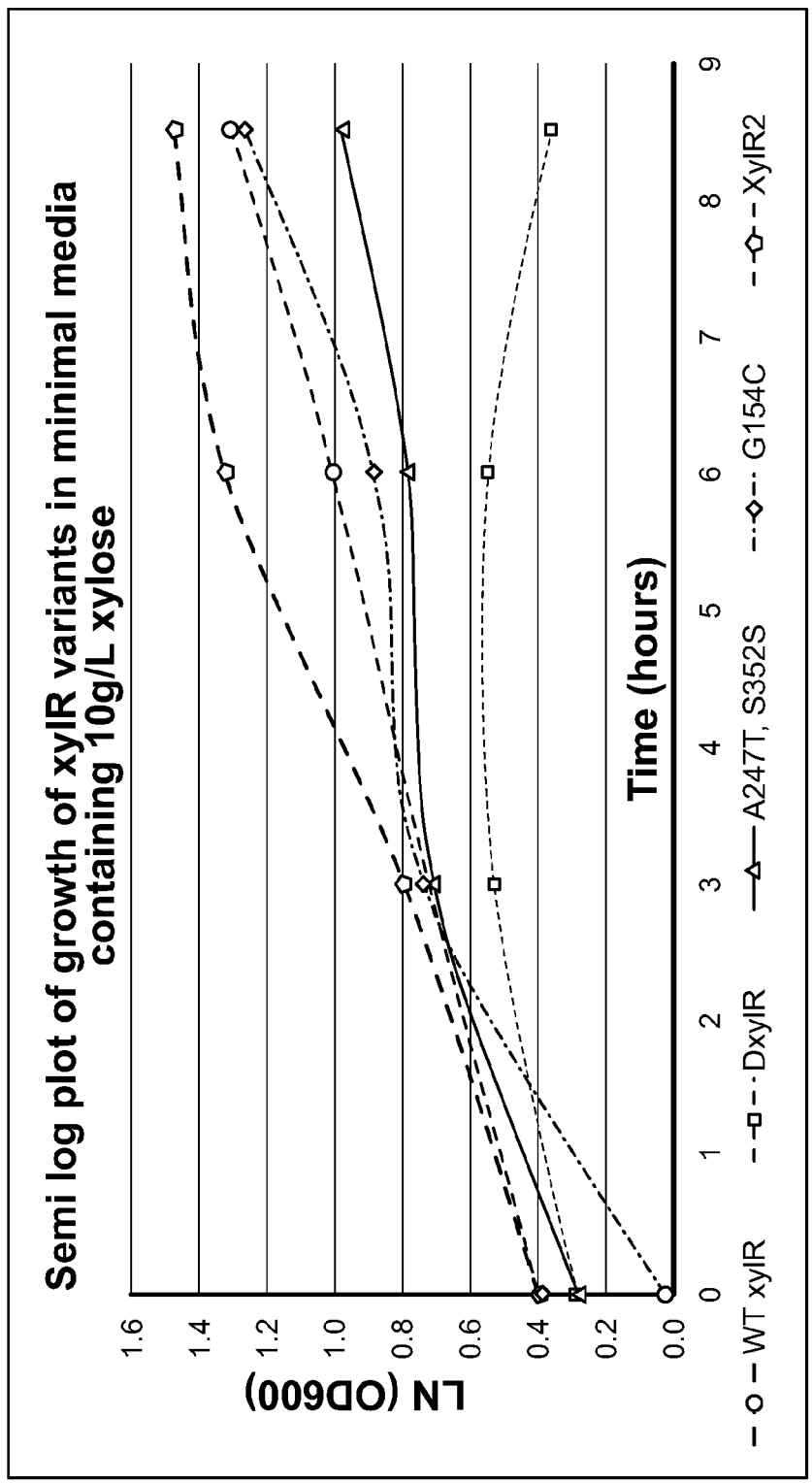
FIG. 6 is a chart illustrating the growth of xylR mutants (A247T, S352S*), and G154C compared to WT xylR in minimal media containing xylose. * indicates a silent mutation at the nucleic acid level (TCG→TCC).
Figure 7:
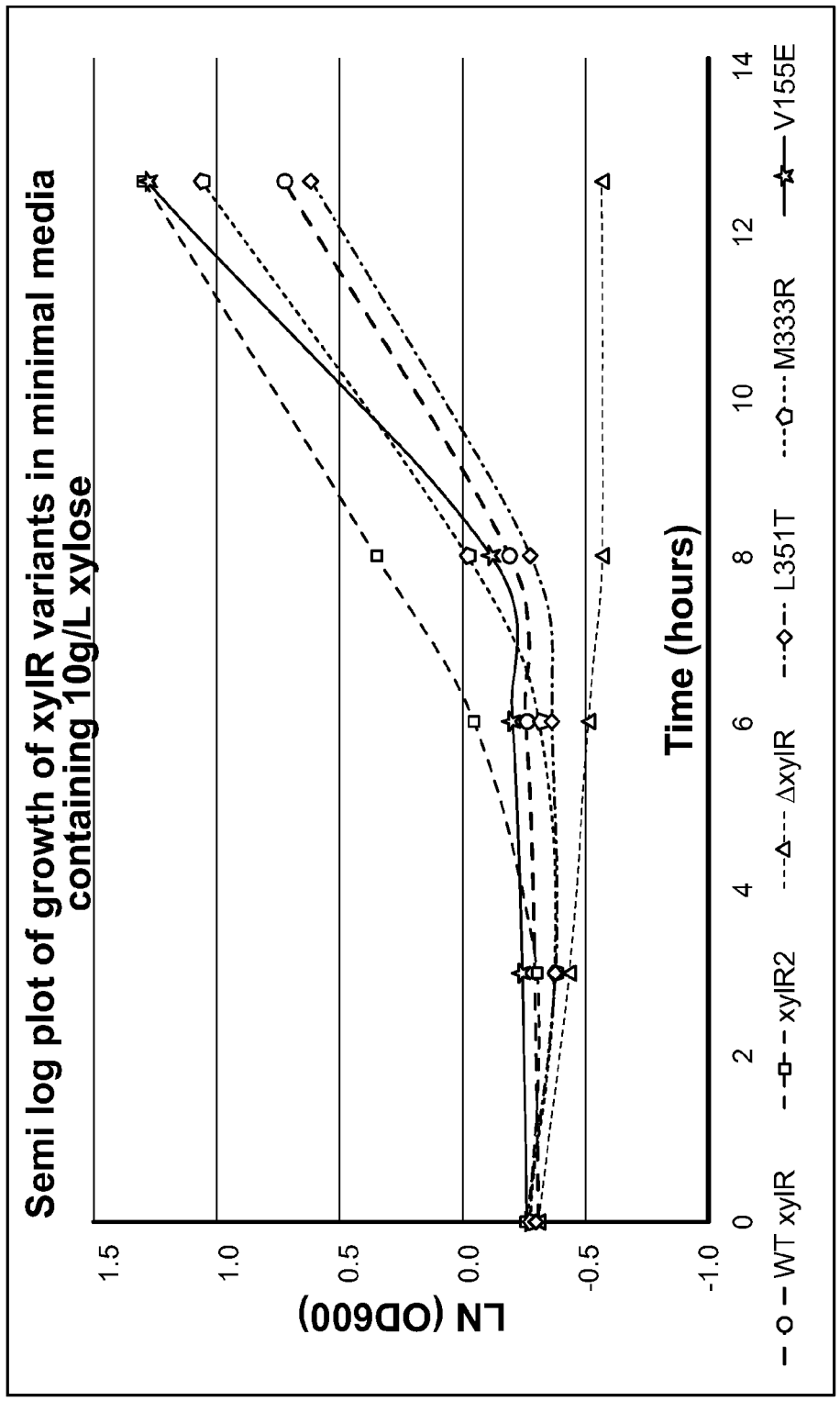
FIG. 7 is a chart illustrating the growth of xylR mutants L351T, M333R, and V155E compared to WT xylR in minimal media containing xylose.
Figure 8:
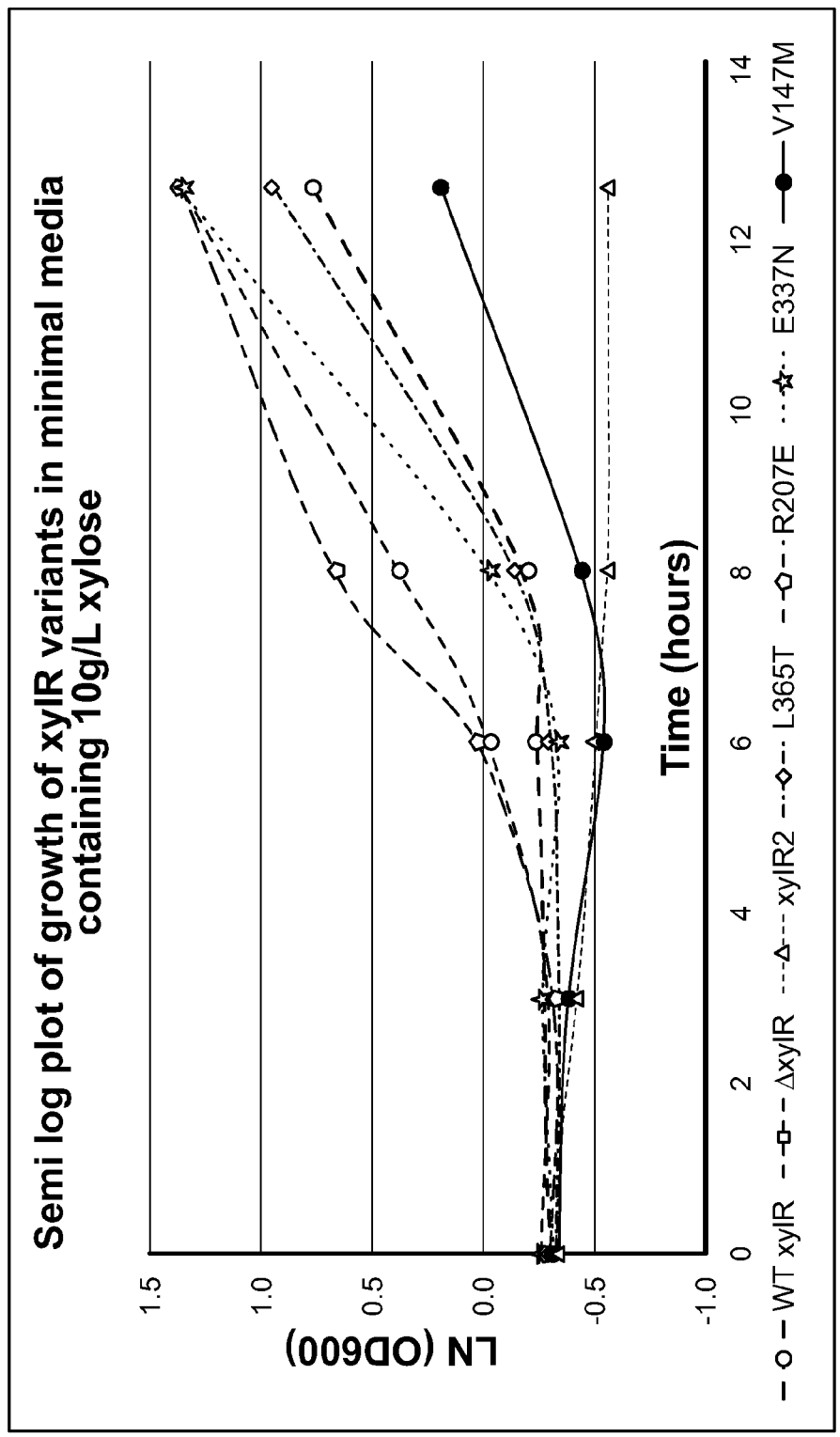
FIG. 8 is a chart illustrating the growth of xylR mutants L365T, R270E, E337N, and V147M compared to WT xylR in minimal media containing xylose.
Figure 9:
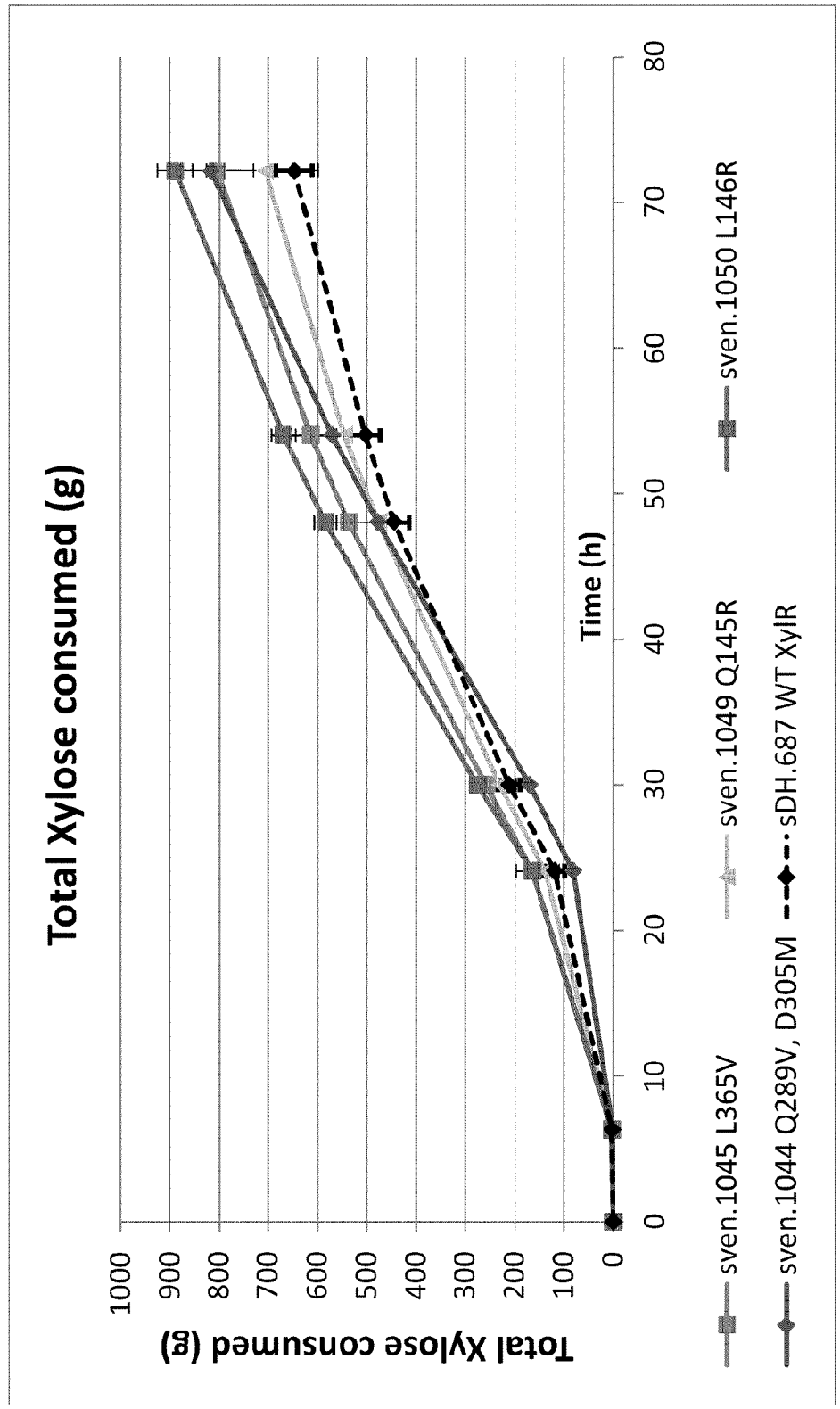
FIG. 9 Illustrates the utilization of xylose by the XylR mutants L365V, Q145R, L146R, and (Q289,D305M) compared to WT xylR grown in minimal media containing xylose.
Figure 10:
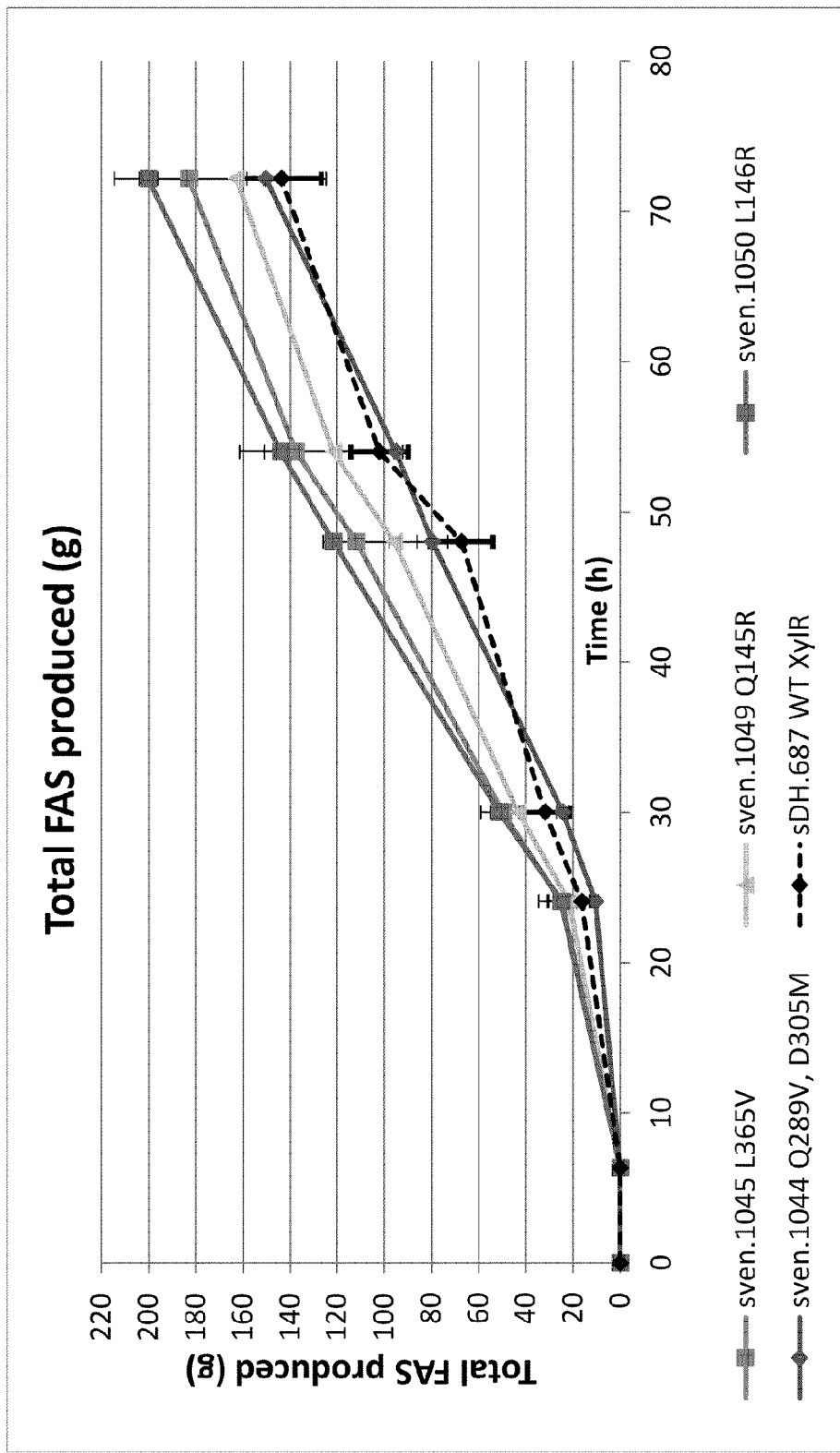
FIG. 10 Illustrates the productivity with respect to production of fatty acid species (FAS) of the XylR mutants L365V, Q145R L146R, and (Q289,D305M) compared to WT xylR grown in minimal media containing xylose.
Figure 11:
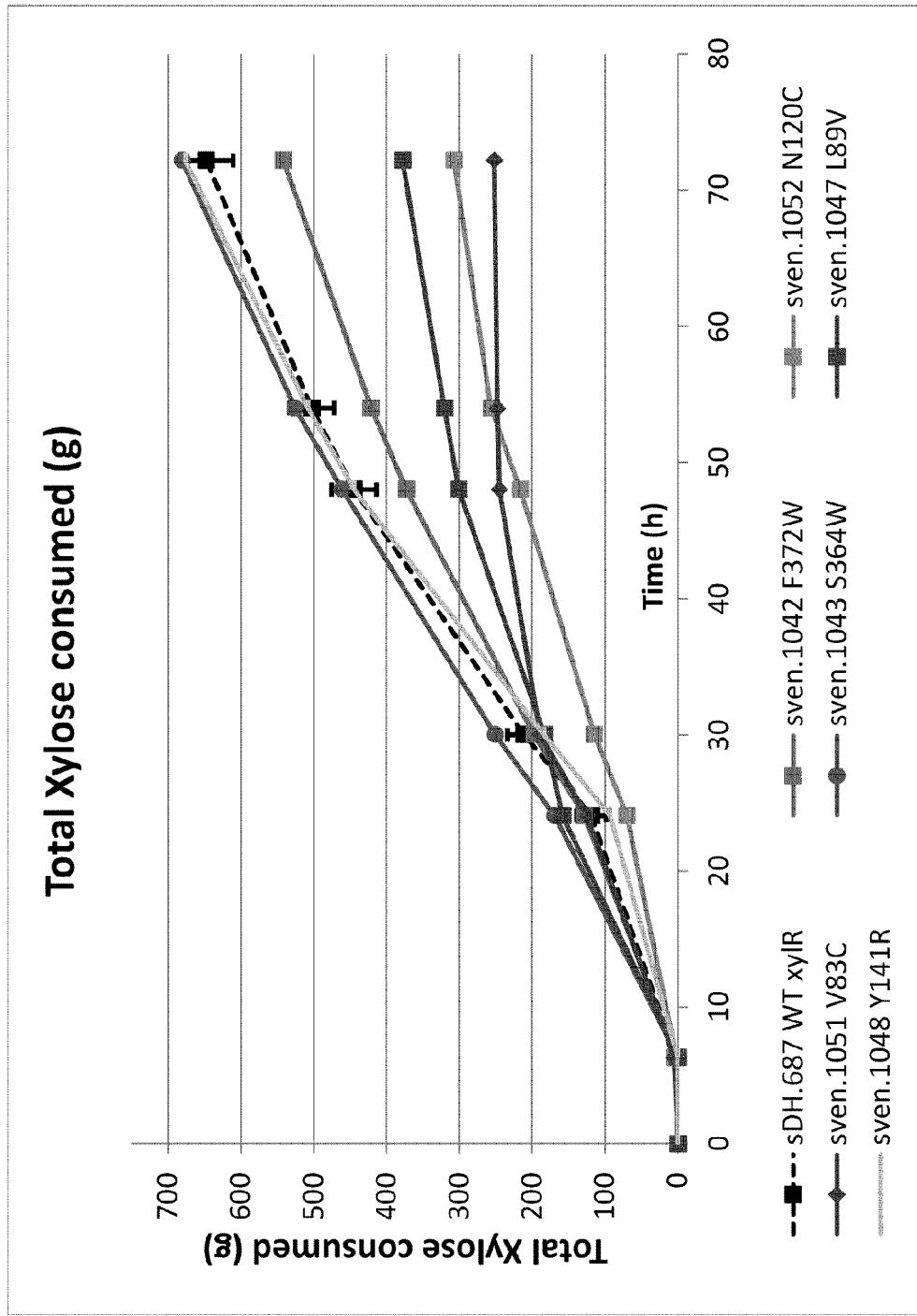
FIG. 11 Illustrates the utilization of xylose by the XylR mutants F372W, N120C, V83C, S364W, L89V, and Y141R compared to WT xylR grown in minimal media containing xylose.
Figure 12:
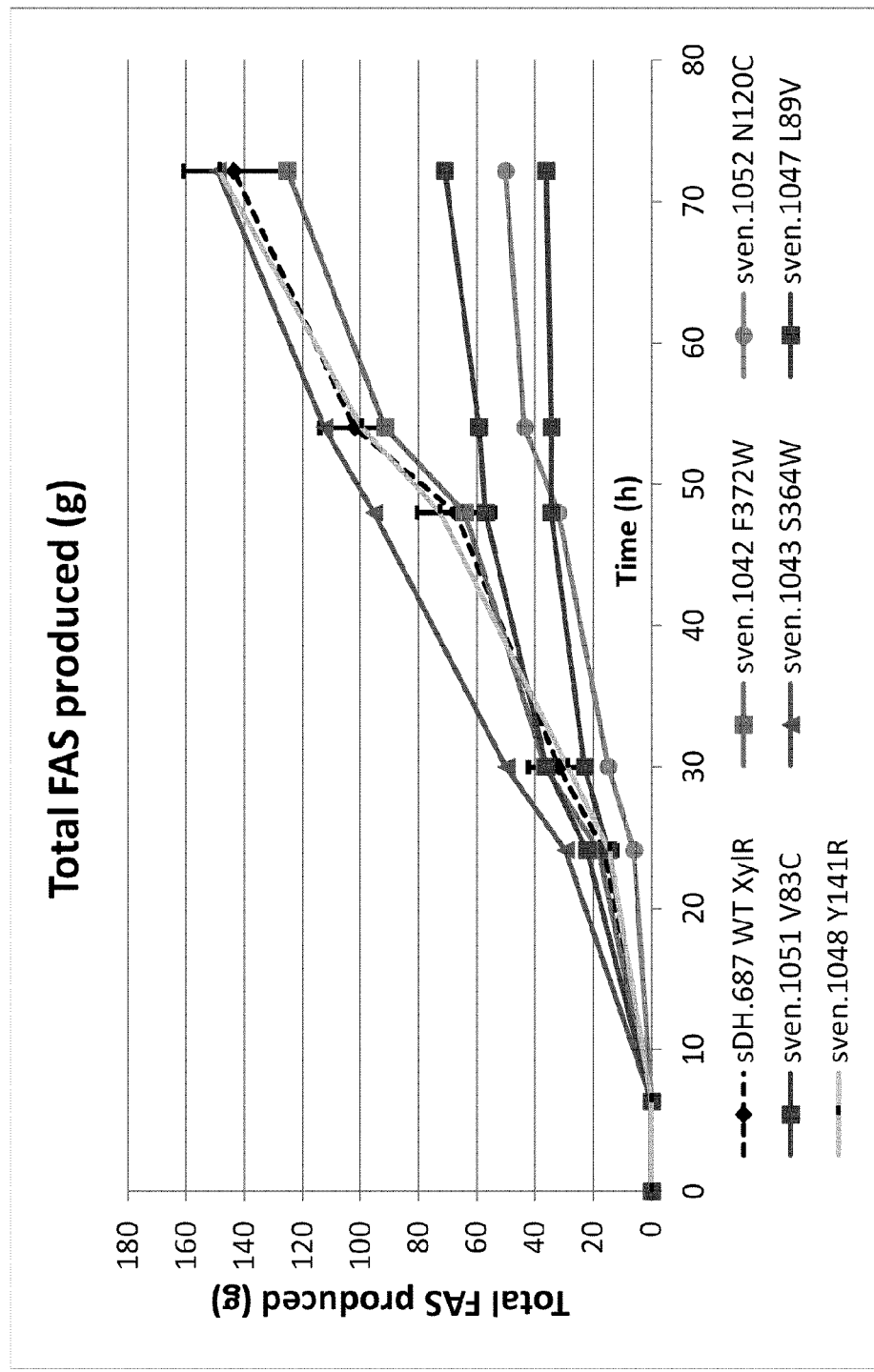
FIG. 12 Illustrates the productivity with respect to production of fatty acid species (FAS) of XylR mutants R372W, N120C, V83C, S364W, L89V, and Y141R compared to WT xylR grown in minimal media containing xylose.
Figure 13:
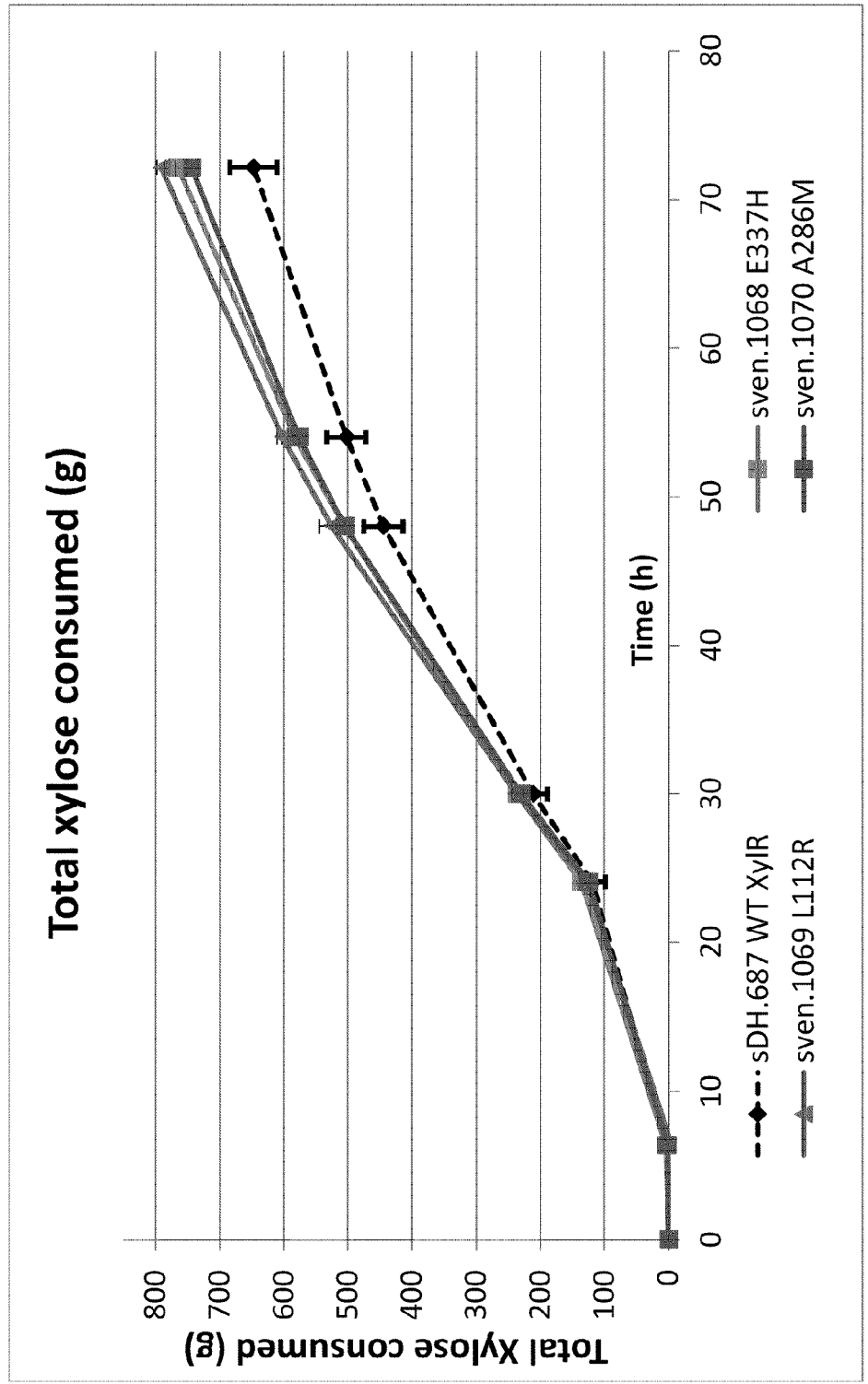
FIG. 13 Illustrates the utilization of xylose by the XylR mutants E337H, L112R, and A286M compared to WT xylR grown in minimal media containing xylose.
Figure 14:
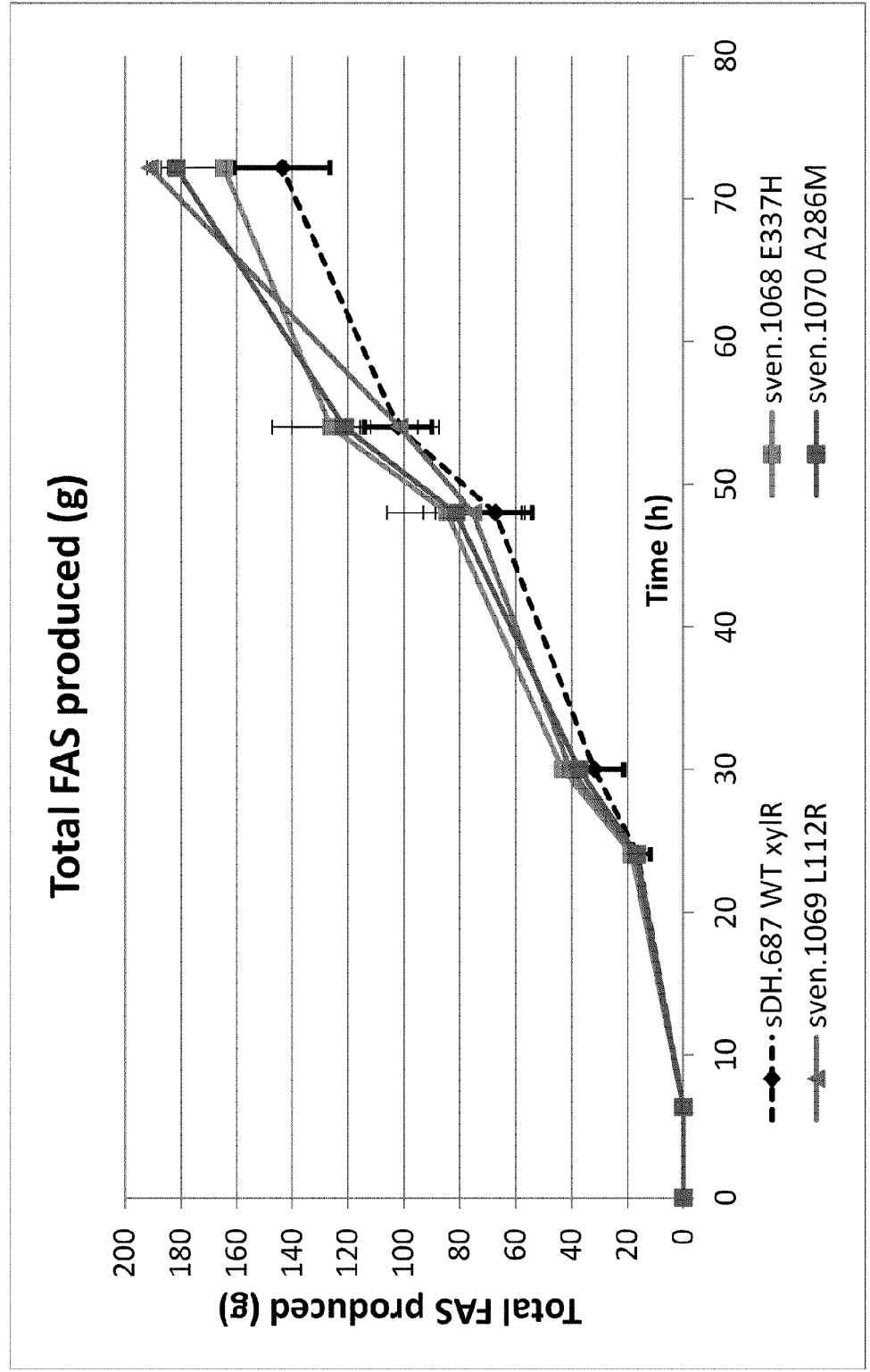
FIG. 14 Illustrates the productivity with respect to production of fatty acid species (FAS) of XylR mutants E337H, L112R, and A286M compared to WT xylR grown in minimal media containing xylose.
Figure 15:
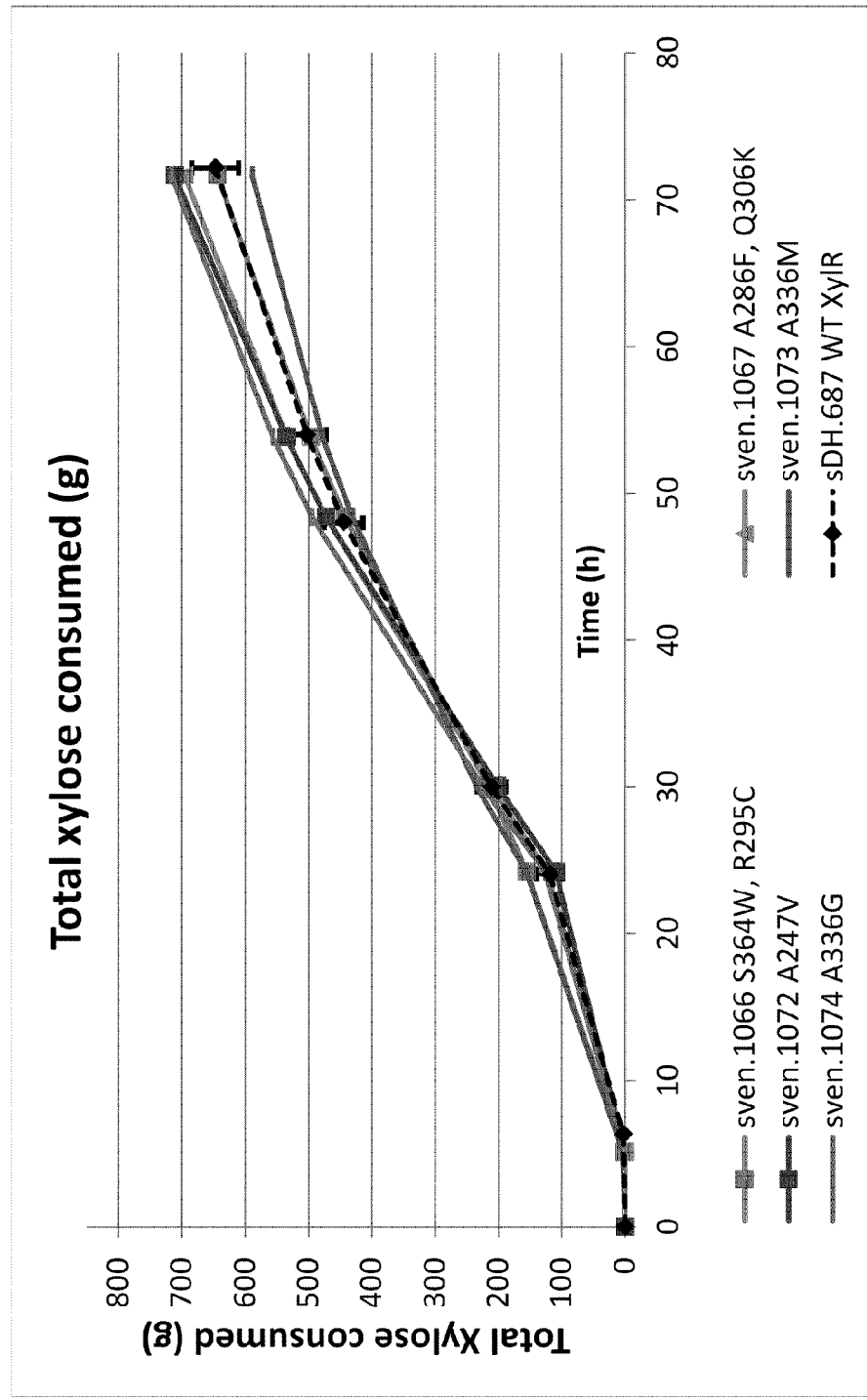
FIG. 15 Illustrates the utilization of xylose by the XylR mutants (S364W, R295C), (A286F, Q306K), A247V, A336M, and A336G compared to WT xylR grown in minimal media containing xylose.
Figure 16:
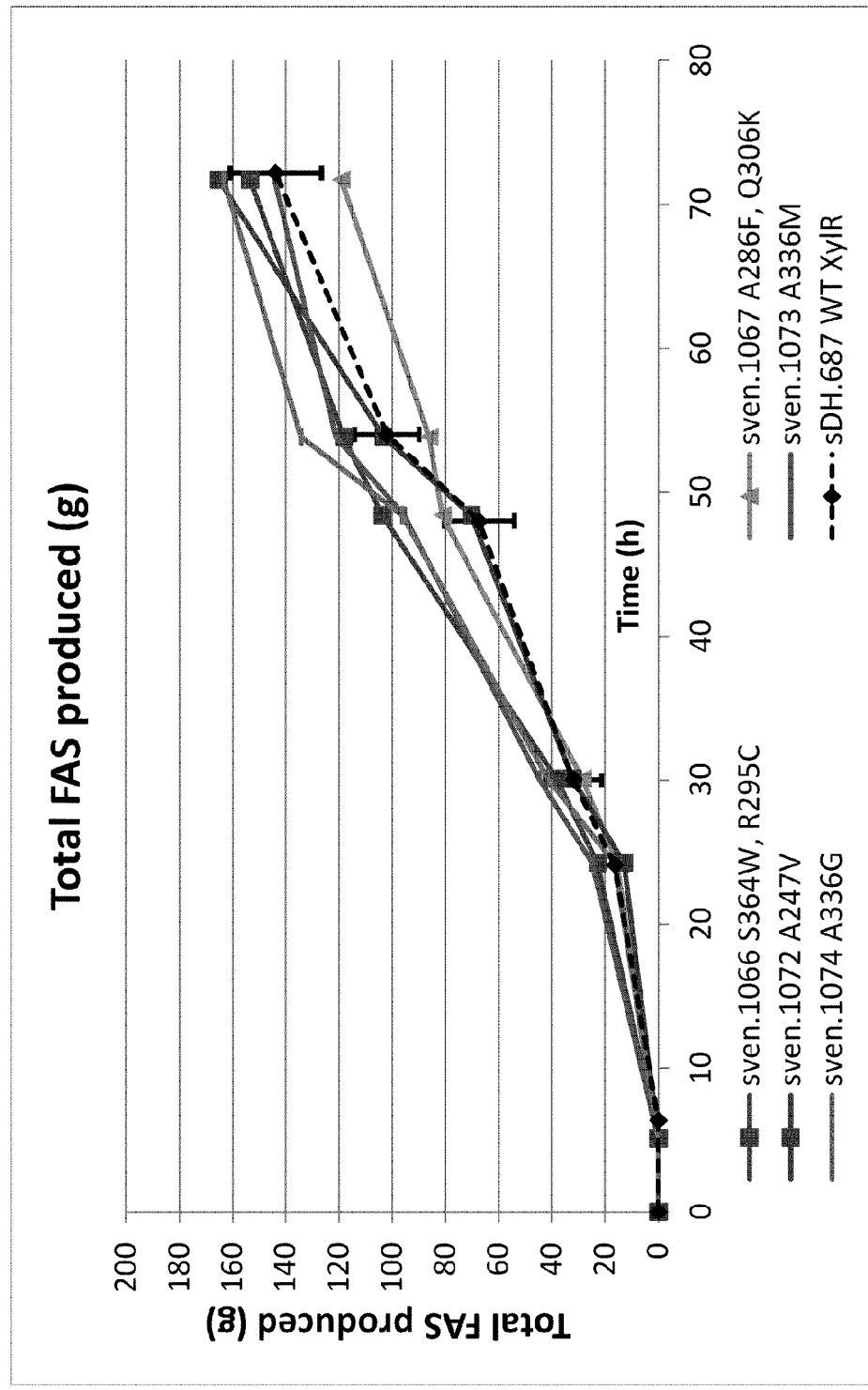
FIG. 16 Illustrates the productivity with respect to production of fatty acid species (FAS) of XylR mutants (S364W, R295C), (A286F, Q306K), A247V, A336M, and A336G compared to WT xylR grown in minimal media containing xylose.

As can be seen in FIG. 2, the strain expressing wild type xylR (IC.187) whether started from a glucose or glycerol seed grew more slowly than the strain expressing the xylR1 (E382K) mutant. Thus, cells expressing the xylR1 mutant show improved growth in the presence of xylose whether transitioning from a glucose or glycerol seed culture.

From previous experiments, it is known that the glucose or glycerol is fully consumed after the seed culture is finished growing. Glucose represses the xylose operons via carbon catabolite repression, whereas glycerol is a neutral sugar which does not repress the xylose operons. Thus, no matter whether transitioning from a sugar exhibiting carbon catabolite repression or a neutral sugar, the cells grow faster on xylose with the xylR1 mutation, indicating a faster xylose utilization rate in both cases.

Example 3

This example illustrates the construction and testing of new XylR mutants having improved xylose utilization and/or improved co-utilization of glucose and xylose.

The wild-type XylR nucleic acid (SEQ ID NO:2) was cloned into template plasmid pSven.178. Transfer PCR (tPCR) was used to generate mutants that were subsequently tested for their capacity to permit growth on xylose. Transfer PCR was carried out using methods known in the art.

Briefly, a template plasmid (pSven.178=p15A-lacI-PxylR-xylR (WT)-KanR) was constructed. The plasmid comprises the upstream and downstream homology to the xylR genomic sequence that is necessary for genomic integration of the resulting XylR mutants in *E. coli*. Transfer PCR was carried out using the template plasmid and a combination of forward (5'-3') primers that contain desired mutations and the reverse primer. PCR was then used to amplify from tPCR template using external primers that amplify the sequences containing diversity and homology regions.

The amplified mutants were cut with a restriction enzyme (Dpn1) to release the mutagenized XylR gene and regions of homology for integration. The linear DNA product comprising the XylR mutations and homology regions was integrated into the xylR locus of *E. coli* strain sven.999 (see e.g., Datsenko and Wanner, 2000, PNAS, 97 (12), 6640-6645).

The sven.999 strain comprises a deletion of the native XylR gene and is unable to grow on minimal media containing xylose as the sole carbon source. Accordingly, only bacteria that have integrated a XylR mutant that has the ability to utilize xylose will be able to grow on the minimal plates.

Once the colonies containing xylR mutants in the ΔxylR locus were obtained, a serial passaging approach was used to identify xylR variants that can support growth on minimal media containing xylose.

Colonies from the serial passaging approach were isolated and screened for growth comparison with the control strains containing WT xylR protein and xylR2 (R121C).

Table 3 and FIGS. 3-8 illustrate how growth of xylR mutants compares with WT xylR in minimal media containing xylose.

To measure growth on xylose, control strains KTT.560 (WT XylR), sCR.002 (XylR2 R121C) and sven.996 (ΔxylR) along with the various xylR mutant strains were screened for growth in minimal media with xylose. The colonies were initially grown on LB media for 4-6 hours and transferred to minimal media containing limited phosphate and other nutrients and glycerol as the carbon source. The culture was grown overnight and was used to subculture into fresh phosphate limited minimal media containing xylose as the carbon source. The optical density (OD) of the culture was periodically measured at 600 nm wavelength (OD600) to measure the growth of strains with respect to the controls. All data shown is an average of 3 replicates of each strain.

TABLE 3

Point Mutations in XylR Protein, Nucleotide Codon Changes, and Ranking of Mutants for Growth on Xylose Compared to Control

| Mutation over WT | Strain Moniker | μ (hr$^{-1}$) ranking | FOIC OD ranking | Mutational codon | Final production strain |
|---|---|---|---|---|---|
| V83C | sven.1041 | + | ++ | TGC | sven.1052 |
| L89K, L112R | sven.1063 | - | + | AAG, CGC | sven.1075 |
| H88G, E150G, A246A | sven.1059 |  | + | GGG, GGG, GCA | sven.1071 |
| L112R | sven.1057 | + | + | CGC | sven.1069 |
| N120C | sven.1040 | - | + | TGT | sven.1051 |
| Y141R | sven.1037 | -- | + | AGG | sven.1048 |
| Q145R | sven.1038 | ++ | ++ | CGG | sven.1049 |
| L146R | sven.1039 | + | ++ | AGG | sven.1050 |
| V147M | sven.1089 | + | +++ | ATG | sven.1106 |
| E150W | sven.1081 | + | ++ | TGG | sven.1098 |
| G154C | sven.1082 | --- | - | TGC | sven.1099 |
| V155E | sven.1083 | +++ | + | GAG | sven.1100 |
| A247V | sven.1060 | - | + | GTC | sven.1072 |
| A247T, S352S | sven.1064 | -- | - | ACA, TCC | sven.1076 |
| R270E | sven.1086 | +++ | + | GAG | sven.1102 |
| R280V, D305G | sven.1078 | + | + | GTT, GGG | sven.1095 |
| A286M | sven.1058 | - | + | ATG | sven.1070 |
| A286F, Q306K | sven.1055 | + | + | TTT, AAG | sven.1067 |
| Q289V, D305M | sven.1033 | + | + | GTG, ATG | sven.1044 |
| R295C, S364W | sven.1054 | --- | - | TGG, TGT | sven.1066 |
| I313L | sven.1077 | - | + | CTT | sven.1094 |
| M333R | sven.1088 | ++ | + | AGG | sven.1105 |
| A336M | sven.1061 | --- | - | ATG | sven.1073 |
| A336G | sven.1062 | - | + | GGT | sven.1074 |
| E337N | sven.1085 | - | -- | AAC | sven.1103 |
| E337H | sven.1056 | + | + | CAC | sven.1068 |
| L351T | sven.1087 | + | - | ACG | sven.1104 |
| S364W | sven.1032 | --- | -- | TGG | sven.1043 |
| L365T | sven.1084 | ++ | - | ACG | sven.1101 |
| L365V | sven.1034 | + | +++ | GTG | sven.1045 |
| F372W | sven.1031 | - | + | TGG | sven.1042 |
| WT xylR | KTT.560 |  |  |  | sDH.687 |
| R121C | sCR.002 | + | + | TGC | sven.954 |
| DxylR | sven.996 | --- | -- |  |  |

Table 3 Key: μ and FOIC ranking criteria.
+ Up to 50% higher;
++ Between 50% and 100% higher;
+++ More than 100% higher;
− Up to 25% lower;
-- Between 25% and 50% lower;
--- More than 50% lower.
μ is the growth rate of cells defined in inverse of time unit. It is a measure of change in number of cells per unit time.

All comparisons were made with respect to control strain KTT.560 with WT XylR. The controls were KTT.560=WT xylR; sCR.002=xylR2; sven.996=ΔxylR; sDH.687=KTT.560 pDH.138; sven.954=KTT.560 xylR2 pDH.138; sven.1053=KTT.560 ΔxylR pDH.138.

FOIC=Fold Over Internal Control. Internal Control=WT XylR (KTT.560). The OD600 of mutant strains during mid log phase are expressed as fold higher than the control strain KTT.560. All final production strains contain production plasmid pDH.138 comprising *Marinobacter hydrocarbonoclasticus* ester synthase. Plasmid pDH.138 is a production plasmid containing SC101 origin of replication, Spectinomycin resistance, IPTG inducible PTrc promoter and a variant of Ester Synthase. Genotype description of the plasmid is below:

ori_SC101, repA, par, aadAl-terminator(B1004), lacIq-terminator(T22), Ptrc_linkerD_IGR19-ES50_term (rrnB_T1T2)

Selected XylR mutants were further tested with respect to growth on xylose minimal media and their ability to produce various fatty acid species (FAS) was determined. Growth was monitored by periodically measuring OD600 as described above. FAS production was measured using standard methods known in the art.

Table 4 and FIGS. 9-16 illustrate xylose utilization and productivity with respect to production of FAS for various XylR mutants compared to WT xylR grown in minimal media containing xylose.

TABLE 4

Performance metrics of xylR mutants compared to WT xylR and ranking compared to control

| Strain | Mutation | Xylose consumption ranking | FAS production ranking |
|---|---|---|---|
| sDH.687 | WT XylR | -- | -- |
| sven.1042 | F372W | -- | -- |
| sven.1052 | N120C | --- | --- |
| sven.1051 | V83C | --- | --- |
| sven.1043 | S364W | + | - |
| sven.1048 | Y141R | + | - |
| sven.1047 | L89V | --- | --- |
| sven.1045 | L365V | ++ | ++ |
| sven.1049 | Q145R | + | + |
| sven.1050 | L146R | +++ | +++ |
| sven.1044 | Q289V D305M | +++ | - |
| Sven.1066 | S364W, R295C | - | - |
| Sven.1067 | A286F, Q306K | + | --- |
| Sven.1072 | A247V | + | + |
| Sven.1073 | A336M | -- | -- |
| Sven.1074 | A336G | + | + |
| Sven.1068 | E337H | + | + |
| sven.1069 | L112R | ++ | ++ |
| sven.1070 | A286M | ++ | ++ |

Table 4 Key: Xylose consumption and FAS production ranking.
+ Up to 10% higher;
++ Between 10% and 20% higher;
+++ More than 20% higher;
− Up to 10% lower;
-- Between 10% and 20% lower;
--- More than 20% lower.
All comparisons made with respect to control strain sDH.687 with WT XylR.

Example 4

This example illustrates mutations at position 121 of SEQ ID NO:1 that when expressed in a recombinant host cell confer upon the host cell the capacity to consume xylose faster than an otherwise isogenic host cell that expresses SEQ ID NO:1.

Table 5 lists specific substitutions at position 121 and their effects on xylose consumption relative to the wild-type sequence. International Application No. PCT/US2014/027337 is herein incorporated by reference.

TABLE 5

Amino Acid Substitutions Relieving Catabolite Repression

| Amino acid | Faster xylose consumption than WT (Arg) |
| --- | --- |
| Cysteine | Yes |
| Serine | Yes (original mutation) |
| Threonine | Yes |
| Glycine | Yes |
| Histidine | Yes |
| Valine | Yes |
| Methioine | Yes |
| Tyrosine | Yes |
| Isoleucine | Yes |
| Alanine | Yes |
| Leucine | Yes |
| Proline | Yes |
| Phenylalanine | Yes |
| Tryptophane | Possibly (depending on time course) |

APPENDIX A

SEQ ID NO: 1 XylR wild type Protein Sequence
(Genbank #NC_000913; E. coli K-12 MG1655; Blattner
and Plunkett, 1997; NCBI Protein ID: NP_418026)
METKRHRITLLFNANKAYDRQVVEGVGEYLQASQSEWDIFIEEDFRARID

KIKDWLGDGVIADFDDKQIEQALADVDVPIVGVGGSYHLAESYPPVHYIA

TDNYALVESAFLHLKEKGVNRFAFYGLPESSGKRWATEREYAFRQLVAEE

KYRGVVYQGLETAPENWQHAQNRLADWLQTLPPQTGIIAVTDARARHILQ

VCEHLHIPVPEKLCVIGIDNEELTRYLSRVALSSVAQGARQMGYQAAKLL

HRLLDKEEMPLQRILVPPVRVIERRSTDYRSLTDPAVIQAMHYIRNHACK

GIKVDQVLDAVGISRSNLEKRFKEEVGETIHAMIHAEKLEKARSLLISTT

LSINEISQMCGYPSLQYFYSVFKKAYDTTPKEYRDVNSEVML

SEQ ID NO: 2 XylR WT DNA Sequence (Genbank #NC_
000913; E. coli K-12 MG1655; Blattner and
Plunkett, 1997; NCBI Protein ID: NP_418026)
ATGTTTACTAAACGTCACCGCATCACATTACTGTTCAATGCCAATAAAGC

CTATGACCGGCAGGTAGTAGAAGGCGTAGGGGAATATTTACAGGCGTCAC

AATCGGAATGGATATTTTCATTGAAGAAGATTTCCGCGCCCGCATTGAT

AAAATCAAGGACTGGTTAGGAGATGGCGTCATTGCCGACTTCGACGACAA

ACAGATCGAGCAAGCGCTGGCTGATGTCGACGTCCCCATTGTTGGGGTTG

GCGGCTCGTATCACCTTGCAGAAAGTTACCCACCCGTTCATTACATTGCC

ACCGATAACTATGCGCTGGTTAAAGCGCATTTTGCATTTAAAAGAGAA

AGGCGTTAACCGCTTTGCTTTTTATGGTCTTCCGGAATCAAGCGGCAAAC

GTTGGGCCACTGAGCGCGAATATGCATTTCGTCAGCTTGTCGCCGAAGAA

AAGTATCGCGGAGTGGTTTATCAGGGGTTAGAAACCGCGCCAGAGAACTG

GCAACACGCGCAAAATCGGCTGGCAGACTGGCTACAAACGCTACCACCGC

AAACCGGGATTATTGCCGTTACTGACGCCCGAGCGCGGCATATTCTGCAA

GTATGTGAACATCTACATATTCCCGTACCGGAAAAATTATGCGTGATTGG

CATCGATAACGAAGAACTGACCCGCTATCTGTCGCGTGTCGCCCTTTCTT

CGGTCGCTCAGGGCGCGCGGCAAATGGGCTATCAGGCGGCAAAACTGTTG

CATCGATTATTAGATAAAGAAGAAATGCCGCTACAGCGAATTTTGGTCCC

ACCAGTTCGCGTCATTGAACGGCGCTCAACAGATTATCGCTCGCTGACCG

ATCCCGCCGTTATTCAGGCCATGCATTACATTCGTAATCACGCCTGTAAA

GGGATTAAAGTGGATCAGGTACTGGATGCGGTCGGGATCTCGCGCTCCAA

TCTTGAGAAGCGTTTTAAAGAAGAGGTGGGTGAAACCATCCATGCCATGA

TTCATGCCGAGAAGCTGGAGAAAGCGCGCAGTCTGCTGATTTCAACCACC

TTGTCGATCAATGAGATATCGCAAATGTGCGGTTATCCATCGCTGCAATA

TTTCTACTCTGTTTTTAAAAAAGCATATGACACGACGCCAAAAGAGTATC

GCGATGTAAATAGCGAGGTCATGTTGTAG

SEQ ID NO: 3 (E382K) Protein Sequence:
MFTKRHRITLLFNANKAYDRQVVEGVGEYLQASQSEWDIFIEEDFRARID

KIKDWLGDGVIADFDDKQIEQALADVDVPIVGVGGSYHLAESYPPVHYIA

TDNYALVESAFLHLKEKGVNRFAFYGLPESSGKRWATEREYAFRQLVAEE

KYRGVVYQGLETAPENWQHAQNRLADWLQTLPPQTGIIAVTDARARHILQ

VCEHLHIPVPEKLCVIGIDNEELTRYLSRVALSSVAQGARQMGYQAAKLL

HRLLDKEEMPLQRILVPPVRVIERRSTDYRSLTDPAVIQAMHYIRNHACK

GIKVDQVLDAVGISRSNLEKRFKEEVGETIHAMIHAEKLEKARSLLISTT

LSINEISQMCGYPSLQYFYSVFKKAYDTTPK<u>K</u>YRDVNSEVML

SEQ ID NO: 4 XylR1 (E382K) DNA Sequence:
ATGTTTACTAAACGTCACCGCATCACATTACTGTTCAATGCCAATAAAGC

CTATGACCGGCAGGTAGTAGAAGGCGTAGGGGAATATTTACAGGCGTCAC

AATCGGAATGGATATTTTCATTGAAGAAGATTTCCGCGCCCGCATTGAT

AAAATCAAGGACTGGTTAGGAGATGGCGTCATTGCCGACTTCGACGACAA

ACAGATCGAGCAAGCGCTGGCTGATGTCGACGTCCCCATTGTTGGGGTTG

GCGGCTCGTATCACCTTGCAGAAAGTTACCCACCCGTTCATTACATTGCC

ACCGATAACTATGCGCTGGTTAAAGCGCATTTTGCATTTAAAAGAGAA

AGGCGTTAACCGCTTTGCTTTTTATGGTCTTCCGGAATCAAGCGGCAAAC

GTTGGGCCACTGAGCGCGAATATGCATTTCGTCAGCTTGTCGCCGAAGAA

AAGTATCGCGGAGTGGTTTATCAGGGGTTAGAAACCGCGCCAGAGAACTG

GCAACACGCGCAAAATCGGCTGGCAGACTGGCTACAAACGCTACCACCGC

AAACCGGGATTATTGCCGTTACTGACGCCCGAGCGCGGCATATTCTGCAA

GTATGTGAACATCTACATATTCCCGTACCGGAAAAATTATGCGTGATTGG

CATCGATAACGAAGAACTGACCCGCTATCTGTCGCGTGTCGCCCTTTCTT

CGGTCGCTCAGGGCGCGCGGCAAATGGGCTATCAGGCGGCAAAACTGTTG

APPENDIX A

```
CATCGATTATTAGATAAAGAAGAAATGCCGCTACAGCGAATTTTGGTCCC
ACCAGTTCGCGTCATTGAACGGCGCTCAACAGATTATCGCTCGCTGACCG
ATCCCGCCGTTATTCAGGCCATGCATTACATTCGTAATCACGCCTGTAAA
GGGATTAAAGTGGATCAGGTACTGGATGCGGTCGGGATCTCGCGCTCCAA
TCTTGAGAAGCGTTTTAAAGAAGAGGTGGGTGAAACCATCCATGCCATGA
```

APPENDIX A

```
TTCATGCCGAGAAGCTGGAGAAAGCGCGCAGTCTGCTGATTTCAACCACC
TTGTCGATCAATGAGATATCGCAAATGTGCGGTTATCCATCGCTGCAATA
TTTCTACTCTGTTTTTAAAAAAGCATATGACACGACGCCAAAAAAGTATC
GCGATGTAAATAGCGAGGTCATGTTGTAG
```

As is apparent to one of skill in the art, various modifications and variations of the above aspects and embodiments can be made without departing from the spirit and scope of this disclosure.

---

We claim:

1. An engineered XylR protein variant, comprising at least 80% sequence identity to SEQ ID NO: 1 and comprising at least one mutation corresponding to one or more of V83C, H88G, L89K, L112R, N120C, Y141R, Q145R, L146R, V147M, E150W, E150G, V155E, A247V, R270E, R280V, A286M, A286F, Q289V, D305M, D305G, Q306K, I313L, M333R, E337H, L351T, S364W, L365T, L365V, F372W, or E382K, with reference to SEQ ID NO: 1.

2. The engineered XylR protein variant of claim 1, wherein the engineered XylR protein variant has at least 85%, 90%, or 95% sequence identity to SEQ ID NO: 1.

3. The engineered XylR protein variant of claim 1, comprising at least one mutation corresponding to L112R, Y141R, Q145R, L146R, A247V, A286M, A286F, Q289V, R295C, E337H, S364W, or L365V, or a combination thereof.

4. The engineered XylR protein variant of claim 1, further comprising a mutation at an amino acid position corresponding to position 121 or 363 or a combination thereof.

5. The engineered XylR protein variant of claim 4, wherein the mutation at position 121 or 363 is R121C, R121S, R121T, R121G, R121H, R121V, R121M, R121Y, R121I, R121A, R121L, R121P, R121F, R121W, or P363S.

6. The engineered XylR protein variant of claim 1, wherein expression of the engineered XylR protein variant in a recombinant host cell confers improved growth on the recombinant host cell in comparison to the growth of a host cell expressing SEQ ID NO: 1, when the cells are cultured in the presence of xylose.

7. The engineered XylR protein variant of claim 1, wherein heterologous expression of a polynucleotide encoding the engineered XylR protein variant in a recombinant host cell confers improved xylose utilization, in comparison to a host cell expressing SEQ ID NO:1, when the cells are cultured in the presence of xylose.

8. The engineered XylR protein variant of claim 1, comprising at least one mutation corresponding to one or more of L112R, Q145R, L146R, A247V, A286M, E337H, or L365V.

9. A recombinant host cell that expresses the engineered XylR protein variant of claim 1, wherein the engineered XylR protein is encoded by a heterologous nucleic acid.

10. The recombinant host cell of claim 9, wherein:
expression of the engineered XylR protein variant in the recombinant host cell confers improved xylose utilization, in comparison to a host cell expressing SEQ ID NO:1, when the cells are cultured in the presence of xylose; and/or
expression of the engineered XylR protein variant in the recombinant host cell confers improved growth on the recombinant host cell in comparison to the growth of a host cell expressing SEQ ID NO: 1, when the cells are grown in the in the presence of xylose.

11. The recombinant host cell of claim 9, wherein the recombinant host cell is a species of *Escherichia*, *Bacillus*, *Lactobacillus*, *Pseudomonas*, *Aspergillus*, or *Marinobacter*.

12. The recombinant host cell of claim 9, wherein the recombinant host cell expresses at least one heterologous fatty acid derivative biosynthetic enzyme, and the recombinant host cell produces one or more fatty acid derivatives.

13. The recombinant host cell of claim 12, wherein the recombinant host cell produces an increased amount of fatty acid species (FAS) as compared to an otherwise isogenic host cell that expresses SEQ ID NO:1, when cultured in the presence of xylose.

14. A method for preparing a fatty acid derivative, the method comprising culturing, in a culture medium comprising xylose, the recombinant host cell of claim 12.

15. The recombinant host cell of claim 9, wherein the engineered XylR protein variant comprises at least one mutation corresponding to one or more of L112R, Q145R, L146R, A247V, A286M, E337H, L365V, and E382K.

16. The recombinant host cell of claim 9, wherein the engineered XylR protein variant further comprises a mutation at an amino acid position corresponding to position 121 or 363 of SEQ ID NO:1.

17. A method for increasing xylose utilization in a recombinant host cell, the method comprising:
culturing, in a culture medium comprising xylose, the recombinant host cell of claim 9,
wherein expression of the engineered XylR protein variant confers improved xylose utilization of the recombinant host cell in comparison to the xylose utilization of a host cell expressing SEQ ID NO: 1, when the cells are cultured in the presence of xylose.

18. The method of claim 17, wherein:
the recombinant host cell further comprises at least one heterologous fatty acid derivative biosynthetic enzyme; and
the recombinant host cell produces one or more fatty acid derivatives.

19. The method of claim 18, wherein:
the heterologous fatty acid derivative biosynthetic enzyme is one or more of an ester synthase, an acyl-ACP reductase (AAR), a thioesterase, an alcohol dehydrogenase, an ω-hydroxylase, an aldehyde reductase, an acyl-CoA synthetase, an acyl-CoA reductase (ACR), a carboxylic acid reductase (CAR), an aminotransferase, an amine dehydrogenase, an alcohol O-acyltransferase, a fatty alcohol-forming acyl-CoA reductase (FAR), a fatty acid decarboxylase, a decarbonylase, an oxidative deformylase, a fatty alcohol O-acetyl transferase, OleA having activity for production of ketones, or OleABCD having activity for production of internal olefins; and
the fatty acid derivative is a fatty acid, a fatty ester, a fatty acid methyl ester (FAME), a fatty acid ethyl ester (FAEE), a fatty alcohol acetate ester (FACE), a fatty alcohol, a fatty aldehyde, a hydrocarbon, a fatty amine, a fatty amide, an alkane, an alkene, a terminal olefin, an internal olefin, a fatty ketone, a fatty diacid, a fatty diol, a 1,3-fatty diol, an omega-hydroxy fatty acid, an omega-hydroxy diol, an omega-hydroxy FAME, or an omega-hydroxy FAEE, or a combination thereof.

20. The method of claim 17, wherein the engineered XylR protein variant comprises at least one mutation corresponding to one or more of L112R, Q145R, L146R, A247V, A286M, E337H, L365V, and E382K.

* * * * *

SEQUENCE LISTING

<160> NUMBER OF SEQ ID NOS: 5

<210> SEQ ID NO 1
<211> LENGTH: 392
<212> TYPE: PRT
<213> ORGANISM: Escherichia coli

<400> SEQUENCE: 1

```
Met Phe Thr Lys Arg His Arg Ile Thr Leu Leu Phe Asn Ala Asn Lys
1               5                   10                  15

Ala Tyr Asp Arg Gln Val Val Glu Gly Val Gly Tyr Leu Gln Ala
            20                  25                  30

Ser Gln Ser Glu Trp Asp Ile Phe Ile Glu Glu Asp Phe Arg Ala Arg
        35                  40                  45

Ile Asp Lys Ile Lys Asp Trp Leu Gly Asp Gly Val Ile Ala Asp Phe
    50                  55                  60

Asp Asp Lys Gln Ile Glu Gln Ala Leu Ala Asp Val Asp Val Pro Ile
65                  70                  75                  80

Val Gly Val Gly Gly Ser Tyr His Leu Ala Glu Ser Tyr Pro Pro Val
                85                  90                  95

His Tyr Ile Ala Thr Asp Asn Tyr Ala Leu Val Glu Ser Ala Phe Leu
            100                 105                 110

His Leu Lys Glu Lys Gly Val Asn Arg Phe Ala Phe Tyr Gly Leu Pro
        115                 120                 125

Glu Ser Ser Gly Lys Arg Trp Ala Thr Glu Arg Glu Tyr Ala Phe Arg
    130                 135                 140

Gln Leu Val Ala Glu Glu Lys Tyr Arg Gly Val Val Tyr Gln Gly Leu
145                 150                 155                 160

Glu Thr Ala Pro Glu Asn Trp Gln His Ala Gln Asn Arg Leu Ala Asp
                165                 170                 175

Trp Leu Gln Thr Leu Pro Pro Gln Thr Gly Ile Ile Ala Val Thr Asp
            180                 185                 190

Ala Arg Ala Arg His Ile Leu Gln Val Cys Glu His Leu His Ile Pro
        195                 200                 205

Val Pro Glu Lys Leu Cys Val Ile Gly Ile Asp Asn Glu Glu Leu Thr
    210                 215                 220

Arg Tyr Leu Ser Arg Val Ala Leu Ser Ser Val Ala Gln Gly Ala Arg
225                 230                 235                 240

Gln Met Gly Tyr Gln Ala Ala Lys Leu Leu His Arg Leu Leu Asp Lys
                245                 250                 255

Glu Glu Met Pro Leu Gln Arg Ile Leu Val Pro Pro Val Arg Val Ile
            260                 265                 270
```

Glu Arg Arg Ser Thr Asp Tyr Arg Ser Leu Thr Asp Pro Ala Val Ile
                275                 280                 285

Gln Ala Met His Tyr Ile Arg Asn His Ala Cys Lys Gly Ile Lys Val
        290                 295                 300

Asp Gln Val Leu Asp Ala Val Gly Ile Ser Arg Ser Asn Leu Glu Lys
305                 310                 315                 320

Arg Phe Lys Glu Val Gly Glu Thr Ile His Ala Met Ile His Ala
                325                 330                 335

Glu Lys Leu Glu Lys Ala Arg Ser Leu Leu Ile Ser Thr Thr Leu Ser
                340                 345                 350

Ile Asn Glu Ile Ser Gln Met Cys Gly Tyr Pro Ser Leu Gln Tyr Phe
            355                 360                 365

Tyr Ser Val Phe Lys Lys Ala Tyr Asp Thr Thr Pro Lys Glu Tyr Arg
        370                 375                 380

Asp Val Asn Ser Glu Val Met Leu
385                 390

<210> SEQ ID NO 2
<211> LENGTH: 1179
<212> TYPE: DNA
<213> ORGANISM: Escherichia coli

<400> SEQUENCE: 2

| | | | | | |
|---|---|---|---|---|---|
| atgtttacta | aacgtcaccg | catcacatta | ctgttcaatg | ccaataaagc | ctatgaccgg | 60 |
| caggtagtag | aaggcgtagg | ggaatattta | caggcgtcac | aatcggaatg | ggatattttc | 120 |
| attgaagaag | atttccgcgc | ccgcattgat | aaaatcaagg | actggttagg | agatggcgtc | 180 |
| attgccgact | cgacgacaa | acagatcgag | caagcgctgg | ctgatgtcga | cgtccccatt | 240 |
| gttgggttg | gcggctcgta | tcaccttgca | gaaagttacc | cacccgttca | ttacattgcc | 300 |
| accgataact | atgcgctggt | tgaaagcgca | tttttgcatt | taaaagagaa | aggcgttaac | 360 |
| cgctttgctt | tttatggtct | tccggaatca | agcggcaaac | gttgggccac | tgagcgcgaa | 420 |
| tatgcatttc | gtcagcttgt | cgccgaagaa | aagtatcgcg | gagtggttta | tcaggggtta | 480 |
| gaaaccgcgc | cagagaactg | gcaacacgcg | caaaatcggc | tggcagactg | gctacaaacg | 540 |
| ctaccaccgc | aaaccgggat | tattgccgtt | actgacgccc | gagcgcggca | tattctgcaa | 600 |
| gtatgtgaac | atctacatat | tcccgtaccg | gaaaaattat | gcgtgattgg | catcgataac | 660 |
| gaagaactga | cccgctatct | gtcgcgtgtc | gccctttctt | cggtcgctca | gggcgcgcgg | 720 |
| caaatgggct | atcaggcggc | aaaactgttg | catcgattat | tagataaaga | agaaatgccg | 780 |
| ctacagcgaa | ttttggtccc | accagttcgc | gtcattgaac | ggcgctcaac | agattatcgc | 840 |
| tcgctgaccg | atcccgccgt | tattcaggcc | atgcattaca | ttcgtaatca | cgcctgtaaa | 900 |
| gggattaaag | tggatcaggt | actggatgcg | gtcgggatct | cgcgctccaa | tcttgagaag | 960 |
| cgttttaaag | aagaggtggg | tgaaaccatc | catgccatga | ttcatgccga | gaagctggag | 1020 |
| aaagcgcgca | gtctgctgat | ttcaaccacc | ttgtcgatca | atgagatatc | gcaaatgtgc | 1080 |
| ggttatccat | cgctgcaata | tttctactct | gtttttaaaa | agcatatga | cacgacgcca | 1140 |
| aaagagtatc | gcgatgtaaa | tagcgaggtc | atgttgtag | | | 1179 |

<210> SEQ ID NO 3
<211> LENGTH: 392
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Met Phe Thr Lys Arg His Arg Ile Thr Leu Leu Phe Asn Ala Asn Lys
1               5                   10                  15
Ala Tyr Asp Arg Gln Val Val Glu Gly Val Gly Glu Tyr Leu Gln Ala
            20                  25                  30
Ser Gln Ser Glu Trp Asp Ile Phe Ile Glu Glu Asp Phe Arg Ala Arg
        35                  40                  45
Ile Asp Lys Ile Lys Asp Trp Leu Gly Asp Gly Val Ile Ala Asp Phe
    50                  55                  60
Asp Asp Lys Gln Ile Glu Gln Ala Leu Ala Asp Val Asp Val Pro Ile
65                  70                  75                  80
Val Gly Val Gly Gly Ser Tyr His Leu Ala Glu Ser Tyr Pro Pro Val
                85                  90                  95
His Tyr Ile Ala Thr Asp Asn Tyr Ala Leu Val Glu Ser Ala Phe Leu
            100                 105                 110
His Leu Lys Glu Lys Gly Val Asn Arg Phe Ala Phe Tyr Gly Leu Pro
        115                 120                 125
Glu Ser Ser Gly Lys Arg Trp Ala Thr Glu Arg Glu Tyr Ala Phe Arg
    130                 135                 140
Gln Leu Val Ala Glu Lys Tyr Arg Gly Val Val Tyr Gln Gly Leu
145                 150                 155                 160
Glu Thr Ala Pro Glu Asn Trp Gln His Ala Gln Asn Arg Leu Ala Asp
                165                 170                 175
Trp Leu Gln Thr Leu Pro Pro Gln Thr Gly Ile Ile Ala Val Thr Asp
            180                 185                 190
Ala Arg Ala Arg His Ile Leu Gln Val Cys Glu His Leu His Ile Pro
        195                 200                 205
Val Pro Glu Lys Leu Cys Val Ile Gly Ile Asp Asn Glu Glu Leu Thr
    210                 215                 220
Arg Tyr Leu Ser Arg Val Ala Leu Ser Ser Val Ala Gln Gly Ala Arg
225                 230                 235                 240
Gln Met Gly Tyr Gln Ala Ala Lys Leu Leu His Arg Leu Leu Asp Lys
                245                 250                 255
Glu Glu Met Pro Leu Gln Arg Ile Leu Val Pro Pro Val Arg Val Ile
            260                 265                 270
Glu Arg Arg Ser Thr Asp Tyr Arg Ser Leu Thr Asp Pro Ala Val Ile
        275                 280                 285
Gln Ala Met His Tyr Ile Arg Asn His Ala Cys Lys Gly Ile Lys Val
    290                 295                 300
Asp Gln Val Leu Asp Ala Val Gly Ile Ser Arg Ser Asn Leu Glu Lys
305                 310                 315                 320
Arg Phe Lys Glu Glu Val Gly Glu Thr Ile His Ala Met Ile His Ala
                325                 330                 335
Glu Lys Leu Glu Lys Ala Arg Ser Leu Leu Ile Ser Thr Thr Leu Ser
            340                 345                 350
Ile Asn Glu Ile Ser Gln Met Cys Gly Tyr Pro Ser Leu Gln Tyr Phe
        355                 360                 365
Tyr Ser Val Phe Lys Lys Ala Tyr Asp Thr Thr Pro Lys Lys Tyr Arg
    370                 375                 380
Asp Val Asn Ser Glu Val Met Leu
385                 390
```

<210> SEQ ID NO 4
<211> LENGTH: 1179
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
atgtttacta aacgtcaccg catcacatta ctgttcaatg ccaataaagc ctatgaccgg      60
caggtagtag aaggcgtagg ggaatattta caggcgtcac aatcggaatg ggatattttc     120
attgaagaag atttccgcgc ccgcattgat aaaatcaagg actggttagg agatggcgtc     180
attgccgact tcgacgacaa acagatcgag caagcgctgg ctgatgtcga cgtccccatt     240
gttggggttg gcggctcgta tcaccttgca gaaagttacc cacccgttca ttacattgcc     300
accgataact atgcgctggt tgaaagcgca ttttttgcatt taaaagagaa aggcgttaac     360
cgctttgctt tttatggtct tccggaatca agcggcaaac gttgggccac tgagcgcgaa     420
tatgcatttc gtcagcttgt cgccgaagaa agtatcgcg gagtggttta tcaggggtta     480
gaaaccgcgc cagagaactg gcaacacgcg caaaatcggc tggcagactg gctacaaacg     540
ctaccaccgc aaaccgggat tattgccgtt actgacgccc gagcgcggca tattctgcaa     600
gtatgtgaac atctacatat tcccgtaccg gaaaaattat gcgtgattgg catcgataac     660
gaagaactga cccgctatct gtcgcgtgtc gcccttttctt cggtcgctca gggcgcgcgg     720
caaatgggct atcaggcggc aaaactgttg catcgattat tagataaaga gaaatgccg      780
ctacagcgaa ttttggtccc accagttcgc gtcattgaac ggcgctcaac agattatcgc     840
tcgctgaccg atcccgccgt tattcaggcc atgcattaca ttcgtaatca cgcctgtaaa     900
gggattaaag tggatcaggt actggatgcg gtcgggatct cgcgctccaa tcttgagaag     960
cgttttaaag aagaggtggg tgaaaccatc catgccatga ttcatgccga gaagctggag    1020
aaagcgcgca gtctgctgat ttcaaccacc ttgtcgatca atgagatatc gcaaatgtgc    1080
ggttatccat cgctgcaata tttctactct gttttaaaaa aagcatatga cacgacgcca    1140
aaaaagtatc gcgatgtaaa tagcgaggtc atgttgtag                           1179
```

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 5

```
His His His His His His
1               5
```